US011466088B2

(12) United States Patent
Chao et al.

(10) Patent No.: US 11,466,088 B2
(45) Date of Patent: Oct. 11, 2022

(54) VEGFR-2 CAR IMMUNE CELLS TO TREAT CANCERS

(71) Applicant: Helix BioPharma Corp., Richmond Hill (CA)

(72) Inventors: Heman Lap Man Chao, Aurora (CA); Wah Yau Wong, Edmonton (CA); Baomin Tian, Edmonton (CA); Marni Diane Uger, Richmond Hill (CA)

(73) Assignee: Helix BioPharma Corp., Ontario (CA)

( * ) Notice: Subject to any disclaimer, the term of this patent is extended or adjusted under 35 U.S.C. 154(b) by 881 days.

(21) Appl. No.: 15/862,015

(22) Filed: Jan. 4, 2018

(65) Prior Publication Data
US 2018/0230219 A1 Aug. 16, 2018

Related U.S. Application Data

(60) Provisional application No. 62/535,330, filed on Jul. 21, 2017, provisional application No. 62/491,643, filed on Apr. 28, 2017, provisional application No. 62/480,712, filed on Apr. 3, 2017, provisional application No. 62/442,649, filed on Jan. 5, 2017.

(51) Int. Cl.
| | |
|---|---|
| *C07K 16/28* | (2006.01) |
| *A61K 39/00* | (2006.01) |
| *A61P 35/00* | (2006.01) |
| *C07K 14/705* | (2006.01) |
| *C07K 14/725* | (2006.01) |
| *A61K 35/17* | (2015.01) |
| *A61K 47/68* | (2017.01) |
| *C12N 5/0783* | (2010.01) |

(52) U.S. Cl.
CPC ........ *C07K 16/2863* (2013.01); *A61K 35/17* (2013.01); *A61K 39/001109* (2018.08); *A61K 47/6815* (2017.08); *A61K 47/6849* (2017.08); *A61P 35/00* (2018.01); *C07K 14/7051* (2013.01); *C07K 14/70517* (2013.01); *C07K 14/70521* (2013.01); *C07K 14/70578* (2013.01); *C12N 5/0636* (2013.01); *A61K 2039/5156* (2013.01); *C07K 2317/22* (2013.01); *C07K 2317/33* (2013.01); *C07K 2317/34* (2013.01); *C07K 2317/565* (2013.01); *C07K 2317/569* (2013.01); *C07K 2317/622* (2013.01); *C07K 2317/92* (2013.01); *C07K 2319/00* (2013.01); *C07K 2319/02* (2013.01); *C07K 2319/03* (2013.01); *C07K 2319/30* (2013.01); *C07K 2319/33* (2013.01); *C07K 2319/35* (2013.01); *C12N 2501/165* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 2015/0030597 A1* | 1/2015 | Rosenberg | ......... C07K 14/7051 424/134.1 |
| 2018/0243437 A1* | 8/2018 | Chao | ....................... A61P 35/00 |
| 2018/0244784 A1* | 8/2018 | Chao | ....................... A61P 35/00 |

FOREIGN PATENT DOCUMENTS

| | | | |
|---|---|---|---|
| CN | WO 2010/102518 | * | 3/2010 |
| WO | WO-2010102518 | | 9/2010 |
| WO | WO-2011041093 A1 | | 4/2011 |
| WO | WO 2014/186469 | * | 11/2014 |

OTHER PUBLICATIONS

Machine translation of Sun WO 2010/102518 (Year: 2010).*
Sircar et al. J Immunol. Jun. 1, 2011; 186(11): 6357-6367.*
"International Application No. PCT/CA2018/050004, International Search Report and Written Opinion dated Apr. 9, 18", (Apr. 9, 2018), 13 pgs.
Inoo, Kanako, et al., "Immunological quality and performance of tumor vessel-targeting CAR-T cells prepared by mRNA-EP for clinical research", Molecular Therapy—Oncolytics (2016), 3, 16047, (Nov. 16, 2016), 13 pas.
Tian, Baomin, et al., "Development and Characterization of a Camelid Single Domain Antibody—Urease Conjugate That Targets Vascular Endothelial Growth Factor Receptor 2". Front. Immunol. 8:956, (Aug. 21, 2017), 19 pgs.
Uger, Marni, et al., "CAR-T cell harboring a camelid single domain antibody as a target-ing agent to kill tumors expressing VEGFR2", Abstract, Proceedings of the American Association for Cancer Research, vol. 58, pp. 962-963 (Apr. 2017), (Apr. 2017), 962-963.
"European Application No. 18735964.1, Partial Supplementary European Search Report dated Jan. 22, 2021", (Jan. 22, 2021), 16 pgs.
Chao, Heman, et al., "#3770: CAR-T cell harboring a camelid single domain antibody as a targeting agent to kill tumors expressing VEGFR2", Proceedings of the American Association for Cancer Research, AACR 2017 Annual Meeting, vol. 58, (Apr. 1, 2017), 3 pgs.
Chao, Heman, et al., "Camelid single domain antibody application in cell based therapies—KW017-00037-2017-01", 9th International Conference of Contemporary Oncology: Genome Based Precision Immuno- and Targeted Therapy, Poznan, Mar. 22-24, 2017, (Mar. 24, 2017), 54 pgs.

(Continued)

*Primary Examiner* — James D Schultz
(74) *Attorney, Agent, or Firm* — Schwegman Lundberg & Woessner, P.A.

(57) ABSTRACT

Compositions and methods for treating cancer in humans are provided using CARs. The invention includes engineered CARs (chimeric receptor antigens) and genetically modified immune cells that express such a CAR with a high affinity for VEGFR. More specifically, the cells are CAR-T cells recognizing VEGFR-2 on solid tumors, uses thereof, compositions thereof and methods of making. The invention includes therapeutic methods to treat VEGFR-2 dependent cancers targeting tumor angiogenesis.
A chimeric antigen receptor (CAR) that binds to VEGFR-2, an epitope or fragment thereof, or a variant thereof.

25 Claims, 23 Drawing Sheets
(23 of 23 Drawing Sheet(s) Filed in Color)
Specification includes a Sequence Listing.

(56) References Cited

OTHER PUBLICATIONS

Chinnasamy, Dhanalakshmi, et al., "Gene therapy using genetically modified lymphocytes targeting VEGFR-2 inhibits the growth of vascularized syngenic tumors in mice", The Journal of Clinical Investigation, vol. 120, No. 11, (Nov. 1, 2010), 3953-3968.

Chinnasamy, Dhanalakshmi, et al., "Local Delivery of Interleukin-12 Using T Cells Targeting VEGF Receptor-2 Eradicates Multiple Vascularized Tumors in Mice", Clinical Cancer Research, vol. 18, No. 6, (Jan. 30, 2012), 1672-1683.

Kanagawa, N., et al., "Tumor vessel-injuring ability improves antitumor effect of cytotoxic T lymphocytes in adoptive immunotherapy", Cancer Gene Therapy, vol. 20, No. 1, (Jan. 1, 2013), 57-64.

"Japanese Application No. 2019-536567, Office Action dated Dec. 7, 2021", (Dec. 7, 2021), 14 pgs.

Jamnani, Fatemeh Rahimi, et al., "T Cells expressing VHH-directed oligoclonal chimeric X HER2 antigen receptors: Towards tumor-directed oligoclonal T cell therapy", Biochimica et Biophysica Acta (BBA), vol. 1840, issue 1, Jan. 2014, pp. 378-386, (Jan. 2014), 378-386 [with English abstract].

* cited by examiner

Restriction Digestion Map

Lane1: Lenti-EF1a-VHH-3rd-CAR-EGFRt-AT-Free Digested with EcoRI/BamHI

Lane M: DNA Marker DL10000

VEGFR-2 CAR IMMUNE CELLS TO TREAT CANCERS

CROSS-REFERENCE TO RELATED APPLICATION

This application is entitled to priority under 35 U.S.C. § 119(e) to U.S. Provisional patent application Ser. No. 62/442,649 filed on Jan. 5, 2017, U.S. Provisional Patent Application Ser. No. 62/480,712 filed on Apr. 3, 2017, U.S. Provisional Patent Application Ser. No. 62/491,643 filed on Apr. 28, 2017 and U.S. Provisional Patent Application Ser. No. 62/535,330 filed on Jul. 21, 2017, each of which application is hereby incorporated herein by reference in its entirety.

FIELD OF THE INVENTION

The present invention relates to cancer immunotherapy, more specifically compositions and methods for treating cancer in humans. The invention includes engineered CARs (chimeric receptor antigens) and genetically modified immune cells such as a CAR with a high affinity for VEGFR. More specifically, the cells are CAR-T cells recognizing VEGFR-2 on solid tumors, uses thereof, compositions thereof and methods of making. The invention includes therapeutic methods to treat VEGFR-2 dependent cancers targeting tumor angiogenesis.

BACKGROUND OF THE INVENTION

Modulation of the immune system is showing great promise in the treatment of malignancies. In addition to checkpoint inhibitors that re-activate T cells present in the tumor microenvironment, exogenously transduced chimeric antigen receptor (CAR)-T cells are providing hopeful responses in clinical trials for the treatment of leukemias.

Angiogenesis is the process of new blood vessel formation and is essential for a tumor to grow beyond a certain size. Angiogenesis facilitates the growth and metastasis of solid tumors. Tumors secrete the pro-angiogenic factor vascular endothelial growth factor (VEGF), which acts upon local endothelial cells by binding to vascular endothelial growth factor receptors (VEGFR).

Vascular endothelial growth factor, VEGF, is an endothelial cell-specific mitogen. It is distinct among growth factors in that it acts as an angiogenesis inducer by specifically promoting the proliferation of endothelial cells. The biological response of VEGF is mediated through its high affinity receptors, which are selectively expressed on endothelial cells during embryogenesis and during tumor formation. Vascular endothelial growth factors regulate vascular development, angiogenesis and lymphangiogenesis by binding to a number of receptors. VEGFR-1 is required for the recruitment of haematopoietic stem cells and the migration of monocytes and macrophages, VEGFR-2 regulates vascular endothelial function and VEGFR-3 regulates lymphatic endothelial cell function.

There is a need for compositions and methods of treating or preventing cancer that targets tumor angiogenesis. Such a need includes the treatment of solid tumors using CARs that recognize VEGFR-2 expressed on tumor cells with a desired clinical activity to help control tumor-associated angiogenesis and thus try to limit/decrease cancer progression/growth.

SUMMARY OF THE INVENTION

VEGFR-2 is expressed by a variety of tumors. Herein are described CARs and CAR-T cells that target VEGFR-2-expressing tumors. The anti-VEGFR-2 CARs and CAR-T cells herein provided have use to inhibit/decrease angiogenesis and induce tumor regression.

The present invention provides CARs engineered to target solid tumors. In one aspect, T cells are genetically engineered to produce CARs expressing proteins that allow the T cells to recognize a specific protein (antigen) on tumor cells. These engineered CAR-T cells are then grown in the laboratory before use for treatment. The CARs described herein have high affinity for solid tumors expressing VEGFR-2. In aspects, the CARs described herein have high affinity for VEGFR-2 dependent cancers. The unique specificity of the CARs described herein comes from the use of sdAbs (single domain antibodies) in place of the scFv of an engineered CAR. This provides a higher affinity due to the small size thereof. Such antibodies also have a propensity to refold easily and biophysical stability. In addition, they may recognize epitopes that are inaccessible to conventional antibodies and can be engineered.

In aspects of the invention is a human T cell comprising a nucleic acid sequence encoding a chimeric antigen receptor (CAR), wherein the CAR comprises a VEGFR-2 binding domain, wherein the CAR further comprises a transmembrane domain, a 4-1BB costimulatory signaling region, and a CD3 zeta signaling domain, wherein the T cells is from a human having cancer.

In aspects, the cancer expressing VEGFR-2 is treated.

In aspects described herein, the sdAbs for use in the CAR and CAR-T cells are camelid single domain antibodies specific for VEGFR-2. In aspects, the sdAbs are specific for VEGFR-2 as well as fragments or variants thereof.

The CAR constructs of the invention may comprise an isolated or purified antibody or fragment thereof that comprise one of the sequences of SEQ ID NO:2-30 with or without a linker sequence, in aspects the linker sequence may comprise a terminal cysteine, which in aspects is useful for chemical conjugation, or a sequence at least 85%, at least 86%, at least 87%, at least 88%, at least 89%, at least 90%, at least 91%, at least 92%, at least 93%, at least 94% or at least 95% identical thereto, or a sequence substantially identical thereto.

Linker sequences suitable for the single domain antibodies of the invention may be selected from the group consisting of SEQ ID NO:54-65. In aspects, the linker sequence may further comprise a C-terminal cysteine, for example as in SEQ ID NO:66-69. Sequences similar to these linker sequences may be used herein.

In aspects, there are provided immune cells that express the CARs described herein. The immune cells are typically T cells or CIK cells but can also be a Natural Killer (NK) cell, a cytotoxic T lymphocyte (CTL), and a regulatory T cell.

In aspects described herein, there are provided methods for making a CAR-T specific for VEGFR-2. In aspects, the methods may be viral or non-viral. More specifically, the methods in aspects are non-viral methods comprising transposons.

The present invention provides an isolated nucleic acid sequence encoding a chimeric antigen receptor (CAR), wherein the CAR comprises antigen binding domain that is a sdAb that binds to VEGFR-2 as well as variants, fragments and specific epitopes thereof, a transmembrane domain, one or more co-stimulatory signaling region, and a CD3 zeta signaling domain. In one aspect, the nucleic acid sequence encoding a CAR comprises the nucleic acid sequence of SEQ ID NO:79. In this non-limiting example the CAR comprises AB1 (SEQ ID NO:2).

In one aspect, the antigen binding domain in the CAR is an antibody or an antigen-binding fragment thereof. Typically, the antigen-binding fragment is a single domain antibody or fragment thereof.

In one aspect, the sdAb in the CAR binds to a solid tumor expressing VEGFR-2.

In one aspect, the co-stimulatory signaling region in the CAR comprises the intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

The invention also provides an isolated CAR comprising an antigen binding domain, a transmembrane domain, a co-stimulatory signaling region, and a CD3 zeta signaling domain.

The invention also provides a cell comprising a nucleic acid sequence encoding a CAR, wherein the CAR comprises an antigen binding domain, a transmembrane domain, a costimulatory signaling region, and a CD3 zeta signaling domain.

In one aspect, the immune cell comprising the CAR is selected from the group consisting of a T cell, a Natural Killer (NK) cell, a CIK cell, a cytotoxic T lymphocyte (CTL), and a regulatory T cell.

The invention also provides a vector comprising a nucleic acid sequence encoding a CAR, wherein the CAR comprises an antigen binding domain, a co-stimulatory signaling region, and a CD3 zeta signaling domain.

The invention also provides a method for reducing tumor growth in a mammal. In one aspect, the method comprises administering to a mammal an effective amount of a cell genetically modified to express a CAR wherein the CAR comprises an antigen binding domain, a co-stimulatory signaling region, and a CD3 zeta signaling domain, wherein the antigen binding domain is a sdAb that specifically recognizes VEGFR-2.

The invention also provides a method for reducing angiogenesis associated with a tumor in a mammal. In one aspect, the method comprises administering to a mammal an effective amount of a cell genetically modified to express a CAR wherein the CAR comprises an antigen binding domain, a co-stimulatory signaling region, and a CD3 zeta signaling domain, wherein the antigen binding domain is a sdAb that specifically recognizes VEGFR-2.

The invention also includes a method of treating a mammal having a tumor associated with an elevated expression of a VEGFR-2. In one aspect, the method comprises administering to a mammal an effective amount of a cell genetically modified to express a CAR wherein the CAR comprises sdAb specific for VEGFR-2, a co-stimulatory signaling region, and a CD3 zeta signaling domain, thereby treating the mammal.

In one aspect, the cell is an autologous T cell.

In another aspect, the cell is an allogeneic T cell.

The invention also includes a method of generating a persisting population of genetically engineered T cells in a human diagnosed with cancer. In one aspect, the method comprises administering to a human a T cell genetically engineered to express a CAR wherein the CAR comprises an antigen binding domain specific for VEGFR-2, a co-stimulatory signaling region, and a CD3 zeta signaling domain, wherein the persisting population of genetically engineered T cells persists in the human for at least one month after administration.

In one aspect, the persisting population of genetically engineered T cells comprises at least one cell selected from the group consisting of a T cell that was administered to the human, a progeny of a T cell that was administered to the human, and a combination thereof.

In one aspect, the persisting population of genetically engineered T cells comprises a memory T cell.

In one aspect, the persisting population of genetically engineered T cells persists in the human for at least three months after administration. In another aspect, the persisting population of genetically engineered T cells persists in the human for at least four months, five months, six months, seven months, eight months, nine months, ten months, eleven months, twelve months, two years, or three years after administration.

The invention also provides a method of expanding a population of genetically engineered T cells in a human diagnosed with cancer. In one aspect, the method comprises administering to a human a T cell genetically engineered to express a CAR wherein the CAR comprises a sdAb specific for VEGFR-2, a co-stimulatory signaling region, and a CD3 zeta signaling domain, wherein the administered genetically engineered T cell produces a population of progeny T cells in the human.

In one aspect, the progeny T cells in the human comprise a memory T cell.

In one aspect, the T cell is an autologous T cell or an allogeneic T cell.

In one aspect, the immune cell is a CIK cell, which can be autologous or allogeneic.

In another aspect, the human is resistant to at least one chemotherapeutic agent.

In one aspect, the cancer is any cancer that expresses VEGFR-2 as well as variants or epitopes thereof. Such cancers include but may not be limited to pancreas, breast, colorectal, lung, gastric, ovary and bladder.

In one aspect, the population of progeny T cells persists in the human for at least three months after administration. In another aspect, the population of progeny T cells persist in the human for at least four months, five months, six months, seven months, eight months, nine months, ten months, eleven months, twelve months, two years, or three years after administration.

In aspects of the invention is a chimeric antigen receptor (CAR) that binds to VEGFR-2, an epitope or fragment thereof, or a variant thereof. In further aspects are functional portions of the CAR of the invention which retain the biological activity of the CAR of which it is part.

In aspects, the CAR comprises a single domain antibody or a fragment thereof for binding to VEGFR-2. The single domain antibody may comprise a sequence selected from the group consisting of SEQ ID No:2-30.

In aspects, the single domain antibody or fragment thereof is a species of the family Camelidae.

In aspects, the CAR binds to an epitope of VEGFR-2. For example, but not limited to epitopes described in U.S. Pat. No. 8,378,071 (the disclosure of which is incorporated by reference herein in its entirety).

In aspects the CAR comprises a complementarity determining region (CDR) 1; a CDR2; and a CDR3 for binding to VEGFR-2.

In aspects the CAR comprises the amino acid sequence: [Signal peptide-VHH-CD8 hinge-CD28-4-1 BB-CD3zeta-T2A-EGFRt] which, in aspects, comprises or consists of SEQ ID NO:78 or a variant or fragment thereof, such as a sequence at least 90% identical thereto. The VHH sequence comprises AB1

(SEQ ID NO:2). A nucleic acid sequence encoding the CAR is represented by SEQ ID NO:79.

In aspects the CAR comprises a spacer molecule, a transmembrane region and one or more cell signaling domains selected from the group consisting of a human CD8-alpha protein, a human CD28 protein, a human CD3-zeta protein, a human FcRy protein, a CD27 protein, an OX40 protein, a human 4-IBB protein, modified versions of any of the foregoing, and any combination of the foregoing.

In aspects is an immune cell comprising a CAR as described herein. The cell may be a T cell or a cytokine induced killer (CIK) cell. In aspects the immune cell may further comprise at least a second CAR.

In aspects the immune cell comprises a transposon/transposase system that is optionally hyperactive. In aspects the transposon/transposase system is a Sleeping Beauty transposon/transposase system. In further aspects the transposon/transposase system is the SB100X transposon/transposase system.

In further aspects the CAR immune cell may further comprise a suicide gene.

In further aspects the CAR immune cell is provided as a composition comprising a pharmaceutically carrier, diluent, and/or excipient. The composition may be refrigerated, frozen or thawed.

In aspects of the invention is a nucleic acid molecule encoding a chimeric antigen receptor (CAR), wherein the CAR comprises a VEGFR-2 binding moiety and an immune cell activation moiety, wherein the VEGFR-2 binding moiety binds to VEGFR-2 or a variant or fragment thereof.

In aspects the VEGFR-2 binding moiety comprises a single domain monoclonal antibody or an antigen binding portion thereof directed against VEGFR-2 or a variant or fragment thereof. In aspects the VEGFR-2 binding moiety comprises a variable region of the monoclonal antibody.

In aspects the immune cell activation moiety comprises a T-cell signaling domain of any one or more of the following proteins: a human CD8-alpha protein, a human CD28 protein, a human CD3-zeta protein, a human FcRy protein, a CD27 protein, an OX40 protein, a human 4-IBB protein, and variants or fragments thereof.

In aspects is a nucleic acid molecule comprising a nucleotide sequence encoding one or both polypeptide chains of a chimeric antigen receptor (CAR), wherein the CAR comprises, in order from N-terminus to C-terminus:

i) an antigen-binding single domain antibody specific for VEGFR-2;
ii) a transmembrane domain;
iii) a costimulatory polypeptide, wherein the co-stimulatory polypeptide is a 4-1BB polypeptide and/or an OX-40 polypeptide; and
iv) an intracellular signaling domain.

In aspects the first polypeptide comprises a hinge region interposed between the single domain antibody and the transmembrane domain.

In aspects the hinge region is an immunoglobulin IgG hinge region or a hinge derived from CD8.

In aspects the intracellular signaling domain comprises an immunoreceptor tyrosine-based activation motif (ITAM).

In aspects the intracellular signaling domain comprising an ITAM is selected from CD3-zeta and ZAP70.

In aspects the nucleotide sequence is operably linked to a T-cell-specific promoter.

In aspects the nucleotide sequence is operably linked to an NK cell-specific promoter.

In aspects of the invention is a chimeric antigen receptor (CAR) encoded by the nucleic acid sequence as disclosed herein, in aspects the CAR is specific for VEGFR-2.

In aspects the CAR of the invention comprises the amino acid sequence of SEQ ID No:2-30 including fragments and variants thereof that retain the activity of binding to VEGFR-2

In aspects is a vector comprising the nucleic acid molecule as described herein. In aspects the nucleic acid molecule encodes the polypeptide of SEQ ID NO:78.

In aspects is a host cell expressing the nucleic acid molecule or the CAR as described herein, in aspects the host cell is an immune cell.

In aspects the host cell is selected from the group consisting of a T-cell and a cytokine induced killer CIK cell, and in aspects may further comprise at least a second CAR.

In aspects the host cell may further comprising a transposon/transposase system that is optionally hyperactive, in aspects the transposon/transposase system is the Sleeping Beauty transposon/transposase system. In further aspects the transposon/transposase system is the SB100X transposon/transposase system.

In aspects the host cell may further comprise a suicide gene.

In aspects is a population of cells comprising at least one host cell as described herein.

In aspects is a pharmaceutical composition comprising the immune cell or the host cell as described herein.

In aspects is a method of treating or preventing a VEGFR-2-expressing cancer in a mammal, the method comprising administering the immune cell or the host cell as described herein to the mammal in an amount effective to treat or prevent cancer in the mammal. In aspects the tumor is a solid tumor. In aspects the cancer is pancreatic cancer, breast cancer, colorectal cancer, lung cancer, gastric cancer, hepatocellular cancer, ovarian cancer or bladder cancer.

In aspects is a method for decreasing growth or reducing the size of a VEGFR-2-expressing tumor in a subject, where the method comprises administering a composition comprising a CAR-T specific for VEGFR-2.

In aspects is a method for decreasing angiogenesis in a VEGFR-2-expressing tumor in a subject, where the method comprises administering a composition comprising a CAR-T specific for VEGFR-2.

Further aspects of the invention are as follows:

According to an aspect of the invention is a chimeric antigen receptor (CAR) that binds to VEGFR-2, an epitope or fragment thereof, or a variant thereof.

According to a further aspect of the invention the CAR comprises a single domain antibody or a fragment thereof for binding to VEGFR-2.

According to an aspect of the invention the CAR comprises a single domain antibody or fragment thereof of a species of the family Camelidae.

According to an aspect of the invention the CAR binds to an epitope of VEGFR-2

According to an aspect of the invention the CAR binds to an epitope found in SEQ ID NO:1.

According to an aspect of the invention, the CAR comprises a complementarity determining region (CDR) 1; a CDR2; and/or a CDR3, wherein at least one of CDR1, CDR2 and CDR3 bind to VEGFR-2.

According to an aspect of the invention the CAR comprises the sequence of SEQ ID NO:78, or a sequence at least 90% identical thereto.

According to an aspect of the invention, the CAR further comprises a spacer molecule, a transmembrane region and one or more cell signaling domains selected from the group consisting of a human CD8-alpha protein, a human CD28 protein, a human CD3-zeta protein, a human FcRy protein, a CD27 protein, an OX40 protein, a human 4-1BB protein, modified versions of any of the foregoing, and any combination of the foregoing.

According to an aspect of the invention the CAR of the invention comprises a sequence selected from the group consisting of SEQ ID NO:2-30 or 31-53 and variants and fragments thereof or a sequence at least 85%, at least 86%, at least 87%, at least 88%, at least 89%, at least 90%, at least 91%, at least 92%, at least 93%, at least 94% or at least 95% identical thereto, or a sequence substantially identical thereto any one of SEQ ID NO:2-30 or SEQ ID NO:31-53.

According to an aspect of the invention, the CAR may further comprise a linker sequence selected from the group consisting of any one of SEQ ID NO:54-65 and variants thereof.

In aspects of the invention the CAR the linker sequence may further comprise a C-terminal cysteine, and in further aspects are selected from SEQ ID NO:66-69. Sequences similar to these linker sequences may be used herein. For example, KK is a suitable linker sequence and those comprising any one of the sequences of SEQ ID NO:54-69.

In aspects of the invention the linker sequence comprises GSEQKGGGEEDDGC (SEQ ID NO: 90) and variants thereof.

According to an aspect of the invention is an immune cell comprising the CAR as described herein.

According to an aspect of the invention the immune cell is a T cell or a cytokine induced killer (CIK) cell.

According to a further aspect of the invention, the immune cell, further comprises at least a second CAR.

In aspects of the invention the immune cell further comprises a transposon/transposase system that is optionally hyperactive. In aspects the transposon/transposase system is a Sleeping Beauty transposon/transposase system. In other aspects, the transposon/transposase system is the SB100X transposon/transposase system.

In aspects of the invention, the immune cell further comprises a suicide gene.

In aspects of the invention, the immune cell comprising the CAR of the invention is formulated into a composition comprising a pharmaceutically carrier, diluent, and/or excipient.

According to an aspect of the invention is a nucleic acid molecule encoding a chimeric antigen receptor (CAR), wherein the CAR comprises a VEGFR-2 binding moiety and an immune cell activation moiety, wherein the VEGFR-2 binding moiety binds to VEGFR-2 or a variant or fragment thereof.

In aspects of the invention, the VEGFR-2 binding moiety comprises a monoclonal antibody or an antigen binding portion thereof directed against VEGFR-2 or a variant or fragment thereof. In aspects, the VEGFR-2 binding moiety comprises a variable region of the monoclonal antibody.

According to an aspect of the invention the immune cell activation moiety comprises a T-cell signaling domain of any one or more of the following proteins: a human CD8-alpha protein, a human CD28 protein, a human CD3-zeta protein, a human FcRy protein, a CD27 protein, an OX40 protein, a human 4-IBB protein, and variants or fragments thereof.

According to an aspect of the invention the nucleic acid molecule comprises the nucleic acid sequence of at least one of SEQ ID NO:31-53 and/or which binds to the sequence of SEQ ID NO:1.

According to an aspect of the invention is a nucleic acid molecule comprising a nucleotide sequence encoding one or both polypeptide chains of a chimeric antigen receptor (CAR), wherein the CAR comprises, in order from N-terminus to C-terminus:

i) an antigen-binding single domain antibody specific for VEGFR-2;
ii) a transmembrane domain;
iii) a costimulatory polypeptide, wherein the co-stimulatory polypeptide is a 4-1BB polypeptide and/or an OX-40 polypeptide; and
iv) an intracellular signaling domain.

In aspects of the invention, the first polypeptide comprises a hinge region interposed between the single domain antibody and the transmembrane domain.

In aspects of the invention the hinge region is an immunoglobulin IgG hinge region or a hinge derived from CD8.

In aspects of the invention the intracellular signaling domain comprises an immunoreceptor tyrosine-based activation motif (ITAM).

In aspects of the invention, the intracellular signaling domain comprising an ITAM is selected from CD3-zeta and ZAP70.

In aspects of the invention, the nucleotide sequence is operably linked to a T-cell-specific promoter.

In aspects of the invention, the nucleotide sequence is operably linked to an NK cell-specific promoter.

In aspects of the invention, the nucleic acid molecule comprises SEQ ID NO:79.

In aspects of the invention is a chimeric antigen receptor (CAR) encoded by the nucleic acid sequence of SEQ ID NO:79.

In aspects of the invention, the CAR of the invention comprises the amino acid sequence of any one of SEQ ID Nos:2-30 and fragments and variants thereof.

In aspects of the invention is a vector comprising the nucleic acid molecule of any one of SEQ ID NO:31-53.

According to an aspect of the invention is a host cell expressing the nucleic acid molecule of SEQ ID NO:79 or the CAR of SEQ ID NO:78.

In aspects of the invention, the host cell is an immune cell. In aspects, the host cell is selected from the group consisting of a T-cell and a cytokine induced killer CIK cell.

In aspects of the invention the host cell further comprises at least a second CAR.

In aspects, the host cell of the invention further comprises a transposon/transposase system that is optionally hyperactive. In aspects, the transposon/transposase system is the Sleeping Beauty transposon/transposase system. In aspects, the transposon/transposase system is the SB100X transposon/transposase system.

In aspects of the invention, the host cell of the invention further comprises a suicide gene.

According to an aspect of the invention is a population of cells comprising at least one host cell of the invention comprising a CAR directed to VEGFR-2.

According to an aspect of the invention is a pharmaceutical composition comprising the host cell or immune cell comprising a CAR directed to VEGFR-2.

According to an aspect of the invention is a method of treating or preventing cancer in a mammal, the method comprising administering the immune cell or the host cell comprising a CAR directed to VEGFR-2 to the mammal in an amount effective to treat or prevent cancer in the mammal.

In aspects of the invention, the cancer is a VEGFR-2-expressing cancer.

In aspects of the invention, the cancer is a solid tumor.

According to an aspect of the invention is a method to reduce angiogenesis in a tumor, the method comprising administering the immune cell or the host cell comprising a CAR directed to VEGFR-2 to the mammal in an amount effective to reduce angiogenesis.

According to a further aspect of the invention is a CAR cassette having a structure comprising Signal peptide-VHH-CD8 hinge-CD28-4-1BB-CD3zeta-T2A-EGFRt and having a nucleic acid sequence of SEQ ID NO:79.

According to an aspect of the invention is a CAR cassette having a structure comprising Signal peptide-VHH-CD8 hinge-CD28-4-1BB-CD3zeta-T2A-EGFRt and an amino acid sequence of SEQ ID NO:78.

In aspects of the invention the CD8α transmembrane domain, the CD8αhinge domain, the 4-1BB costimulatory signaling region, and the CD3 zeta signaling domain may be encoded by nucleic acid sequences as shown in U.S. Pat. No. 9,518,123 (the disclosure of which is incorporated herein in its entirety).

According to an aspect of the invention is a human T cell comprising a nucleic acid sequence encoding a chimeric antigen receptor (CAR), wherein the CAR comprises a VEGFR-2 antigen binding domain, wherein the CAR further comprises a transmembrane domain, a 4-1BB costimulatory signaling region, and a CD3 zeta signaling domain, wherein the T cells is from a human having cancer. In aspects, the human T cell is isolated from a blood sample obtained from a human before the human is treated with a modality selected from the group consisting of an antiviral agent, chemotherapy, radiation, an immunosuppressive agent and an antibody. I

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of typical aspects described herein will be better understood when read in conjunction with the appended drawings. For the purpose of illustrating the invention, there are shown in the drawings aspects which are presently typical. It should be understood, however, that the invention is not limited to the precise arrangements and instrumentalities of the aspects shown in the drawings.

DETAILED DESCRIPTION OF THE INVENTION

Figure 1:
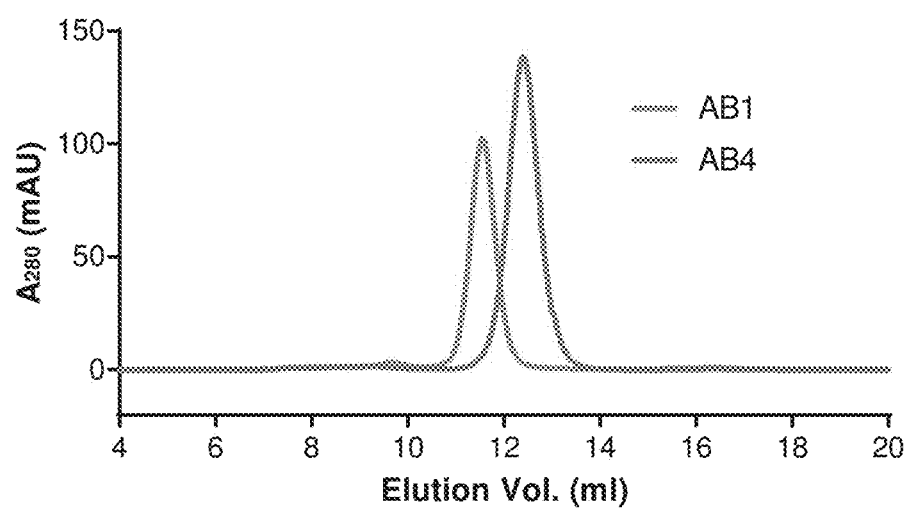
FIG. 1 shows size exclusion column chromatograms for AB1 (SEQ ID NO:2), AB2 (SEQ ID NO:11), AB3 (SEQ ID NO:19), and AB4 (SEQ ID NO:25).

The invention relates to compositions and methods for treating cancer such as solid tumors. The present invention incorporates adoptive cell transfer of T cells transduced to express a chimeric antigen receptor (CAR).

T cells are genetically modified to stably express a desired CAR that will target VEGFR-2, referred to herein as CAR T cells or CAR modified T cells. The cell is genetically modified to stably express a novel antibody binding domain as herein described on its surface, conferring novel antigen specificity to VEGFR-2.

In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution. With respect to the cytoplasmic domain, the CAR of the invention can be designed to comprise the CD28 and/or 4-1 BB signaling domain by itself or be combined with any other desired cytoplasmic domain(s) useful in the context of the CAR of the invention. In one embodiment, the cytoplasmic domain of the CAR can be designed to further comprise the signaling domain of CD3-zeta. For example, the cytoplasmic domain of the CAR can include but is not limited to CD3-zeta, 4-1BB and CD28 signaling modules and combinations thereof. Accordingly, the invention provides CAR T cells and methods of their use for adoptive therapy for treatment of VEGFR-2 expressing cancers.

In one embodiment, the CAR T cells of the invention can be generated by introducing a lentiviral vector comprising a desired CAR, for example a CAR comprising anti-VEGFR-2, CD8αhinge and transmembrane domain, and human 4-1BB and CD3zeta signaling domains, into the cells. The CAR T cells of the invention are able to replicate in vivo resulting in long-term persistence that can lead to sustained tumor control.

Further, the genetically modified T cells expressing a CAR for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded as known in the art and then infused back into the patient.

The invention includes using T cells expressing an anti-VEGFR-2 CAR which may comprise both CD3-zeta and the 4-1BB costimulatory domain (also referred to as CART/VEGFR-2 T cells). The CART/VEGFR-2 T cells of the invention can undergo robust in vivo T cell expansion.

Definitions

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Although any methods and materials similar or equivalent to those described herein can be used in the practice for testing of the present invention, the typical materials and methods are described herein. In describing and claiming the present invention, the following terminology will be used.

It is also to be understood that the terminology used herein is for the purpose of describing particular aspects only, and is not intended to be limiting.

In understanding the scope of the present application, the articles "a", "an", "the", and "said" are intended to mean that there are one or more of the elements.

Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation. In addition, all ranges given herein include the end of the ranges and also any intermediate range points, whether explicitly stated or not.

Terms of degree such as "substantially", "about" and "approximately" as used herein mean a reasonable amount of deviation of the modified term such that the end result is not significantly changed. These terms may refer to a measurable value such as an amount, a temporal duration, and the like, is meant to encompass variations of ±20% or ±10%, more typically ±5%, even more typically ±1%, and still more typically ±0.1% from the specified value, as such variations are appropriate to perform the disclosed methods.

"Activation", as used herein, refers to the state of an immune cell, such as a CIK cell or T cell, that has been sufficiently stimulated to induce detectable cellular proliferation. Activation can also be associated with induced cytokine production, and detectable effector functions. The term "activated T cells" refers to, among other things, T cells that are undergoing cell division.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example." The word "or" is intended to include "and" unless the context clearly indicates otherwise.

The term "antibody", also referred to in the art as "immunoglobulin" (Ig), used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure familiar to those of skill in the art.

The light and heavy chain variable regions are responsible for binding the target antigen and can therefore show significant sequence diversity between antibodies. The constant regions show less sequence diversity, and are responsible for binding a number of natural proteins to elicit important immunological events. The variable region of an antibody contains the antigen binding determinants of the molecule, and thus determines the specificity of an antibody for its target antigen. The majority of sequence variability occurs in six hypervariable regions, three each per variable heavy and light chain; the hypervariable regions combine to form the antigen-binding site, and contribute to binding and recognition of an antigenic determinant. The specificity and affinity of an antibody for its antigen is determined by the structure of the hypervariable regions, as well as their size, shape and chemistry of the surface they present to the antigen. Various schemes exist for identification of the regions of hypervariability, the two most common being those of Kabat and of Chothia and Lesk. Kabat et al (1991a; 1991b) define the "complementarity-determining regions" (CDR) based on sequence variability at the antigen-binding regions of the VH and VL domains. Chothia and Lesk (1987) define the "hypervariable loops" (H or L) based on the location of the structural loop regions in the VH and VL domains. As these individual schemes define CDR and hypervariable loop regions that are adjacent or overlapping, those of skill in the antibody art often utilize the terms "CDR" and "hypervariable loop" interchangeably, and they may be so used herein. For this reason, the regions forming the antigen-binding site are referred to as CDR L1, CDR L2, CDR L3, CDR H1, CDR H2, CDR H3 in the case of antibodies comprising a VH and a VL domain; or as CDR1, CDR2, CDR3 in the case of the antigen-binding regions of either a heavy chain or a light chain. The CDR/loops are referred to herein according to the IMGT numbering system (Lefranc et al., 2003), which was developed to facilitate comparison of variable domains. In this system, conserved amino acids (such as Cys23, Trp41, Cys 104, Phe/Trp 118, and a hydrophobic residue at position 89) always have the same position. Additionally, a standardized delimitation of the framework regions (FR1: positions 1 to 26; FR2: 39 to 55; FR3: 66 to 104; and FR4: 118 to 128) and of the CDR (CDR1: 27 to 38, CDR2: 56 to 65: and CDR3: 105 to 117) is provided.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, single-chain Fv (scFv; a molecule consisting of VL and VH connected with a peptide linker), Fab, F(ab')2, single domain antibody (sdAb; a fragment composed of a single VL or VH), and multivalent presentations of any of these. Antibody fragments of any one of SEQ ID NO:2-30 are those understood by one of skill in the art to retain biological activity to bind to VEGFR-2.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

In a non-limiting example, the antibody fragment may be an sdAb derived from naturally-occurring sources. Heavy chain antibodies of camelid origin (Hamers-Casterman et al, 1993) lack light chains and thus their antigen binding sites consist of one domain, termed $V_{HH}$. sdAb have also been observed in shark and are termed $V_{NAR}$ (Nuttall et al, 2003). Other sdAb may be engineered based on human Ig heavy and light chain sequences (Jespers et al, 2004; To et al, 2005). As used herein, the term "sdAb" includes those sdAb directly isolated from $V_H$, $V_{HH}$, $V_L$, or $V_{NAR}$ reservoir of any origin through phage display or other technologies, sdAb derived from the aforementioned sdAb, recombinantly produced sdAb, as well as those sdAb generated through further modification of such sdAb by humanization, affinity maturation, stabilization, solubilization, e.g., camelization, or other methods of antibody engineering. Also encompassed by the present invention are homologues, derivatives, or fragments that retain the antigen-binding function and specificity of the sdAb.

SdAbs have high thermostability, high detergent resistance, relatively high resistance to proteases (Dumoulin et al, 2002) and high production yield (Arbabi-Ghahroudi et al, 1997); they can also be engineered to have very high affinity by isolation from an immune library (Li et al, 2009) or by in vitro affinity maturation (Davies & Riechmann, 1996).

A person of skill in the art would be well-acquainted with the structure of a single-domain antibody (see, for example, 3DWT, 2P42 in Protein Data Bank). A sdAb comprises a single immunoglobulin domain that retains the immunoglobulin fold; most notably, only three CDR form the antigen-binding site. However, and as would be understood by those of skill in the art, not all CDR may be required for binding the antigen. For example, and without wishing to be limiting, one, two, or three of the CDR may contribute to binding and recognition of the antigen by the sdAb of the present invention. The CDR of the sdAb or variable domain are referred to herein as CDR1, CDR2, and CDR3, and numbered as defined by Kabat et al (1991b).

Epitope: An antigenic determinant. An epitope is the particular chemical groups or peptide sequences on a molecule that are antigenic, that is, that elicit a specific immune response. An antibody specifically binds a particular antigenic epitope, e.g., on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996). In one embodiment, an epitope binds an MHC molecule, such an HLA molecule or a DR molecule. These molecules bind polypeptides having the correct anchor amino acids separated by about eight to about ten amino acids, such as nine amino acids.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be synthesized or can be derived from a biological sample. Such a biological sample can include, but is not limited to a tissue sample, a tumor sample, a cell or a biological fluid.

The term "anti-tumor effect" or "treatment of cancer" as used herein, refers to a biological effect which can be manifested by a decrease in tumor volume, a decrease in the number of tumor cells, a decrease in the rate of tumor growth, a decrease in the number of metastases, stabilized disease, an increase in life expectancy, or amelioration of various physiological symptoms associated with the cancerous condition. An "anti-tumor effect" can also be manifested by the ability of the peptides, polynucleotides, cells and antibodies described herein in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from a different species.

"Syngeneic" refers to a graft derived from an identical individual.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e g, naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared-.times.100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

A "transposon" or "transposable element" is a DNA sequence that can change its position within a genome, sometimes creating or reversing mutations and altering the cell's genome size. Transposition often results in duplication of the transposon. There are two distinct types of transposon: class II transposons, which consist of DNA that moves directly from place to place; and class I transposons, which are retrotransposons that first transcribe the DNA into RNA and then use reverse transcriptase to make a DNA copy of the RNA to insert in a new location. Transposons typically interact with a transposase, which mediates the movement of the transposon. Non-limiting examples of transposon/transposase systems include Sleeping Beauty, Piggybac, Frog Prince, and Prince Charming.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, typically, a human.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds." as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a super agonist anti-CD28 antibody, and a super agonist anti-CD2 antibody.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

As used herein "treatment" or "therapy" is an approach for obtaining beneficial or desired clinical results. For the purposes described herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of a disease or disorder such as cancer, or may render the cells more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat cancer. Effective amounts of the compounds described herein may vary according to factors such as the disease state, age, sex, and weight of the subject. Dosage or treatment regimes may be adjusted to provide the optimum therapeutic response, as is understood by a skilled person. For example, administration of a therapeutically effective amount of an anti-VEGFR-2 sdAb is, in aspects, sufficient to reduce, inhibit or prevent formation of blood vessels associated with tumor progression or metastasis.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The antibodies described herein may, in aspects, be administered before, during or after treatment with conventional therapies for the disease or disorder in question, such as cancer.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The terms "patient," "subject." "individual," and the like are used interchangeably herein, and refer to any animal, or cells thereof whether in vitro or in situ, amenable to the methods described herein.

Moreover, the terms "patient", "subject" and "individual" includes living organisms in which an immune response can be elicited (e.g., mammals). In certain non-limiting aspects, the patient, subject or individual is a mammal and includes humans, dogs, cats, mice, rats, and transgenic species thereof. The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

Administration "in combination with" one or more further therapeutic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, isotonic and/or absorption delaying agents and the like. The use of pharmaceutically acceptable carriers is well known.

Isolated: An "isolated" biological component (such as a protein) has been substantially separated or purified away from other biological components in the cell of the organism in which the component naturally occurs, i.e., chromosomal and extra-chromosomal DNA and RNA, other proteins and organelles. Proteins and peptides that have been "isolated" include proteins and peptides purified by standard purification methods. The term also includes proteins and peptides prepared by recombinant expression in a host cell, as well as chemically synthesized proteins and peptides.

"Tumour", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. As used herein, cancer or cancerous is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The cancer to be treated may be any type of malignancy and, in an aspect, is lung cancer, including small cell lung cancer and non-small cell lung cancer (e.g. adenocarcinoma), pancreatic cancer, colon cancer (e.g. colorectal carcinoma, such as, for example, colon adenocarcinoma and colon adenoma), oesophageal cancer, oral squamous carcinoma, tongue carcinoma, gastric carcinoma, liver cancer, nasopharyngeal cancer, hematopoietic tumours of lymphoid lineage (e.g. acute lymphocytic leukemia, B-cell lymphoma, Burkitt's lymphoma, non-Hodgkin's lymphoma (e.g. mantle cell lymphoma), Hodgkin's disease, myeloid leukemia (for example, acute myelogenous leukemia (AML) or chronic myelogenous leukemia (CML)), acute lymphoblastic leukemia, chronic lymphocytic leukemia (CLL), thyroid follicular cancer, myelodysplastic syndrome (MDS), tumours of mesenchymal origin, soft tissue sarcoma, liposarcoma, gastrointestinal stromal sarcoma, malignant peripheral nerve sheath tumour (MPNST), Ewing sarcoma, leiomyosarcoma, mesenchymal chondrosarcoma, lymphosarcoma, fibrosarcoma, rhabdomyosarcoma, melanoma, teratocarcinoma, neuroblastoma, brain tumours, medulloblastoma, glioma, benign tumour of the skin (e.g. keratoacanthoma), breast carcinoma (e.g. advanced breast cancer), kidney carcinoma, nephroblastoma, ovary carcinoma, cervical carcinoma, endometrial carcinoma, bladder carcinoma, prostate cancer, including advanced disease and hormone refractory prostate cancer, testicular cancer, osteosarcoma, head and neck cancer, epidermal carcinoma, multiple myeloma (e.g. refractory multiple myeloma), or mesothelioma. In an aspect, the cancer cells are derived from a solid tumour. Typically, the cancer cells are derived from a breast cancer, colorectal cancer, melanoma, ovarian cancer, pancreatic cancer, gastric cancer, lung cancer, or prostate cancer. More typically, the cancer cells are derived from a prostate cancer, a lung cancer, a breast cancer, or a melanoma.

A "chemotherapeutic agent" is a chemical compound useful in the treatment of cancer. Examples of chemotherapeutic agents include alkylating agents such as thiotepa, CYTOXAN™ cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins such as bullatacin and bullatacinone; camptothecins such as topotecan; bryostatin; callystatin; CC-1065 and its adozelesin, carzelesin and bizelesin synthetic analogues; cryptophycins such as cryptophycin 1 and cryptophycin 8; dolastatin; duocarmycins such as the synthetic analogues KW-2189 and CB1-TM1; eleutherobin; pancratistatin; sarcodictyins; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics, for example calicheamicin, especially calicheamicin gamma1I and calicheamicin omega11, dynemicin, including dynemicin A, bisphosphonates, such as clodronate, esperamicins, neocarzinostatin chromophore and related chromoprotein enediyne antibiotic chromophores; aclacinomysins; actinomycin; authramycin; azaserine; bleomycins; cactinomycin; carabicin; carminomycin; carzinophilin; chromomycins; dactinomycin; daunorubicin; detorubicin; 6-diazo-5-oxo-L-norleucine; ADRIAMYCIN™ doxorubicin, including morpholino-doxorubicin, cyanomorpholino-doxorubicin, 2-pyrrolino-doxorubicin and deoxydoxorubicin; epirubicin; esorubicin; idarubicin; marcellomycin; mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilones; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex; razoxane; rhizoxin; sizofiran; spirogermanium; Lenuazonic acid; triaziquone; 2,2',2"-trichlorotriethylamine; trichothecenes such as T-2 toxin, verracurin A, roridin A and anguidine; urethan; vindesine; dacarbazine; mannomustine; mitobronitol; mitolactol; pipobroman; gacytosine; arabinoside ("Ara-C"); taxoids, such as TAXOL™ paclitaxel, ABRAXANE™ Cremophor-free, albumin-engineered nanoparticle formulation of paclitaxel, TAXOTERE™ and doxetaxel; chloranbucil; GEMZAR™ gemcitabine; 6-thioguanine; mercaptopurine; methotrexate; platinum coordination complexes such as cisplatin, oxaliplatin and carboplatin; vinblastine; platinum; etoposide (VP-16); ifosfamide; vincristine; NAVELBINE™ vinorelbine; novantrone; teniposide; edatrexate; daunomycin; aminopterin; xeloda; ibandronate; irinotecans such as CPT-11; topoisomerase inhibitors such as RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumours such as anti-estrogens and selective estrogen receptor modulators (SERMs), including, for example, tamoxifen (including NOLVADEX™ tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE™ megestrol acetate, AROMASIN™ exemestane, formestane, fadrozole, RIVISOR™ vorozole, FEMARA™ letrozole, and ARIMIDEX™ anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signalling pathways implicated in aberrant cell proliferation, such as, for example, PKC-alpha, Ralf and H-Ras; ribozymes such as a VEGF expression inhibitor (e.g., ANGIOZYME™ ribozyme) and a HER2 expression inhibitor; antibodies such as an anti-VEGF antibody (e.g., AVASTIN™ antibody); vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; and pharmaceutically acceptable salts, acids or derivatives of any of the above.

In aspects, the antibodies described herein act additively or synergistically with other conventional anti-cancer treatments.

"Variants" are biologically active antibodies or fragments thereof having an amino acid sequence that differs from the sequence of an anti-VEGFR-2 sdAb, such as those set out in SEQ ID NO:2-53, by virtue of an insertion, deletion, modification and/or substitution of one or more amino acid residues within the comparative sequence. Variants generally have less than 100% sequence identity with the comparative sequence. Ordinarily, however, a biologically active variant will have an amino acid sequence with at least about 70% amino acid sequence identity with the comparative sequence, such as at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity. The variants include peptide fragments of at least 10 amino acids that retain VEGFR-2 binding ability. Variants also include polypeptides wherein one or more amino acid residues are added at the N- or C-terminus of, or within, the comparative sequence. For example "MQV" at the N-terminal end can be substituted with "MKKQV" and still retain binding activity to VEGFR-2. Variants also include polypeptides where a number of amino acid residues are deleted and optionally substituted by one or more amino acid residues. Variants also may be covalently modified, for example by substitution with a moiety other than a naturally occurring amino acid or by modifying an amino acid residue to produce a non-naturally occurring amino acid.

"Percent amino acid sequence identity" is defined herein as the percentage of amino acid residues in the candidate sequence that are identical with the residues in the sequence of interest, such as the polypeptides of the invention, after aligning the sequences and introducing gaps, if necessary, to achieve the maximum percent sequence identity, and not considering any conservative substitutions as part of the sequence identity. None of N-terminal, C-terminal, or internal extensions, deletions or insertions into the candidate sequence shall be construed as affecting sequence identity or homology. Methods and computer programs for the alignment are well known in the art, such as "BLAST".

"Active" or "activity" for the purposes herein refers to a biological and/or an immunological activity of the sdAbs described herein, wherein "biological" activity refers to a biological function (either inhibitory or stimulatory) caused by a the sdAbs.

Thus, "biologically active" or "biological activity" when used in conjunction with "anti-VEGFR-2 sdAbs" means an anti-VEGFR-2 sdAb or fragment thereof that exhibits or shares an effector function of anti-VEGFR-2 antibodies. One biological activity of such an antibody is its ability to inhibit, at least in part, vascular formation.

The terms "inhibit" or "inhibitory" mean that a function or activity of VEGFR-2 is decreased, limited, blocked, or neutralized. These terms encompass a complete or partial inhibition in VEGFR-2 function or activity.

As used herein, an "anti-VEGFR-2 single domain antibody" includes modifications of an anti-VEGFR-2 antibody of the present invention that retains specificity for VEGFR-2. Such modifications include, but are not limited to, conjugation to an effector molecule such as a chemotherapeutic agent (e.g., cisplatin, taxol, doxorubicin) or cytotoxin (e.g., a protein, or a non-protein organic chemotherapeutic agent). Modifications further include, but are not limited to conjugation to detectable reporter moieties. Modifications that extend antibody half-life (e.g., pegylation) are also included. Proteins and non-protein agents may be conjugated to the antibodies by methods that are known in the art. Conjugation methods include direct linkage, linkage via covalently attached linkers, and specific binding pair members (e.g., avidin-biotin). Such methods include, for example, that described by Greenfield et al., Cancer Research 50, 6600-6607 (1990), which is incorporated by reference herein, for the conjugation of doxorubicin and those described by Amon et al., Adv. Exp. Med. Biol. 303, 79-90 (1991) and by Kiseleva et al, MoI. Biol. (USSR)25, 508-514 (1991), both of which are incorporated by reference herein.

The antibody or fragment thereof of the present invention is specific for VEGFR-2 whose expression is elevated in many solid tumors such as but not limited to breast, pancreatic, ovarian, lung and colon cancer.

The sequence of VEGFR-2 (also known as KDR D1-7, sKDR D1-7, Kinase insert domain receptor, Protein-tyrosine kinase receptor Flk-1, CD309, type III receptor tyrosine kinase. FLK1) may be, but is not limited to the sequence of SEQ ID NO: 1:

```
MQSKVLLAVA LWLCVETRAA SVGLPSVSLD LPRLSIQKDI

LTIKANTTLQ ITCRGQRDLD WLWPNNQSGS EQRVEVTECS

DGLFCKTLTI PKVIGNDTGA YKCFYRETDL ASVIYVYVQD

YRSPFIASVS DQHGVVYITE NKNKTVVIPC LGSISNLNVS

LCARYPEKRF VPDGNRISWD SKKGFTIPSY MISYAGMVFC

EAKINDESYQ SIMYIVVVG YRIYDVVLSP SHGIELSVGE

KLVLNCIART ELNVGIDFNW EYPSSKHQHK KLVNRDLKTQ

SGSEMKKFLS ILTIDGVTRS DQGLYTCAAS SGLMTKKNST

FVRVHEKPFV AFGSGMESLV EATVGERVRI PAKYLYPPPP

EIKWYKNGIP LESNHTIKAG HVLTIMEVSE RDTGNYTVIL

TNPISKEKQS HVVSLVVYVP PQIGEKSLIS PVDSYQYGTT

QTLTCTVYAI PPPHHIHWYW QLEEECANEP SQAVSVTNPY

PCEEWRSVED FQGGNKIEVN KNQFALIEGK NKTVSTLVIQ
```

-continued

```
AANVSALYKC EAVNKVGRGE RVISFHVTRG PEITLQPDMQ

PTEQESVSLW CTADRSTFEN LTWYKLGPQP LPIHVGELPT

PVCKNLDTLW KLNATMFSNS TNDILIMELK NASLQDQGDY

VCLAQDRKTK KRHCVVRQLT VLERVAPTIT GNLENQTTSI

GESIEVSCTA SGNPPPQIMW FKDNETLVED SGIVLKDGNR

NLTIRRVRKE DEGLYTCQAC SVLGCAKVEA FFIIEGAQEK

TNLEIIILVG TAVIAMFFWL LLVIILRTVK RANGGELKTG

YLSIVMDPDE LPLDEHCERL PYDASKWEFP RDRLKLGKPL

GRGAFGQVIE ADAFGIDKTA TCRTVAVKML KEGATHSEHR

ALMSELKILI HIGHHLNVVN LLGACTKPGG PLMVIVEFCK

FGNLSTYLRS KRNEFVPYKT KGARFRQGKD YVGAIPVDLK

RRLDSIISSQ SSASSGFVEE KSLSDVEEEE APEDLYKDFL

TLEHLICYSF QVAKGMEFLA SRKCIHRDLA ARNILLSEKN

VVKICDFGLA RDIYKDPDYV RKGDARLPLK WMAPETIFDR

VYTIQSDVWS FGVLLWEIFS LGASPYPGVK IDEEFCRRLK

EGTRMRAPDY TIPEMYQTML DCWHGERSQR PTFSELVEHL

GNLLQANAQQ DGKDYIVLPI SETLSMEEDS GLSLPTSPVS

CMEEEEVCDP KFHYDNTAGI SQYLQNSKRK SRPVSVKTFE

DIPLEEPEVK VIPDDNQTDS GMVLASEELK TLEDRTKLSP

SFGGMVPSKS RESVASEGSN QTSGYQSGYH SDDTDTTVYS

SEEAELLKLI EIGVQTGSTA QILQPDSGTT LSSPPV.
```

Ranges: throughout this disclosure, various aspects described herein can be presented in a range format. It should be understood that the description in range format is merely for convenience and brevity and should not be construed as an inflexible limitation on the scope described herein. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Many patent applications, patents, and publications are referred to herein to assist in understanding the aspects described. Each of these references are incorporated herein by reference in their entirety.

The invention relates to compositions and methods for treating cancer, in aspects solid tumors expressing VEGFR-2. The present invention relates to a strategy of adoptive cell transfer of immune cells transduced to express a chimeric antigen receptor (CAR). CARs are molecules that combine antibody-based specificity for a desired antigen (e.g., tumor antigen) with a T cell receptor-activating intracellular domain to generate a chimeric protein that exhibits a specific anti-tumor cellular immune activity. The gene-modified T cell therapy comprises introducing a nucleic acid encoding a chimeric antigen receptor (CAR) into a T cell, wherein the CAR has specificity for a surface antigen of a tumor cell and ability to activate a T cell, growing ex vivo the gene-introduced T cell thus obtained, and then transfusing the cell into a patient.

The present invention relates generally to the use of such T cells genetically modified to stably express a CAR specific for solid tumors expressing VEGFR-2, fragments, and/or epitopes thereof and variants of these. T cells expressing a CAR are referred to herein as CAR-T cells or CAR modified T cells. In aspects of the present invention, the T cell is genetically modified to stably express a CAR that combines an antigen recognition domain of a sdAb specific for VEGFR-2 with one or more intracellular costimulatory domains and signalling domains into a single chimeric protein.

Chimeric Antigen Receptor (CAR)

The CARs of the invention have specificity for vascular endothelial growth factor receptor-2 (VEGFR-2) (also known as kinase domain region (KDR) in humans and fetal liver kinase-1 (Flk-1) in mice). VEGFR-2 is a receptor for vascular endothelial growth factor (VEGF), has seven extracellular domains, and is selectively expressed by vascular endothelial cells. VEGFR-2 is overexpressed by tumor endothelial cells in tumor blood vessels. VEGFR-2 additionally can be expressed by normal, non-tumor, or non-cancerous cells. However, in such a situation, the expression of VEGFR-2 by normal, non-tumor, or non-cancerous cells is not as robust as the expression by tumor or cancer cells. In this regard, the tumor or cancer cells can over-express VEGFR-2 or express VEGFR-2 at a significantly higher level, as compared to the expression of VEGFR-2 by normal, non-tumor, or non-cancerous cells. VEGFR-2 enhances tumor vascularization, growth, and metastasis. Without being bound to a particular theory, it is believed that by binding VEGFR-2, the CAR-T target and destroy VEGFR-2 expressing endothelial cells in the tumor vasculature, attack tumor vasculature, reduce or eliminate tumors, facilitate infiltration of immune cells to the tumor site, and enhance/extend anti-tumor responses.

Anti-angiogenic tumor therapy provides many advantages. For example, because endothelial cells are genetically stable, drug resistance is believed to be unlikely. Additionally, the bloodstream provides easy access to the vascular endothelium and side effects and toxicity to normal tissues is believed to be limited. Moreover, the destruction of tumor blood vessels is believed to accelerate tumor cell death. Angiogenic endothelial cells are also believed to homogenously up-regulate antigen, e.g., VEGFR-2 expression. Moreover, anti-angiogenic tumor therapy is applicable to solid tumors that include a vascular supply.

In one aspect, engineered CARs are described herein.

In a specific, non-limiting example, the CAR described herein comprises a single domain anti-VEGFR-2 antibody which may comprise any one of the following sequences (note that sequences are also defined by their internal designations, e.g., AB1, V21, etc. in addition to their SEQ ID NO. These designations are used interchangeably herein, however, the SEQ ID NO should be considered the overriding definition if there is any question as to which sequence is being identified).

-AB1; V21, CDRs are underlined

SEQ ID NO: 2
```
MQVQLVESGG GLVQAGGSLR LSCAASGRAF SSYAMGWFRQ

APGKERELVA AISWSDDSTY YANSVKGRFT ISRDNAKSAV

YLQMNSLKPE DTAVYYCAAH KSLQRPDEYT YWGQGTQVTV SS
```

-V21H1; residues in bold are putative
locations for attachment to urease

SEQ ID NO: 3
MQVQLVESGG GLVQAGGSLR LSCAASGRAF SSYAMGWFRQ

APGKERELVA AISWSDDSTY YANSVKGRFT ISRDNAKSAV

YLQMNSLKPE DTAVYYCAAH KSLQRPDEYT YWGQGTQVTV

SSGSEEEDDD GKK

-AB1 with linker; V21H2

SEQ ID NO: 4
MQVQLVESGG GLVQAGGSLR LSCAASGRAF SSYAMGWFRQ

APGKEPELVA AISWSDDSTY YANSVKGRFT ISRDNAKSAV

YLQMNSLKPE DTAVYYCAAH KSLQRPDEYT YWGQGTQVTV

SSGSEQKGGG EEDDG

-AB1m-2 with linker; V21H3

SEQ ID NO: 5
MKAIFVLKGS LDRDPEFDDE GGGQVQLVES GGGLVQAGGS

LRLSCAASGR AFSSYAMGWF RQAPGKEREL VAAISWSDDS

TYYANSVKGR FTISRDNAKS AVYLQMNSLK PEDTAVYYCA

AHKSLQRPDE YTYWGQGTQV TVSSGSEQ

-AB1C; V21H4

SEQ ID NO: 6
MQVQLVESGG GLVQAGGSLR LSCAASGRAF SSYAMGWFRQ

APGKERELVA AISWSDDSTY YANSVKGRFT ISRDNAKSAV

YLQMNSLKPE DTAVYYCAAH KSLQRPDEYT YWGQGTQVTV

SSGSEQKGGG EEDDGC

-AB1 with linker 2; VR2-21

SEQ ID NO: 7
MQVQLVESGG GLVQAGGSLR LSCAASGRAF SSYAMGWERQ

APGKERELVA AISWSDDSTY TANSVKGRFT ISRDNAKSAV

YLQMNSLKPE DTAVYTCAAH KSLQRPDEYT TWGQGTQVTV

SSGSEQKLIS EEDLNHHHHH H

-AB1m

SEQ ID NO: 8
MKKQVQLVES GGGLVQAGGS LRLSCAASGR AFSSYAMGWF

RQAPGKEREL VAAISWSDDS TYYANSVKGR FTISRDNAKS

AVYLQMNSLK PEDTAVYYCA AHKSLQRPDE YTYWGQGTQV TVSS

-AB1m with linker; V21N2K

SEQ ID NO: 9
MKKQVQLVES GGGLVQAGGS LRLSCAASGR AFSSYAMGWF

RQAPGKEREL VAAISWSDDS TYYANSVKGR fTISRDNAKS

AVYLQMNSLK PEDTAVYYCA AHKSLQRPDE YTYWGQGTQV

TVSSGSEEED DDG

-AB1m-2

SEQ ID NO: 10
MKAIFVLKGS LDRDPEFDDE GGGQVQLVES GGGLVQAGGS

LRLSCAASGR AFSSYAMGWF RQAPGKEREL VAAISWSDDS

TYYANSVKGR FTISRDNAKS AVYLQMNSLK PEDTAVYYCA

AHKSLQRPDE YTYWGQGTQV TVSS

-AB2; V18

SEQ ID NO: 11
MQVQLVESGG GLIKPGGSLR LSCAASGFRF SAESMTWVRQ

APGKGLEWVS AISSSGGSTY YADSVKGRFT ISRDNSKNTV

YLQMNSLRAE DTAVYYCVRS PKGTIHASCS WNSGSWGQGT LVTVSS

-AB2 with linker

SEQ ID NO: 12
MQVQLVESGG GLIKPGGSLR LSCAASGFRF SAESMTWVRQ

APGKGLEWVS AISSSGGSTY YADSVKGRFT ISRDNSKNTV

YLQMNSLRAE DTAVYYCVRS PKGCTHASCS WNSGSWGQGT

LVTVSSGSEE DDDEEK

-AB2 with linker 2; VR2-801-18

SEQ ID NO: 13
MQVQLVESGG GLIKPGGSLR LSCAASGFRF SAESMTWVRQ

APGKGLEWVS AISSSGGSTY YADSVKGRFT ISRDNSKNTV

YLQMNSLRAE DTAVYYCVRS PKGCTHASCS WNSGSVGQGT

LVTVSSGSEQ KLISEEDLNH HHHH

-V18H3

SEQ ID NO: 14
MQVQLVESGG GLIKPGGSLR LSCAASGFRF SAESMTWVRQ

APGKGLEWVS AISSSGGSTY YADSVKGRFT ISRDNSKNTV

YLQMNSLRAE DTAVYYCVRS PKGCTHASCS WNSGSWGQGT

LVTVSSGSEQ KLISEEDLNG GGEDDEEGC

-AB2m

SEQ ID NO: 15
QVQLVESGGG LIKPGGSLRL SCAASGFRFS AESMTWVRQA

PGKGLEWVSA ISSSGGSTYY ADSVKGRFTI SRDNSKNTVY

LQMNSLRAED TAVYYCVRSP KGCTHASCSW NSGSWGQGTL VTVSS

-AB2m with linker

SEQ ID NO: 16
QVQLVESGGG LIKPGGSLRL SCAASGFRFS AESMTWVRQA

PGKGLEWVSA ISSSGGSTYY ADSVKGRFTI SRDNSKNTVY

LQMNSLRAED TAVYYCVRSP KGCTHASCSW NSGSWGQGTL

VTVSSGSEQK LISEEDLNHH HHH

-AB2m-2

SEQ ID NO: 17
MKAIFVLKGS LDRDPEFDDE EGGGQVQLVE SGGGLIKPGG

SLRLSCAASG FRFSAESMTW VRQAPGKGLE WVSAISSSGG

STYYADSVKG RFTISRDNSK NTVYLQMNSL RAEDTAVYYC

VRSPKGCTHA SCSWNSGSWG QGTLVTVSS

-AB2m-2 with linker; V18H2

SEQ ID NO: 18
MKAIFVLKGS LDRDPEFDDE EGGGQVQLVE SGGGLIKPGG

SLRLSCAASG FRFSAESMTW VRQAPGKGLE WVSAISSSGG

STYYADSVKG RFTISRDNSK NTVYLQMNSL RAEDTAVYYC

VRSPKGCTHA SCSWNSGSWG QGTLVTVSSG SDEE

-AB3; V45

SEQ ID NO: 19

MQVQLVESGG GLIKPGGSLR LSCAASGDML SYDVMSWVRQ

APGKGLEWVS AISSSGGSTY YADSVKGRFT ISRDNSKNTV

YLQMNSLRAE DTAVYYCVAA PWRCTHDNCS KTRASWGQGT MVTVSS

-AB3 with linker; V45H1

SEQ ID NO: 20

MQVQLVESGG GLIKPGGSLR LSCAASGDML SYDVMSWVRQ

APGKGLEWVS AISSSGGSTY YADSVKGRFT ISRDNSKNTV

YLQMNSLRAE DTAVYYCVAA PWRCTHDNCS KTRASWGQGT

MVTVSSGSEQ KGGGEEDDEE

-AB3 with linker 2; VR2-801-45

SEQ ID NO: 21

MQVQLVESGG GLIKPGGSLR LSCAASGDML SYDVMSWVRQ

APGKGLEWVS AISSSGGSTY YADSVKGRFT ISRDNSKNTV

YLQMNSLRAE DTAVYYCVAA PWRCTHDNCS KTRASWGQGT

MVTVSSGSEQ KLISEEDLNH HHHH

-AB3m

SEQ ID NO: 22

MKKQVQLVES GGGLIKPGGS LRLSCPASGD MLSYDVMSWV

RQAPGKGLEW VSAISSSGGS TYYADSVKGR FTISRDNSKN

TVYLQMNSLR AEDTAVYYCV AAPWRCTHDN CSKTRASWGQ

GTMVTVSS

-AB3m with linker; V45N2K

SEQ ID NO: 23

MKKQVQLVES GGGLIKPGGS LRLSCAASGD MLSYDVMSWV

RQAPGKGLEW VSAISSSGGS TYYADSVKGR FTISRDNSKN

TVYLQMNSLR AEDTAVYYCV AAPWRCTHDN CSKTRASWGQ

GTMVTVSSGS EEEDDDG

-V45H2

SEQ ID NO: 24

MQVQLVESGG GLIKPGGSLR LSCAASGDML SYDVMSWVRQ

APGKGLEWVS AISSSGGSTY YADSVKGRFT ISRDNSKNTV

YLQMNSLRAE DTAVYYCVAA PWRCTHDNCS KTRASWGQGT

MVTVSSGSEQ KLISEEDLNG GGEDEGC

-AB4; V38

SEQ ID NO: 25

MQVKLEESGG GLVQAGGSLR LSCAASGGTA SSYAMGWFRQ

APGKEREFVA AISRSGGNTD YVDSAKGRFT ISRDDAKNTV

SLQMNSLRLE DTAVYYCAAR YAGTWPNDAG TVYWLPPNYN

YWGQGTQVTV SS

-AB4 with linker

SEQ ID NO: 26

MQVKLEESGG GLVQAGGSLR LSCAASGGTA SSYAMGWFRQ

APGKEREFVA AISRSGGNTD YVDSAKGRFT ISRDDAKNTV

SLQMNSLRLE DTAVYYCAAR YAGTWPNDAG TVYWLPPNYN

YWGQGTQVTV SSGSEQ

-AB4 with linker 2; VR2-38

SEQ ID NO: 27

MQVKLEESGG GLVQAGGSLR LSCAASGGTA SSYAMGWFRQ

APGKEREFVA AISRSGGNTD YVDSAKGRFT ISRDDAKNTV

SLQMNSLRLE DTAVYYCAAR YAGTWPNDAG TVYWLPPNYN

YWGQGTQVTV SSGSEQKLIS EEDLNHHHHH H

-AB4m

SEQ ID NO: 28

QVKLEESGGG LVQAGGSLRL SCAASGGTAS SYAMGWERQA

PGKEREFVAA ISRSGGNTDY VDSAKGRFTI SRDDAKNTVS

LQMNSLRLED TAVYYCAARY AGTWPNDAGT VYWLPPNYNY

WGQGTQVTVS S

-AB4m with linker

SEQ ID NO: 29

QVKLEESGGG LVQAGGSLRL SCAASGGTAS SYAMGWFRQA

PGKEREFVAA ISRSGGNTDY VDSAKGRFTI SRDDAKNTVS

LQMNSLRLED TAVYYCAARY AGTWPNDAGT VYWLPPNYNY

WGQGTQVTVS SGSEQKLISE EDLNHHHHHH

-AB4c; V38H3

SEQ ID NO: 30

MQVKLEESGG GLVQAGGSLR LSCAASGGTA SSYAMGWFRQ

APGKEREFVA AISRSGGNTD YVDSAKGRFT ISRDDAKNTV

SLQMNSLRLE DTAVYYCAAR YAGTWPNDAG TVYWLPPNYN

YWGQGTQVTV SSGSEQKGGG DEDGC or a sequence at least 85%, at least 86%, at least 87%, at least 88%, at least 89%, at least 90%, at least 91%, at least 92%, at least 93%, at least 94% or at least 95% identical thereto, or a sequence substantially identical thereto.

These sequences may be coded by any nucleic acid sequence that would result in the recited amino acid sequence, as will be understood due to the degeneracy of the genetic code. Examples of nucleic acid sequences that may code the above-noted amino acid sequences include but are not limited to:

-AB1; V21

SEQ ID NO: 31 atgcaggtgc agctggtgga atccggcggc ggcctggtgc aggcgggcgg ctccctgcgt ctgtcctgcg cggcgtccgg ccgtgcgttt tcctcctatg cgatgggctg gtttcgtcag gcgccgggca aagaacgtga actggtggcg gcgatttcct ggtccgatga ttccacctat tatgcgaatt ccgtgaaagg ccgtttttacc atttcccgtg ataatgcgaa atccgcggtg tatctacaga tgaattccct gaaaccggaa gataccgcgg tgtattattg cgcggcgcat aaatccctac agcgtccgga tgaatatacc tattggggcc agggcaccca ggtgaccgtg tcctcc

-AB1

SEQ ID NO: 32 atgcaggtgc agcttgtgga gtccggcgga ggtcttgtcc aggcaggagg gtctttgcgc ctgagctgcg cggcgagtgg -continued gcgcgcgttc agcagttacg cgatgggttg gttccgccag gcccctggga agagcgtga acttgtggct gccatttctt ggtctgatga ttccacctat tatgctaatt cagttaaggg ccgtttcacg attagccgcg ataatgctaa atccgccgtc tatcttcaga tgaacagcct taagcctgaa gatacggcag tatattattg tgccgctcat aagagtctgc aacgcccgga cgaatataca tactggggac agggcacgca agttaccgtt tccagc -AB1 with linker; V21H2

SEQ ID NO: 33 atgcaggtgc agctggtgga atccggcggc ggcctggtgc aggcgggcgg ctccctgcgt ctgtcctgcg cggcgtccgg ccgtgcgttt tcctcctatg cgatgggctg gtttcgtcag gcgccgggca agaacgtga actggtggcg gcgatttcct ggtccgatga ttccacctat tatgcgaatt ccgtgaaagg ccgttttacc atttccgtg ataatgcgaa atccgcggtg tatctacaga tgaattccct gaaaccgaa gataccgcgg tgtattattg cgcggcgcat aaatccctac agcgtccgga tgaatatacc tattggggcc agggcaccca ggtgaccgtg tcctccggct ccgaacagaa aggcggcggc gaagaagatg atggc -AB1 with linker 2; VR2-21

SEQ ID NO: 34 atgcaggtgc aactggttga atcaggtgga ggactggtgc aggccggggg atctttacgc ttatcatgtg cagcttcggg gcgtgccttc tcctcttatg cgatgggatg gttccgccaa gccccccggca aggagcgtga gctggtagca gccatttcct ggtcagacga cagtacctac tacgcaaact cagtcaaagg gcgcttcact atctctcgcg acaatgccaa atccgctgtg tacttgcaaa tgaactcatt gaagccagag gatacggctg tctattactg cgcagcccac aagagtttac agcgtccaga tgaatacacc tattggggac aaggtacaca agttaccgtt agttcgggta gcgaacaaaa gttgatctct gaggaggact taaatcatca tcatcatcac cat -AB1c; V21H4

SEQ ID NO: 35 atgcaggtgc agcttgtgga gtccggcgga ggtcttgtcc aggcaggagg gtctttgcgc ctgagctgcg cggcgagtgg gcgcgcgttc agcagttacg cgatgggttg gttccgccag gcccctggga agagcgtga acttgtggct gccatttctt ggtctgatga ttccacctat tatgctaatt cagttaaggg ccgtttcacg attagccgcg ataatgctaa atccgccgtc tatcttcaga tgaacagcct taagcctgaa gatacggcag tatattattg tgccgctcat aagagtctgc aacgcccgga cgaatataca tactggggac agggcacgca agttaccgtt tccagcggtt ctgaacagaa aggaggcggt gaagaggatg atggctgc -AB1m-2

SEQ ID NO: 36 atgaaagcga tcttcgttct gaaaggttct ctggaccgtg acccggaatt cgacgacgaa ggtggtggtc aggttcagct ggttgaatct ggtggtggtc tggttcaggc gggtggttct ctgcgtctgt cttgcgcggc gtctggtcgt gcgttctctt cttacgcgat gggttggttc cgtcaggcgc gggtaaaga acgtgaactg gttgcggcga tctcttggtc tgacgactct acctactacg cgaactctgt aaaggtcgt ttcaccatct ctcgtgacaa cgcgaaatct gcggtttacc tacagatgaa ctctctgaaa ccggaagaca ccgcggttta ctactgcgcg gcgcacaaat ctctacagcg tccggacgaa tacacctact ggggtcaggg tacccaggtt accgtttctt ct -AB1m-2 with linker; V21H3

SEQ ID NO: 37 atgaaagcga tcttcgttct gaaaggttct ctggaccgtg acccggaatt cgacgacgaa ggtggtggtc aggttcagct ggttgaatct ggtggtggtc tggttcaggc gggtggttct ctgcgtctgt cttgcgcggc gtctggtcgt gcgttctctt cttacgcgat gggttggttc cgtcaggcgc gggtaaaga acgtgaactg gttgcggcga tctcttggtc tgacgactct acctactacg cgaactctgt aaaggtcgt ttcaccatct ctcgtgacaa cgcgaaatct gcggtttacc tacagatgaa ctctctgaaa ccggaagaca ccgcggttta ctactgcgcg gcgcacaaat ctctacagcg tccggacgaa tacacctact ggggtcaggg tacccaggtt accgtttctt ctggttctga acag

-AB2; V18

SEQ ID NO: 38 atgcaagttc agttagtaga aagtggtggt gtttaatca aaccgggtgg ttcacttcgt ttatcgtgcg cagcaagcgg gtttcgtttt tcagcagaat caatgacatg ggttcgtcaa gcaccgggca aaggtttaga gtgggtttca gcaatttcat caagtggcgg ttcaacttat tatgcagatt cggttaaagg tcgtttcaca atttctcgcg ataactcaaa aaatacggtt tatttacaaa tgaattcctt acgtgcagaa gatacagcag tttattattg tgttcgttct ccaaaaggtt gtactcacgc atcttgtagt tggaatagtg gtagttgggg tcaaggtaca ttagttacag tctcaagc

-AB2

SEQ ID NO: 39 atgcaggtgc agttagttga gtcgggcggg ggtcttatta aaccaggtgg aagccttcgt ctgtcttgtg cagcatcagg -continued

```
ctttcgtttt tccgcggaaa gcatgacctg ggtacgccaa
gcgcctggca aaggattgga gtgggtttcg gccatttctt
cttcaggagg atcaacgtac tatgcagact ccgtaaaagg
acgcttcacg atttctcgcg ataactctaa gaacaccgtg
tacttacaaa tgaactcttt acgtgcagag gacacagcag
tgtattattg tgttcgctca cccaaaggct gcacccatgc
gtcatgctct tggaactcag gttcgtgggg ccaggggacc
ttggtgacag tatcctcg
```

-AB2 with linker

SEQ ID NO: 40
```
atgcaagttc agttagtaga aagtggtggt ggtttaatca
aaccgggtgg ttcacttcgt ttatcgtgcg cagcaagcgg
gtttcgtttt tcagcagaat caatgacatg ggttcgtcaa
gcaccgggca aaggtttaga gtgggtttca gcaatttcat
caagtggcgt tcaacttat tatgcagatt cggttaaagg
tcgtttcaca atttctcgcg ataactcaaa aaatacggtt
tatttacaaa tgaattcctt acgtgcagaa gatacagcag
tttattattg tgttcgttct ccaaaaggtt gtactcacgc
atccttgtagt tggaatagtg gtagttgggg tcaaggtaca
ttagttacag tctcaagcgg ttcagaagaa gatgacgatg
aagaaaaa
```

-AB2 with linker 2; VR2-801-18

SEQ ID NO: 41
```
atgcaggtgc agttagttga gtcgggcggg ggtcttatta
aaccaggtgg aagccttcgt ctgtcttgtg cagcatcagg
ctttcgtttt tccgcggaaa gcatgacctg ggtacgccaa
gcgcctggca aaggattgga gtgggtttcg gccatttctt
cttcaggagg atcaacgtac tatgcagact ccgtaaaagg
acgcttcacg atttctcgcg ataactctaa gaacaccgtg
tacttacaaa tgaactcttt acgtgcagag gacacagcag
tgtattattg tgttcgctca cccaaaggct gcacccatgc
gtcatgctct tggaactcag gttcgtgggg ccaggggacc
ttggtgacag tatcctcggg ctccaacag aagttaatta
gtgaagaaga tttgaaccac caccaccatc ac
```

-AB2m-2

SEQ ID NO: 42
```
atgaaagcga tcttcgttct gaaaggttct ctggaccgtg
acccggaatt cgacgacgaa gaaggtggtg gtcaggttca
gctggttgaa tctggtggtg gtctgatcaa accgggtggt
tctctgcgtc tgtcttgcgc ggcgtctggt ttccgtttct
ctgcggaatc tatgacctgg gttcgtcagg cgccgggtaa
aggtctggaa tgggtttctg cgatctcttc ttctggtggt
tctacctact acgcggactc tgttaaaggt cgtttcacca
```

```
tctctcgtga caactctaaa aacaccgttt acttacaaat
gaactctctg cgtgcggaag acaccgcggt ttactactgc
gttcgttctc cgaaaggttg cacccacgcg tcttgctctt
ggaactctgg ttcttggggt cagggtaccc tggttaccgt
ttcttct
```

-AB2m-2 with linker, V18H2

SEQ ID NO: 43
```
atgaaagcga tcttcgttct gaaaggttct ctggaccgtg
acccggaatt cgacgacgaa gaaggtggtg gtcaggttca
gctggttgaa tctggtggtg gtctgatcaa accgggtggt
tctctgcgtc tgtcttgcgc ggcgtctggt ttccgtttct
ctgcggaatc tatgacctgg gttcgacagg cgccgggtaa
aggtctggaa tgggtttctg cgatctcttc ttctggtggt
tctacctact acgcggactc tgttaaaggt cgtttcacca
tctctcgtga caactctaaa aacaccgttt acttacaaat
gaactctctg cgtgcggaag acaccgcggt ttactactgc
gttcgttctc cgaaaggttg cacccacgcg tcttgctctt
ggaactctgg ttcttggggt cagggtaccc tggttaccgt
ttcttctggt tctgacgaag aa
```

-AB3, V45

SEQ ID NO: 44
```
atgcaggtgc agctggtgga aagcggcggc ggcctgatta
aaccgggcgg cagcctgcgc ctgagctgcg cggcgagcgg
cgatatgctg agctatgatg tgatgagctg ggtgcgccag
gcgccgggca aaggcctgga atgggtgagc gcgattagca
gcagcggcgg cagcacctat tatgcggata gcgtgaaagg
ccgctttacc attagccgcg ataacagcaa aaacaccgtg
tatctgcaga tgaacagcct gcgcgcggaa gataccgcgg
tgtattattg cgtggcggcg ccgtggcgct gcacccatga
taactgctct aaaaacccgcg cgagctgggg ccagggcacc
atggtgaccg tg
```

-AB3

SEQ ID NO: 45
```
atgcaagtac agttagtgga gagtggagga gggctgatta
agccaggcgg ctctttgcgt ctgagttgtg cggcatcagg
cgatatgtta agctacgatg tgatgagttg ggtgcgtcaa
gcgccaggaa aaggacttga atgggtcagc gcaatttcgt
cgtccggtgg gtctacttac tacgctgatt cggttaaggg
ccgcttcacc atctcccgcg acaattcaaa gaatacggta
tatctgcaaa tgaatagttt gcgtgcggag gacacagcag
tctactattg cgttgcagct ccctggcgct gtactcacga
taactgttca aaaacccgcg catcatgggg tcaaggtaca
atggtgacag tgtcatct
```

-AB3 with linker; V45H1

SEQ ID NO: 46
atgcaggtgc agctggtgga aagcggcggc ggcctgatta
aaccgggcgg cagcctgcgc ctgagctgcg cggcgagcgg
cgatatgctg agctatgatg tgatgagctg ggtgcgccag
gcgccgggca aaggcctgga atgggtgagc gcgattagca
gcagcggcgg cagcacctat atgcggata gcgtgaaagg
ccgcttaacc attagccgcg ataacagcaa aaacaccgtg
tatcttcaga tgaacagcct gcgcgcgaa gataccgcgg
tgtattattg cgtggcggcg ccgtggcgct gcacccatga
taactgctct aaaacccgcg cgagctgggg ccagggcacc
atggtgaccg tgagcagcgg cagcgaacag aaaggcggcg
gcgaagaaga tgatgaagaa -AB3 with linker 2; VR2-801-45

SEQ ID NO: 47
atgcaagtac agttagtgga gagtggagga gggctgatta
agccaggcgg ctctttgcgt ctgagttgtg cggcatcagg
cgatatgtta agctacgatg tgatgagttg ggtgcgtcaa
gcgccaggaa aaggacttga atgggtcagc gcaatttcgt
cgtccggtgg gtctacttac tacgctgatt cggttaaggg
ccgcttcacc atctcccgcg acaattcaaa gaatacggta
tatctgcaaa tgaatagttt gcgtgcggag gacacagcag
tctactattg cgttgcagct ccctggcgct gtactcacga
taactgttca aaaacccgcg catcatgggg tcaaggtaca
atggtgacag tgtcatctgg tagtgaacag aagttaatta
gtgaagagga cctaatcat catcatcatc ac

-V45H2

SEQ ID NO: 48
atgcaggttc agctggttga atctggtggt ggtctgatca
aaccgggtgg ttctctgcgt ctgtcttgcg cggcgtctgg
tgacatgctg tcttacgacg ttatgtcttg ggttcgtcag
gcgccgggta aaggtatgga atgggtttct gcgatctctt
cttctggtgg ttctacctac tacgcggact ctgttaaagg
tcgtttcacc atctctcgtg acaactctaa aaacaccgtt
tacctgcaaa tgaactctct gcgtgcgaa gacaccgcgg
tttactactg cgttgcggcg ccgtggcgtt gcacccacga
caactgctct aaaacccgtg cgtcttgggg tcagggtacc
atggttaccg tttcttctgg ttctgaacag aaactgatct
ctgaagaaga cctgaacggt ggtggtgaag acgaaggttg c

-AB4; V38

SEQ ID NO: 49
atgcaagtaa aactcgaaga atcaggtgga ggattggttc
aagctggtgg gtcattacgt ttgtcctgtg cagcaagtgg
cggtactgcg tcaagttatg caatggggttg gtttcgtcaa
gctcccggta agaacgtga atttgttgcc gcaattagtc ggtccggagg aaatacagat tatgtagact cagcaaaagg
tcgttttact atctcacgcg atgatgcaaa aaatacggtt
tccttacaaa tgaactctct gcgcctcgaa gataccgcgg
tatattattg cgctgcccgc tacgccggta cctggccgaa
tgatgctggc actgtatatt ggctgccacc gaattacaac
tattggggtc aaggaactca agtcacggta agcagc

-AB4

SEQ ID NO: 50
atgcaggtta aattagagga atcaggtgga ggtttggttc
aagcaggtgg tagcttgcgc ctgagttgtg ccgctagcgg
gggcacagcc agttcatacg cgatggggtg gtttcgccag
gccctggaa aggagcgtga attcgttgct gcgattagtc
gtagcggcgg taacacggat tacgtggaca gcgcgaaggg
acgctttaca atttctcgtg atgacgcaaa gaacacggtg
tccctgcaaa tgaactcact tcgcctggaa gacaccgcgg
tgtattattg tgcagcccgc tacgcggaa cttggccgaa
cgatgctggt accgtgtact ggttaccccc taattacaat
tactggggcc aaggtaccca agtcaccgtc tcctcg -AB4 with linker SEQ ID NO: 51
atgcaagtaa aactcgaaga atcaggtgga ggattggttc
aagctggtgg gtcattacgt ttgtcctgtg cagcaagtgg
cggtactgcg tcaagttatg caatggggttg gtttcgtcaa
gctcccggta agaacgtga atttgttgcc gcaattagtc
ggtccggagg aaatacagat tatgtagact cagcaaaagg
tcgttttact atctcacgcg atgatgcaaa aaatacggtt
tccttacaaa tgaactctct gcgcctcgaa gataccgcgg
tatattattg cgctgcccgc tacgccggta cctggccgaa
tgatgctggc actgtatatt ggctgccacc gaattacaac
tattggggtc aaggaactca agtcacggta agcagcggtt
ccgaacaaaa gggtggtgga gaagaagatg atggcaaa -AB4 with linker 2; VR2-38

SEQ ID NO: 52
atgcaggtta aattagagga atcaggtgga ggtttggttc
aagcaggtgg tagcttgcgc ctgagttgtg ccgctagcgg
gggcacagcc agttcatacg cgatggggtg gtttcgccag
gccctggaa aggagcgtga attcgttgct gcgattagtc
gtagcggcgg taacacggat tacgtggaca gcgcgaaggg
acgctttaca atttctcgtg atgacgcaaa gaacacggtg
tccctgcaaa tgaactcact tcgcctggaa gacaccgcgg
tgtattattg tgcagcccgc tacgcggaa cttggccgaa
cgatgctggt accgtgtact ggttaccccc taattacaat
tactggggcc aaggtaccca agtcaccgtc tcctcgggaa

```
-continued
gcgaacaaaa gctgattagc gaagaggatc ttaaccatca tcatcaccat cac
```

-AB4c; V38H3

SEQ ID NO: 53
```
atgcaggtta aactggaaga atctggtggt ggtctggttc aggcgggtgg ttctctgcgt ctgtcttgcg cggcgtctgg tggtaccgcg tcttcttacg cgatgggttg gttccgtcag gcgccgggta aagaacgtga attcgttgcg gcgatctctc gttctggtgg taacaccgac tacgttgact ctgcgaaagg tcgtttcacc atctctcgtg acgacgcgaa aaacaccgtt tctctgcaaa tgaactctct gcgtctggaa gacaccgcgg tttactactg cgcggcgcgt tacgcgggta cctggccgaa cgacgcgggt accgtttact ggctgccgcc gaactacaac tactggggtc agggtaccca ggttaccgtt tcttctggtt ctgaacagaa aggtggtggt gacgaagacg gttgc
``` or a sequence at least 85%, at least 86%, at least 87%, at least 88%, at least 89%, at least 90%, at least 91%, at least 92%, at least 93%, at least 94% or at least 95% identical thereto, or a sequence substantially identical thereto.

Linker sequences suitable for the single domain antibodies of the invention may be selected from the group consisting of GSEQ (SEQ ID NO:54), GSDEE (SEQ ID NO:55), GSEEEDDDG (SEQ ID NO:56), GSEEEDDDGKK (SEQ ID NO:57), GSEQKGGGEEDDG (SEQ ID NO:58), GSEQKLISEEDLNHHHHH (SEQ ID NO:59), GSEQKLISEEDLNHHHHHH (SEQ ID NO:60), GSEEDDDEEK (SEQ ID NO:61), GSEQKGGGEEDDEE (SEQ ID NO:62), GSEQKLISEEDLNGGGEDDEEG (SEQ ID NO:63), GSEQKLISEEDLNGGGEDEG (SEQ ID NO:64), and GSEQKGGGDEDG (SEQ ID NO:65). In aspects, a linker sequence may further comprise a C-terminal cysteine, for example GSEQKGGGEEDDC (SEQ ID NO:66), GSEQKLISEEDLNGGGEDDEEGC (SEQ ID NO:67), GSEQKLISEEDLNGGGEDEGC (SEQ ID NO:68), and GSEQKGGGDEDGC (SEQ ID NO:69). Sequences similar to these linker sequences may be used herein. For example, KK is a suitable linker sequence and those comprising any one of the sequences of SEQ ID NO:54-69.

The CAR comprises a VEGFR-2 binding moiety that binds to VEGFR-2, an epitope thereof, a fragment thereof, or variants of the aforementioned and further comprises an immune cell activation domain. When expressed by an immune cell, the VEGFR-2 binding moiety is or is part of an extracellular domain and the immune cell activation domain is or is part of an intracellular signaling domain, typically of the T cell antigen receptor complex zeta chain (e.g., CD3 zeta). Co-stimulatory signaling regions may also be included in the intracellular domain and are cell surface molecules other than antigens receptors or their ligands that are required for an efficient response of lymphocytes to antigen. A spacer moiety (also referred to as a hinge moiety) is typically included in the extracellular domain to allow the VEGFR-2 binding moiety to efficiently bind to its epitope. The intracellular and extracellular domains are linked through a transmembrane domain that crosses the cytoplasmic membrane.

A representative non-limiting structure of the CAR of the invention comprises a single domain antibody recognizing a VEGFR-2 of a tumor cell, a transmembrane domain, and an intracellular domain of a TCR complex CD3ζ that activates a T cell (called a first generation CAR). In an aspect, the CAR comprises the sequence of SEQ ID NO:78:

```
MALPVTALLL PLALLLHAAR PMQVQLVESG GGLVQAGGSL

RLSCAASGRA FSSYAMGWFR QAPGKERELV AAISWSDDST

YYANSVKGRF TISRDNAKSA VYLQMNSLKP EDTAVYYCAA

HKSLQRPDEY TYWGQGTQVT VSSTTTPAPR PPTPAPTIAS

QPLSLRPEAC RPAAGGAVHT RGLDFACDFW VLVVVGGVLA

CYSLLVTVAF IIFWVRSKRS RLLHSDYMNM TPRRPGPTRK

HYQPYAPPRD FAAYRSKRGR KKLLYIFKQP FMRPVQTTQE

EDGCSCRFPE EEEGGCELRV KFSRSADAPA YKQGQNQLYN

ELNLGRREEY DVLDKRRGRD PEMGGEPRRK NPQEGLYNEL

QKDKMAEAYS EIGMKGERRR GKGHDGLYQG LSTATKDTYD

ALHMQALPPR PGEGRGSLLT CGDVEENPGP MWLQSLLLLG

TVACSISRKV CNGIGIGEFK DSLSINATNI KHFKNCTSIS

GDLHILPVAF RGDSFTHTPP LDPQELDILK TVKEITGFLL

IQAWPENRTD LHAFENLEII RGRTKQHGQF SLAVVSLNIT

SLGLRSLKEI SDGDVIISGN KNLCYANTIN WKKLFGTSGQ

KTKIISNRGE NSCKATGQVC HALCSPEGCW GPEPRDCVSC

RNVSRGRECV DKCNLLEGEP REFVENSECI QCHPECLPQA

MNITCTGRGP DNCIQCANYI DGPHCVKTCP AGVMGENNTL

VWKYADAGHV CHLCHPNCTY GCTGPGLEGC PTNGPKIPSI

ATGMVGALLL LLVVALGIGL FM
``` or a fragment or variant thereof.

The nucleic acid sequence of such a single domain antibody may be obtained by a variety of methods as is understood by one of skill in the art. For example, the nucleic acid sequence may be the sequence of SEQ ID NO:79:

```
atggccttac cagtgaccgc cttgctcctg ccgctggcct tgctgctcca cgccgccagg ccgATGCAGG TGCAGCTTGT

GGAGTCCGGC GGAGGTCTTG TCCAGGCAGG AGGGTCTTTG

CGCCTGAGCT GCGCGGCGAG TGGGCGCGCG TTCAGGAGTT

ACGCGATGGG TTGGTTCCGC CAGGCCCCTG GGAAAGAGCG

TGAACTTGTG GCTGCCATTT CTTGGTCTGA TGATTCCACC

TATTATGCTA ATTCAGTTAA GGGCCGTTTC ACGATTAGCC

GCGATAATGC TAAATCCGCC GTCTATCTTC AGATGAACAG

CCTTAAGCCT GAAGATACGG CAGTATATTA TTGTGCCGCT

CATAAGAGTC TGCAACGCCC GGACGAATAT ACATACTGGG

GACAGGGCAC GCAAGTTACC GTTTCCAGCa ccacgacgcc agcgccgcga ccaccaacac cggcgcccac catcgcgtcg
```

```
cagccctgt ccctgcgccc agaggcgtgc cggccagcgg cgggggcgc agtgcacacg aggggctgg acttcgcctg tgatttctgg gtgctggtcg ttgtgggcgg cgtgctggcc tgctacagcc tgctggtgac agtggccttc atcatctttt gggtgaggag caagcggagc agactgctgc acagcgacta catgaacatg accccccgga ggcctggcc cacccggaag cactaccagc cctacgcccc tcccagggat ttcgccgcct accggagcaa acggggcaga aagaaactcc tgtatatatt caaacaacca tttatgagac cagtacaaac tactcaagag gaagatggct gtagctgccg atttccagaa gaagaagaag gaggatgtga actgagagtg aagttcagca ggagcgcaga cgcccccgcg tacaagcagg gccagaacca gctctataac gagctcaatc taggacgaag agaggagtac gatgttttgg acaagagacg tggccgggac cctgagatgg ggggaaagcc gagaaggaag aaccctcagg aaggcctgta caatgaactg cagaaagata agatggcgga ggcctacagt gagattggga tgaaaggcga gcgccggagg ggcaaggggc acgatggcct ttaccagggt ctcagtacag ccaccaagga cacctacgac gcccttcaca tgcaggccct gccccctcgc CCCGGGGAGG

GCAGAGGCAG CCTGCTGACA TGTGGCGACG TGGAAGAGAA

CCCTGGCCCC ATGTGGGTGC AGAGCCTGCT GGTCTTGGGC

ACTGTGGCCT GCAGCATCTC TCGCAAAGTG TGTAACGAA

TAGGTATTGG TGAATTTAAA GACTCACTCT CCATAAATGC

TACGAATATT AAACACTTCA AAAACTGCAC CTCCATCAGT

GGCGATCTCC ACATCCTGCC GGTGGCATTT AGGGGTGACT

CCTTCACACA TACTCCTCCT CTGGATCCAC AGGAACTGGA

TATTCTGAAA ACCGTAAAGG AAATCACAGG GTTTTTGCTG

ATTCAGGCTT GGCCTGAAAA CAGGACGGAC CTCCATGCCT

TTGAGAACCT AGAAATCATA CGCGGCAGGA CCAAGCAACA

TGGTCAGTTT TCTCTTGCAG TCGTCAGCCT GAACATAAGA

TCCTTGGGAT TACGCTCCCT CAAGGAGATA AGTGATGGAG

ATGTGATAAT TTCAGGAAAC AAAAATTTGT GCTATGCAAA

TACAATAAAC TGGAAAAAAC TGTTTGGGAC CTCCGGTCAG

AAAACCAAAA TTATAAGCAA CAGAGGTGAA AACAGCTGCA

AGGCCACAGG CCAGGTCTGC CATGCCTTGT GCTCCCCCGA

GGGCTGCTGG GGCCCGGAGC CCAGGGACTG CGTCTCTTGC

CGGAATGTCA GCCGAGGCAG GGAATGCGTG GACAAGTGCA

ACCTTCTGGA GGGTGAGCCA AGGGAGTTTG TGGAGAACTC

TGAGTGCATA CAGTGCCACC CAGAGTGCCT GCCTCAGGCC

ATGAACATCA CCTGCACAGG ACGGGGACCA GACAACTGTA
```

```
TCCAGTGTGC CCACTACATT GACGGCCCCC ACTGCGTCAA

GACCTGCCCG GCAGGAGTCA TGGGAGAAAA CAACACCCTG

GTCTGGAAGT ACGCAGACGC CGGCCATGTG TGCCACCTGT

GCCATCCAAA CTGCACCTAC GGATGCACTG GGCCAGGTCT

TGAAGGCTGT CCAACGAATG GGCCTAAGAT CCCGTCCATC

GCCACTGGGA TGGTGGGGGC CCTCCTCTTG CTGCTGGTGG

TGGCCCTGGG GATCGGCCTC TTCATG
```

A T cell expressing a CAR directly recognizes a surface antigen of a tumor cell independently of the expression of major histocompatibility antigen class I on the tumor cell, and at the same time, activates the T cell, and thereby the CAR-expressing T cell can efficiently kill the tumor cell.

For enhancing the ability of the first generation CAR to activate a T cell, a second generation CAR can be made whereby an intracellular domain of CD28 which is a co-stimulatory molecule of a T cell is linked to the first generation CAR. A third generation CAR may also be made whereby an intracellular domain derived from (for example) CD137 (4-1BB) or CD134 (OX40) which is a tumor necrosis factor (TNF) receptor superfamily is tandemly linked to a first generation CAR. Thus, many CAR molecules targeting VEGFR-2 are included in the present invention.

The CAR of the invention includes functional portions thereof. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs, polypeptides, and proteins described herein. The term "functional variant" as used herein refers to a CAR, polypeptide, or protein having substantial or significant sequence identity or similarity to a parent CAR, polypeptide, or protein, which functional variant retains the biological activity (binding to VEGFR-2) of the CAR, polypeptide, or protein of which it is a variant. Functional variants encompass, for example, those variants of the CAR, polypeptide, or protein described herein (the parent CAR, polypeptide, or protein) that retain the ability to recognize target cells to a similar extent, the same extent, or to a higher extent, as the parent CAR, polypeptide, or protein. In reference to the parent CAR, polypeptide, or protein, the functional variant can, for instance, be at least about 30%, 50%, 75%, 80%, 90%, 98% or more identical in amino acid sequence to the parent CAR, polypeptide, or protein.

A functional variant can, for example, comprise the amino acid sequence of the parent CAR, polypeptide, or protein with at least one conservative amino acid substitution. Alternatively or additionally, the functional variants can comprise the amino acid sequence of the parent CAR, polypeptide, or protein with at least one non-conservative amino acid substitution. In this case, it is typical for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR, polypeptide, or protein.

Amino acid substitutions of the inventive CARs are typically conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The CAR, polypeptide, or protein can consist essentially of the specified amino acid sequence or sequences described herein, such that other components e.g., other amino acids, do not materially change the biological activity of the functional variant.

The CARs, polypeptides, and proteins of embodiments of the invention (including functional portions and functional variants) can be of any length, i.e., can comprise any number of amino acids, provided that the CARs, polypeptides, or proteins (or functional portions or functional variants thereof) retain their biological activity, e.g., the ability to specifically bind to VEGFR-2, treat or prevent disease in a host, etc. For example, the polypeptide can be about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The CARs, polypeptides, and proteins of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, .alpha.-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, .beta.-phenylserine .beta.-hydroxyphenylalanine, phenylglycine, .alpha.-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, .alpha.-aminocyclopentane carboxylic acid, .alpha.-aminocyclohexane carboxylic acid, .alpha.-aminocycloheptane carboxylic acid, .alpha.-(2-amino-2-norbornane)-carboxylic acid, .alpha., .gamma.-diaminobutyric acid, .alpha.,.beta.-diaminopropionic acid, homophenylalanine, and .alpha.-tert-butylglycine.

The CARs, polypeptides, and proteins of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

VEGFR-2 Binding Moiety

In typical aspects, the CAR described herein is specific for VEGFR-2, fragments thereof, epitopes thereof and variants of any of the foregoing. The VEGFR-2 binding moiety of the invention is such that it binds with a desired affinity to VEGFR-2 harbored on a cell/tumor surface leading to (1) downregulation of the receptor to decrease angiogenesis and (2) activation of the immune cell in which it is provided, to trigger cytotoxic activity and release cytokines within the tumor microenvironment and further proliferating.

Without wishing to be bound by theory, it is believed that this antibody/VEGFR-2epitope interaction has an advantageous level of affinity (not too high and not too low), such that the antibody can bind the epitope on a first cell and activate cell killing, then move on to bind a further epitope on a second or further cell and activate further cell killing.

Thus, also described herein is a CAR comprising, within the VEGFR-2 binding moiety a complementarity determining region (CDR) 1; a CDR2; and a CDR3 wherein the antibody or fragment thereof is specific for VEGFR-2.

The terms "antibody" and "antibody fragment" ("fragment thereof") are as defined above. As previously stated, the antibody or fragment thereof may be an sdAb. The sdAb may be of camelid origin (e.g., from a species of the family Camelidae) or be derived from a camelid $V_{HH}$, and thus may be based on camelid framework regions; alternatively, the CDR described above may be grafted onto $V_{NAR}$, $V_{HH}$ or $V_L$ framework regions. In yet another alternative, the hypervariable loops described above may be grafted onto the framework regions of other types of antibody fragments (Fv, scFv, Fab).

The present aspect further encompasses an antibody fragment that is "humanized" using any suitable method known in the art, for example, but not limited to CDR grafting and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the heavy chain CDR defined herein may be fused or grafted to a human variable region ($V_H$, or $V_L$), or to other human antibody fragment framework regions (Fv, scFv, Fab). In such a case, the conformation of said one or more than one hypervariable loop is preserved, and the affinity and specificity of the sdAb for its target (i.e., toxins A and B) is also preserved.

CDR grafting is described in at least the following: U.S. Pat. Nos. 6,180,370, 5,693,761, 6,054,297, 5,859,205, and European Patent No. 626390 (the disclosures of which are hereby incorporated by reference in their entirety). Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is described in at least the following: U.S. Pat. Nos. 5,869,619, 5,766,886, 5,821,123, and European Patent No. 519596 (the disclosures of which are hereby incorporated by reference in their entirety). Persons of skill in the art would be amply familiar with methods of preparing such humanized antibody fragments.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at ca.expasy.org/tools/blast/), BLAST-P, Blast-N, or FASTA-N, or any other appropriate software that is known in the art.

The substantially identical sequences of the present invention may be at least 85% identical; in another example, the substantially identical sequences may be at least 70, 75, 80, 85, 90, 95, 96, 97, 98, 99, or 100% (or any percentage there between) identical at the amino acid level to sequences described herein. In specific aspects, the substantially identical sequences retain the activity and specificity of the reference sequence. In a non-limiting embodiment, the difference in sequence identity may be due to conservative amino acid mutation(s).

The single domain antibody or fragment thereof of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection tag, exemplary tag cassettes include Strep tag, or any variant thereof; see, e.g., U.S. Pat. No. 7,981,632, His tag, Flag tag having the sequence motif DYKDDDDK (SEQ ID NO: 93), Xpress tag, Avi tag, Calmodulin tag, Polyglutamate tag, HA tag, Myc tag, Nus tag, S tag, SBP tag, Softag 1, Softag 3, V5 tag, CREB-binding protein (CBP), glutathione S-transferase (GST), maltose binding protein (MBP), green fluorescent protein (GFP), Thioredoxin tag, or any combination thereof; a purification tag (for example, but not limited to a $His_5$ or $His_6$), or a combination thereof.

In another example, the additional sequence may be a biotin recognition site such as that described by Cronan et al in WO 95/04069 or Voges et al in WO/2004/076670. As is also known to those of skill in the art, linker sequences may be used in conjunction with the additional sequences or tags.

More specifically, a tag cassette may comprises an extracellular component that can specifically bind to an antibody with high affinity or avidity. Within a single chain fusion protein structure, a tag cassette may be located (a) immediately amino-terminal to a connector region, (b) interposed between and connecting linker modules, (c) immediately carboxy-terminal to a binding domain, (d) interposed between and connecting a binding domain (e.g., scFv) to an effector domain, (e) interposed between and connecting subunits of a binding domain, or (f) at the amino-terminus of a single chain fusion protein. In certain embodiments, one or more junction amino acids may be disposed between and connecting a tag cassette with a hydrophobic portion, or disposed between and connecting a tag cassette with a connector region, or disposed between and connecting a tag cassette with a linker module, or disposed between and connecting a tag cassette with a binding domain.

Transmembrane Domain

In particular aspects, the CAR comprises a transmembrane domain that is fused to the extracellular domain and intracellular domain of the CAR. In one aspect, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Typically, the transmembrane domain in the CAR described herein is the CD28 transmembrane domain.

Alternatively the transmembrane domain may be synthetic, in which case it will comprise predominantly hydrophobic residues such as leucine and valine. Typically a triplet of phenylalanine, tryptophan and valine will be found at each end of a synthetic transmembrane domain. Optionally, a short oligo- or polypeptide linker, typically between 2 and 10 amino acids in length may form the linkage between the transmembrane domain and the cytoplasmic signaling domain of the CAR. A glycine-serine doublet provides a particularly suitable linker.

Spacer Domain

Between the extracellular domain and the transmembrane domain of the CAR, or between the cytoplasmic domain and the transmembrane domain of the CAR, there may be incorporated a spacer domain, also referred to as a hinge domain. As used herein, the term "spacer domain" generally means any oligo- or polypeptide that functions to link the transmembrane domain to, either the extracellular domain or, the cytoplasmic domain in the polypeptide chain and elevate the VEGFR-2 binding domain from the cell surface. A spacer domain may comprise up to 300 amino acids, typically 10 to 100 amino acids and most typically 25 to 50 amino acids. The spacer may comprise one of the following, for example: a human an IgG1 Fc domain; an IgG1 hinge; an IgG1 hinge-CD8 stalk; a CD8 stalk; IgG1 hinge-CD28 stalk; and a CD28 stalk.

Cytoplasmic Domain

The cytoplasmic domain or otherwise the intracellular signaling domain of the CAR described herein is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Typical examples of intracellular signaling domains for use in the CAR described herein include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly typical that cytoplasmic signaling molecule in the CAR described herein comprises a cytoplasmic signaling sequence derived from CD3 zeta.

In a typical aspect, the cytoplasmic domain of the CAR can be designed to comprise the CD3-zeta signaling domain by itself or combined with any other desired cytoplasmic domain(s) useful in the context of the CAR described herein. For example, the cytoplasmic domain of the CAR can comprise a CD3 zeta chain portion and one or more costimulatory signaling regions. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like.

The cytoplasmic signaling sequences within the cytoplasmic signaling portion of the CAR described herein may be linked to each other in a random or specified order. Optionally, a short oligo- or polypeptide linker, typically between 2 and 10 amino acids in length may form the linkage. A glycine-serine doublet provides a particularly suitable linker.

In one aspect, the cytoplasmic domain is designed to comprise the signaling domain of CD3-zeta and the signaling domain of CD28. In another aspect, the cytoplasmic domain is designed to comprise the signaling domain of CD3-zeta and the signaling domain of 4-1BB. In yet another aspect, the cytoplasmic domain is designed to comprise the signaling domain of CD3-zeta and the signaling domain of CD28 and 4-1BB.

In one aspect, the cytoplasmic domain in the CAR described herein is designed to comprise the signaling domain of CD28 and/or 4-1BB and the signaling domain of CD3-zeta.

Vectors

Described herein are vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589.466, incorporated by reference herein in their entireties. In another aspect, the invention provides a gene therapy vector.

The nucleic acid (SEQ ID NO:31-53 or 80) can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193 the disclosures of which are hereby incorporated by reference in their entirety).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some aspects, adenovirus vectors are used. A number of adenovirus vectors are known in the art. In one aspect, lentivirus vectors are used.

Additional promoter elements, e g, enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part described herein. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A typical method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian. e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20.degree. C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope described herein.

Transposon/Transposase System

Typical methods for introducing DNA into a cell include DNA condensing reagents such as calcium phosphate, polyethylene glycol, and the like, lipid-containing reagents, such as liposomes, multi-lamellar vesicles, and the like, as well as virus-mediated strategies.

However, all of these methods have their limitations. For example, there are size constraints associated with DNA condensing reagents and virus-mediated strategies. Further, the amount of nucleic acid that can be transfected into a cell is limited in virus strategies. Not all methods facilitate insertion of the delivered nucleic acid into cellular nucleic acid and while DNA condensing methods and lipid-containing reagents are relatively easy to prepare, the insertion of nucleic acid into viral vectors can be labor intensive. Moreover, virus-mediated strategies can be cell-type or tissue-type specific and the use of virus-mediated strategies can create immunologic problems when used in vivo.

One suitable tool in order to overcome these problems are transposons. Transposons or transposable elements include a (short) nucleic acid sequence with terminal repeat sequences upstream and downstream thereof. Active transposons encode enzymes that facilitate the excision and insertion of the nucleic acid into target DNA sequences.

At present, two classes of transposons are known, i.e. class I and class II transposons.

Class I transposons, also called retrotransposons or retroposons, include retroviral-like retrotransposons and non-retroviral-like retrotransposons. They work by copying themselves and pasting copies back into the genome in multiple places. Initially, retrotransposons copy themselves to RNA (transcription) but, instead of being translated, the RNA is copied into DNA by a reverse transcriptase (often coded by the transposon itself) and inserted back into the genome. Typical representatives of class I transposons include e.g. Copia (*Drosophila*), Ty1 (yeast), THE-1 (human), Bs1 (maize), the F-element, L1 (human) or Cin4 (maize).

As a first step Class II transposons have to be transfected to the cells using standard methods like virus infection etc. Following that Class II transposons, also called "DNA-only transposons", move by a cut and paste mechanism, rather than by copy and paste, and use the transposase enzyme in this mechanism. Different types of transposases may work in different ways. Some can bind to any part of the DNA molecule, and the target site can be located at any position, while others bind to specific sequences. The transposase then cuts the target site to produce sticky ends, releases the transposon and ligates it into the target site. Typical class I1 representatives include the P element (*Drosophila*), Ac-Ds (maize), TN3 and IS1 (*E. coli*), Tam3 (snapdragon) etc.

Particularly, with class II transposons, the element-encoded transposase catalyzes the excision of the transposon from its original location and promotes its insertion elsewhere in the genome (Plasterk, 1996 Curr. Top. Microbiol. Immunol. 204, 125-143). Autonomous members of a transposon family can express an active transposase, the trans-acting factor for transposition, and thus are capable of transposing on their own. Non-autonomous elements have mutated transposase genes but may retain cis-acting DNA sequences. These cis-acting DNA sequences are also referred to as inverted terminal repeats (IR). Some inverted repeat sequences may include one or more direct repeat sequences. These sequences usually are embedded in the terminal inverted repeats (IRs) of the elements, which are required for mobilization in the presence of a complementary transposase from another element. Not a single autonomous element has been isolated from vertebrates so far with the exception of Tol2 (see below); all transposon-like sequences are defective, apparently as a result of a process called "vertical inactivation" (Lohe et al., 1995 Mol. Biol. Evol. 12, 62-72). According to one phylogenetic model (Hartl et al., 1997 Trends Genet. 13, 197-201), the ratio of non-autonomous to autonomous elements in eukaryotic genomes increases as a result of the trans-complementary nature of transposition. This process leads to a state where the ultimate disappearance of active, transposase-producing copies in a genome is inevitable. Consequently, DNA-transposons can be viewed as transitory components of genomes which, in order to avoid extinction, must find ways to establish themselves in a new host. Indeed, horizontal gene transmission between species is thought to be one of the important processes in the evolution of transposons (Lohe et al., 1995 supra and Kidwell, 1992. Curr. Opin. Genet Dev. 2, 868-873).

The natural process of horizontal gene transfer can be mimicked under laboratory conditions. In plants, transposons of the Ac/Ds and Spm families have been routinely transfected into heterologous species (Osborne and Baker, 1995 Curr. Opin. Cell Biol. 7, 406-413). In animals, however, a major obstacle to the transfer of an active transposon system from one species to another has been that of species-specificity of transposition due to the requirement for factors produced by the natural host.

Transposon systems as discussed above may occur in vertebrate and invertebrate systems. In vertebrates, the discovery of DNA-transposons, mobile elements that move via a DNA intermediate, is relatively recent (Radice, A. D., et al., 1994. Mol. Gen. Genet. 244, 606-612). Since then, inactive, highly mutated members of the Td/mariner as well as the hAT (hobo/Ac/Tam) superfamilies of eukaryotic transposons have been isolated from different fish species, Xenopus and human genomes (Oosumi et al., 1995. Nature 378, 873; Ivies et al. 1995. Mol. Gen. Genet. 247, 312-322; Koga et al., 1996. Nature 383, 30; Lam et al., 1996. J. Mol. Biol. 257, 359-366 and Lam, W. L., et al. Proc. Natl. Acad Sci. USA 93, 10870-10875).

Both invertebrate and vertebrate transposons hold potential for transgenesis and insertional mutagenesis in model organisms. Particularly, the availability of alternative transposon systems in the same species opens up new possibilities for genetic analyses. For example, piggyβac transposons can be mobilized in Drosophila in the presence of stably inserted P elements (Hacker et al., (2003), Proc Natl Acad Sci USA 100, 7720-5.). Because P element- and piggyBac-based systems show different insertion site preferences (Spradling et al. (1995), Proc Natl Acad Sci USA 92, 10824-30, Hacker et al., (2003), Proc Natl Acad Sci USA 100, 7720-5), the number of fly genes that can be insertionally inactivated by transposons can greatly be increased. P element vectors have also been used to insert components of the mariner transposon into the D. melanogaster genome by stable germline transformation. In these transgenic flies, mariner transposition can be studied without accidental mobilization of P elements (Lohe and Hard, (2002), Genetics 160, 519-26).

In vertebrates, three active transposons are currently known and used: the Tol2 element in medaka, and the reconstructed transposons Sleeping Beauty (SB) and Frog Prince (FP). A further interesting transposon system in vertebrates is the PiggyBac transposon system (Ding et al., Cell, 2005).

The Tol2 element is an active member of the hAT transposon family in medaka. It was discovered by a recessive mutation causing an albino phenotype of the Japanese medaka (Oryzias latipes), a small freshwater fish of East Asia. It was found that the mutation is due to a 4.7-kb long TE insertion into the fifth exon of the tyrosinase gene. The DNA sequence of the element, named To/2, is similar to transposons of the hAT family, including hobo of Drosophila, Acoi maize and Tam3 of snapdragon.

Sleeping Beauty (SB) is a Tc1/mariner-like element from fish and exhibits high transpositional activity in a variety of vertebrate cultured cell lines, embryonic stem cells and in both somatic and germ line cells of the mouse in vivo.

Also Frog Prince (FP) is a Tc1/mariner-like element that was recently reactivated from genomic transposon copies of the Northern Leopard Frog (Rana pipiens). An open reading frame trapping method was used to identify uninterrupted transposase coding regions, and the majority rule consensus of these sequences revealed an active transposase gene. Thus, in contrast to the "resurrection" procedure of SB, the relatively young state of genomic elements in Rana pipiens made it possible to ground the majority rule consensus on transposon copies derived from a single species. The SB and FP transposons are clearly distinct, sharing only −50% identity in their transposase sequences.

Transposons as the above, particularly Tol2, SB and FP, as well as piggyback (Ding et al., Cell 2005), do not interact and thus may be used as a genetic tool in the presence of others, which considerably broadens the utility of these elements. The preferences of these transposons to insert into expressed genes versus non-coding DNA, and preferences for insertion sites within genes may be substantially different. If so, different patterns of insertion of these transposon systems can be exploited in a complementary fashion. For instance, one could use different transposon systems to transfect several transgenes into cells sequentially, without accidental and unwanted mobilization of already inserted transgenes. In addition, the number of target loci that can be mutagenized by transposon vectors could dramatically increase by combining different transposon systems in genome-wide screens.

In addition to the variation in transpositional activity in hosts, and differences in target site specificity, distinct structural properties of various elements could also be advantageous in certain applications. For example, transposon insertions can be utilized to misexpress genes and to look for gain-of-function phenotypes Rorth, P. (1996, A modular misexpression screen in Drosophila detecting tissue-specific phenotypes. Proc Natl Acad Sci USA 93, 12418-22.) used a modified P element transposon that carried an inducible promoter directed out from the element to force expression of host genes near to transposon insertion sites and detected tissue specific phenotypes. A prerequisite of such an experimental setup is that the transposon IRs allow read through transcription/translation across the IRs.

As was already explained above DNA transposons have been developed as gene transfer vectors in invertebrate model organisms and more recently, in vertebrates too. They also rose to be strong rivals of the retroviral systems in human gene therapy. As said before the most useful transposable elements (TEs) for genetic analyses and for therapeutic approaches are the Class II TEs moving in the host genome via a "cut-and-paste" mechanism, due to their easy laboratory handling and controllable nature. Sleeping Beauty (hereinafter abbreviated as "SB") belongs to the Tc1/mariner family of the "cut-and-paste" transposons. These mobile DNA elements are simply organized, encoding a transposase protein in their genome flanked by the inverted terminal repeats (ITR). The ITRs carry the transposase binding sites necessary for transposition. Their activities can easily be controlled by separating the transposase source from the transposable DNA harboring the ITRs, thereby creating a non-autonomous TE. In such a two-component system, the transposon can only move by fr3/75 supplementing the transposase protein. Practically any sequence of interest can be positioned between the ITR elements according to experimental needs. The transposition will result in excision of the element from the vector DNA and subsequent single copy integration into a new sequence environment.

In general the transposon mediated chromosomal entry seems to be advantageous over viral approaches because on one hand transposons if compared to viral systems do not favour so much the active genes and 5' regulatory regions and thus are not so prone to mutagenesis, and on the other hand due to their special mechanism of chromosomal entry into of the gene of interest are more physiologically controlled.

SB already proved to be a valuable tool for functional genomics in several vertebrate model organisms (Miskey, C, Izsvak, Z., Kawakami, K. and Ivies, Z. (2005); DNA transposons in vertebrate functional genomics. Cell MoI. Life. Sci. 62: 629-641) and shows promise for human gene therapeutic applications (Ivies, Z. and Izsvak, Z. (2006). Transposons for gene therapy; Curr. Gene Ther. 6: 593-607). However for all of these applications the transpositional activity of the system is a key issue of usability and efficiency. Even though functional and valuable as commonly known and described as of today the transposase activity is likely to be one of the factors that still causes the SB system to reach its limits. Thus, a remarkable improvement of transpositional activity could breach current experimental barriers in both directions.

In aspects, a hyperactive variant of the SB10 transposase is used in the methods described herein. In particular aspects, the hyperactive variant may be that described by WO 2009/003671, incorporated herein by reference in its entirety. For example, a polypeptide selected from variants of SB10 transposase comprising an amino acid sequence differing from the sequence of native SB10 transposase according to SEQ ID NO:80 by 1 to 20 amino acids including at least one of the following mutations or groups of mutations selected from K14R, K13D, K13A, K30R, K33A, T83A, I100L, R115H, R143L, R147E, A205K/H207V/K208R/D210E; H207V/K208R/D210E; R214D/K215A/E216V/N217Q; M243H; M243Q; E267D; T314N; and G317E.

SEQ ID NO:80 is as follows:

```
MGKSKEISQD LRKKIVDLHK SGSSLGAISK RLKVPRSSVQ

TIVRKYKHHG TTQPSYRSGR RRVLSPRDER TLVRKVQINP

RTTAKDLVKM LEETGTKVSI STVKRVLYRH NLKGRSARKK

PLLQNRHKKA RLRFATAHGD KDRTFWRNVL WSDETKIELF

GHNDHRYVWR KKGEACKPKN TIPTVKHGGG SIMLWGCFAA

GGTGALHKID GIMRKENYVD ILKQHLKTSV RKLKLGRKWV

FQMDNDPKHT SKVVAKWLKD NKVKYLEWPS QSPDLNPIEN

LWAELKKRVR ARRPTNLTQL HQLCQEEWAK IHPTYCGKLV

EGYPKRLTQV KQFKGNATKY
```

"Mutation" or "mutations" is defined herein as the exchange of 1 or more amino acids of a known amino acid sequence by 1 or more other amino acids, respectively, and might—if specifically indicated—also a "group of mutations" or "groups of mutations". A "group of mutations" or "groups of mutations" are defined herein as the exchange of groups, e.g. 3 or 4, of amino acids from the original sequence by 3 or 4 other amino acids at the indicated positions, respectively. As a definition the following code is used to identify the above mutations. "XNo. Z" means that the amino acid "X" of the original amino acid sequence at position "No." is exchanged for amino acid "Z", whereas "XNo.Y/X'No.'Z'/X"No."Z'"" is intended to mean that in this mutation amino acids "X" at position "No.", "X'" in position "No.'" and "X"" in position "No."" are simultaneously exchanged for amino acid "Z", "Z'" and "Z"" respectively. If a "combination of mutations" is defined "//" is used to separate and indicate "simultaneous mutations" in this combination but otherwise is identical to a single slash "/".

In another typical aspect, the variants differ by at least 2, or by at least 1 to 8, typically by 2 to 7 of the above-listed mutations or groups of mutations, even more typically by at least 4 to 7 of the above-listed mutations or groups of mutations.

In another the variants of SB10 transposase are selected from variants comprising the following combination of mutations:

Variant 1: K14R//R214D/K215A/E216V/N217Q;
Variant 2: K33A/R115H//R214D/K215A/E216V/N217Q//M243H;
Variant 3: K14R/K30R//A205K/H207V/K208R/D210E//R214D/K215A/E216V/N217Q//M243H;
Variant 4: K13D/K33A//T83A//H207V/K208R/D210E//M243Q;
Variant 5: K13A/K33A//R214D/K215A/E216V/N217Q;
Variant 6: K33A/T83A//R214D/K215A/E216V/N217Q//G317E;
Variant 7: K14R/T83A/M243Q;
Variant 8: K14R/T83 A/I100L/M243Q;
Variant 9: K14R/T83A/R143L/M243Q;
Variant 10: K14R/T83A/R147E/M243Q;
Variant 11: K14R/T83A/M243Q/E267D;
Variant 12: K14R/T83A/M243Q/T314N;
Variant 13: K14R/K30R/100I7/A205K/H207V/K208R/D210E//R214D/K215A/E216V/N217Q//M243H;
Variant 14: K14R/K30R/R143I7/A205K/H207V/K208R/D210E//R214D/K215A/E216V/N217Q//M243H;
Variant 15: K14R/K30R/R147E//A205K/H207V/K208R/D210E//R214D/K215A/E216V/N217Q//M243H;
Variant 16: K14R/K30R//A205K/H207V/K208R/D210E//R214D/K215A/E216V/N217Q//M243H/E267D;
Variant 17: K14R/K30R//A205K/H207V/K208R/D210E//R214D/K215A/E216V/N217Q//M243H/T314N;
Variant 18: K14R/K30R//A205K/H207V/K208R/D210E//R214D/K215A/E216V/N217Q//M243H/G317E;
Variant 19: K14R/K33A/R1 15H//R214D/K215A/E216V/N217Q//M243H;
Variant 20: K14R/K30R/R147E//A205K/H207V/K208R/D210E//R214D/K215A/E216V/N217Q//M243H/T314N;
Variant 21: K14R/K30R/R143L//A205K/H207V/K208R/D210E//R214D/K215A/E216V/N217Q//M243H/E267D;
Variant 22: K14R/K30R/R143L//A205K/H207V/K208R/D210E//R214D/K215A/E216V/N217Q//M243H/T314N;
Variant 23: K14R/K30R/R143L//A205K/H207V/K208R/D210E//R214D/K215A/E216V/N217Q//M243H/G317E;

Variant 24: K14R/K33A/R115H/R143L//R214D/K215A/E216V/N217Q//M243H;
Variant 25: K14R/K33A/R115H/R147E//R214D/K215A/E216V/N217Q//M243H;
Variant 26: K14R/K33A/R115H//R214D/K215A/E216V/N217Q//M243H/E267D;
Variant 27: K14R/K33A/R115H//R214D/K215A/E216V/N217Q//M243H/T314N;
Variant 28: K14R/K33A/R115H//R214D/K215A/E216V/N217Q//M243H/G317E;
Variant 29: K14R/T83A/M243Q/G317E;
Variant 30: K13A/K33A/T83A//R214D/K215A/E216V/N217Q In a typical aspect, the transposase is the SB100X transposase, which is noted as Variant 27 in the list above.

Immune Cells

Prior to expansion and genetic modification of the immune cells described herein, a source of the immune cells is obtained from a subject. It will be understood that any source of immune cells may be used, and they may be autologous, allogeneic, syngeneic, or xenogeneic. In typical aspects, the immune cells are autologous or allogeneic.

For example, PBMCs can be obtained by any known method and then stimulated to become CIK cells, as described in, for example, WO 2016/071513, which is incorporated by reference in its entirety. The CIK cells can then be made into CIK CAR cells. Alternatively, T cells can be obtained by any known method and subsequently used to produce CAR-T cells.

Whether prior to or after genetic modification of the immune cells to express a CAR as described herein, the immune cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; U.S. Patent Application Publication No. 20060121005; and WO 2016/071513, incorporated herein by reference in their entirety.

Therapeutic Application

The CAR described herein and immune cells expressing the CAR can block VEGFR-2 and decrease its activation ability. Binding also activates the CAR-T cell or CIK CAR cell and stimulate immune-cell killing of the cancer cells. An advantage of these antibodies over drugs used for chemotherapy is that they are more specific for tumors that over-express VEGFR-2. Therefore, this might result in reduced general cell toxicity and cancer cell chemo-resistance. Additionally, the CAR described herein has tissue penetration ability due to their small size.

The present invention encompasses a cell (e.g., T cell) transduced with a lentiviral vector (LV) or transfected with a transposon. For example, the LV or transposon encodes a CAR that combines an antigen recognition domain of a specific antibody with an intracellular domain of CD3-zeta, CD28, 4-1 BB, or any combinations thereof. Therefore the transduced T cell elicits a CAR-mediated T-cell response, thus may aid in reducing tumor growth and inducing cell killing.

The invention provides the use of a CAR to redirect the specificity of a primary T cell to a tumor antigen—VEGFR-2. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3zeta, and a co-stimulatory signaling region.

In one aspect, the present invention includes a type of cellular therapy where T cells or CIK cells are genetically modified to express a CAR directed at VEGFR-2 and the CAR-T or CIK-CAR cell is infused to a recipient in need thereof. The infused cell is able to kill tumor cells in the recipient. Unlike antibody therapies, CAR-T and CIK-CAR cells are able to replicate in vivo resulting in long-term persistence that can lead to sustained tumor control.

In one aspect, the CAR-T or CIK-CAR cells described herein that target VEGFR-2 can undergo robust in vivo cell expansion and can persist for an extended amount of time. In another aspect, the CAR-T cells described herein evolve into specific memory T cells that can be reactivated to inhibit any additional tumor formation or growth. Without wishing to be bound by any particular theory, CAR-T cells may differentiate in vivo into a central memory-like state upon encounter and subsequent elimination of target cells expressing the surrogate antigen.

Further, the anti-tumor immunity response elicited by the CAR-modified T or CIK cells may be an active or a passive immune response. In addition, the CAR mediated immune response may be part of an adoptive immunotherapy approach in which CAR-modified T cells induce an immune response specific to the antigen binding moiety in the CAR. For example, VEGFR-2-specific CAR-T or CIK cells elicit an immune response specific against cells expressing VEGFR-2.

In one aspect, the antigen binding moiety portion of the CAR described herein is designed to treat a particular cancer expressing a particular antigen. For example, the CAR described herein is typically specific for VEGFR-2 and can be used to treat cancers and disorders associated with VEGFR-2, such as pancreatic cancer, ovarian cancer, bladder cancer, breast cancer, lung cancer, hepatocellular cancer, and colon cancer The CAR-modified T cells described herein may also serve as a type of vaccine for ex vivo immunization and/or in vivo therapy in a mammal. Typically, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (typically a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells described herein. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

In particular, the CAR-modified T cells described herein are used in the treatment of a VEGFR-2 expressing cancer. In certain aspects, the cells described herein are used in the treatment of patients at risk for developing a VEGFR-2 expressing cancer. Thus, the present invention provides methods for the treatment or prevention of a VEGFR-2 expressing cancer comprising administering to a subject in need thereof, a therapeutically effective amount of the CAR-modified T cells described herein.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are typically formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, typically $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain aspects, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In another aspect, the T cell compositions of the present invention are typically administered by i.v. injection. The compositions of T cells may be injected directly into a tumor, lymph node, or site of infection.

In certain aspects of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun 5:763-773, 1993). In a further aspect, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another aspect, the cell compositions of the present invention are administered following B-cell ablative therapy such as agents that react with CD20. e.g., Rituxan. For example, in one aspect, subjects may undergo standard treatment with high dose chemotherapy followed by peripheral blood stem cell transplantation. In certain aspects, following the transplant, subjects receive an infusion of the expanded immune cells described herein. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The typical daily dose is 1 to 10 mg per day although in some instances larger doses of up to 40 mg per day may be used (described in U.S. Pat. No. 6,120,766).

In aspects of the invention the compositions comprising the CAR-T of the invention may be stored refrigerated until use or frozen (then thawed) until required for use. The compositions may be formulated and provided as a "bank" of CAR-T cells for therapeutic treatment of VEGFR-2 cancers.

In embodiments of the invention, cells that are to be used for cell therapy are provided in a kit, and in some cases the cells are essentially the sole component of the kit. The kit may comprise reagents and materials to make the desired cell. In specific embodiments, the reagents and materials include primers for amplifying desired sequences, nucleotides, suitable buffers or buffer reagents, salt, and so forth, and in some cases the reagents include vectors and/or DNA that encodes a CAR as described herein and/or regulatory elements therefor.

In particular embodiments, there are one or more apparatuses in the kit suitable for extracting one or more samples from an individual. The apparatus may be a syringe, scalpel, and so forth.

In some cases of the invention, the kit, in addition to cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual. Kits may include instructions.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The following examples do not include detailed descriptions of conventional methods, such as those employed in the construction of vectors and plasmids, the insertion of genes encoding polypeptides into such vectors and plasmids, or the introduction of plasmids into host cells. Such methods are well known to those of ordinary skill in the art and are described in numerous publications including Sambrook, J., Fritsch, E. F. and Maniatis, T. (1989), Molecular Cloning: A Laboratory Manual, 2nd edition. Cold Spring Harbor Laboratory Press, which is incorporated by reference herein.

Without further description, it is believed that one of ordinary skill in the art can, using the preceding description and the following illustrative examples, make and utilize the compounds of the present invention and practice the claimed methods. The following working examples therefore, specifically point out the typical aspects of the present invention, and are not to be construed as limiting in any way the remainder of the disclosure.

Summary of Findings

VEGFR-2 is overexpressed in many types of human cancers such as breast, pancreatic, colorectal, and non-small-cell lung adenocarcinoma. Targeting VEGFR-2 by antibodies may slow tumor progression in certain animal models by decreasing/preventing angiogenesis. Antibodies were generated targeting VEGFR-2. AB1 is a camelid single domain antibody isolated from a whole cancer cell immunized llama library. The antibody binds specifically to VEGFR-2 with high affinity may inhibit the proliferation of VEGFR-2-expressing cancer cells in vitro.

The AB1 camelid antibody targets the extracellular domain of VEGFR2 and was generated by immunization of a llama with recombinant VEGFR2/Fc. A phage display library was generated and screened to identify an antibody with high binding affinity to VEGFR2. The selected antibody was expressed in the E. coli. BL21 (DE3) pT7 system. The purified antibody was characterized by SEC, LC-MS peptide mapping and ELISA.

CAR-T cells were engineered to express the camelid anti-VEGFR2 antibody (AB1) in combination with the CD28 and 4-1BB costimulatory molecules and the CD3 zeta chain. Co-incubation of anti-VEGFR2 CAR-T cells with VEGFR-2-expressing cell lines resulted in dose-dependent target cell toxicity as measured by LDH release. In addition, T cell activity was confirmed, as high levels of IL-2 and IFN-γ were detected in the cell culture media. These results suggest that anti-VEGFR2 CAR-T may be useful in directly targeting VEGFR2-expressing tumors.

Example 1: Generation of Anti-VEGFR-2 Antibodies

To generate camelid single domain antibodies targeting the extracellular domain of VEGFR-2, a llama was immunized with recombinant VEGFR-2/Fc. A phage display library was generated and screened to identify single domain antibodies with high binding affinity to VEGFR-2.

To generate human single domain antibodies targeting the extracellular domain of VEGFR-2, a human VH library was screened to identify single domain antibodies with high binding affinity to VEGFR-2.

A fusion partner sequence MKAIFVLKGSLDRDPE-FDDE (SEQ ID NO:71) was added to the N-terminus of SEQ ID NO:2 and SEQ ID NO: 11 (AB1 and AB2) sequences to increase the yield of the antibody by accumulating the expressed proteins in inclusion bodies and effectively simplifying protein purification and refolding processes.

Four antibodies were made and further studied. The selected antibodies were expressed in the E. coli. BL21 (DE3) pT7 system. Two of these antibodies (AB2 (SEQ ID NO:13) and AB3 (SEQ ID NO:21)) are based on a human antibody scaffold and two SEQ ID NO:7 and 27 (AB1 and AB4) are of llama origin. These antibodies displayed binding kinetics that are of sufficient quality to be considered potential candidates for specific VEGFR-2 binding (Table 1).

TABLE 1

Characterization of antibodies.

| Antibody | Origin | Kinetic Constants ka (1/Ms) | kd (1/s) | $K_D$ (M) | Rmax (RU) |
|---|---|---|---|---|---|
| AB2 SEQ ID NO: 13 | Human | $4.6 \times 10^4$ | 0.02 | $5 \times 10^{-7}$ | 1100 |
| AB3 SEQ ID NO: 21 | Human | $5.3 \times 10^4$ | 0.045 | $9 \times 10^{-7}$ | 1100 |
| AB1 SEQ ID NO: 7 | Llama | Approximately $6 \times 10^4$ | <0.01 | Approximately $8 \times 10^{-8}$ | ~700 |
| AB4 SEQ ID NO: 27 | Llama | $2 \times 10^4$ | 0.015 | $8 \times 10^{-8}$ | 370 |

Example 2: Human VEGFR-2/Fc Binders

The binding kinetics for the interactions of human SEQ ID NO: 13 (AB2) and SEQ ID NO:21 (AB3) and llama SEQ ID NO:7 (AB1) and SEQ ID NO:27 (AB4) to immobilized human and mouse VEGFR-2/Fc were determined by SPR using a Biacore 3000 system. 12,000 RUs of human VEGFR2/Fc (R&D Systems), 14,000 RUs of mouse VEGFR-2/Fc (R& D Systems), or 7500 RUs of BSA (Sigma) as a reference protein were immobilized on research grade CM5-sensorchips (Biacore), respectively. Immobilizations were carried out at a protein concentration of 50 µg/ml in 10 mM Acetate pH 4.5 using an amine coupling kit supplied by the manufacturer. All antibody samples were passed though a Superdex 75 column (GE Healthcare) to separate monomer forms subject to Biacore analysis.

In all instances, analyses were carried out at 25° C. in 10 mM HEPES, pH 7.4 containing 150 mM NaCl, 3 mM EDTA and 0.005% surfactant P20 at a flow rate of 40 µl/min. The surfaces were regenerated with 3-8 sec contact time of 10 mM HCl. Data were analyzed with BIAevaluation 4.1 software. All four antibodies showed mainly monomer peaks. (FIG. 1, size exclusion column chromatograms). Conditions for size exclusion column chromatography: Machine: AKTÄ FPLC (GE healthcare); Superdex 75 HR 10/30 column (Amersham, Cat. No. 17-1047-01, Id No. 9937116); Running buffer: HBS-EP (10 mM HEPES, 150 mM NaCl, 3 mM EDTA, pH7.4, 0.005% P20); and 4×HBS-E was diluted 4 times and 10% P20 surfactant was added to make final 0.005%. Sample volume: 200 µl. Pump speed: 0.5 ml/min.

Figure 2:
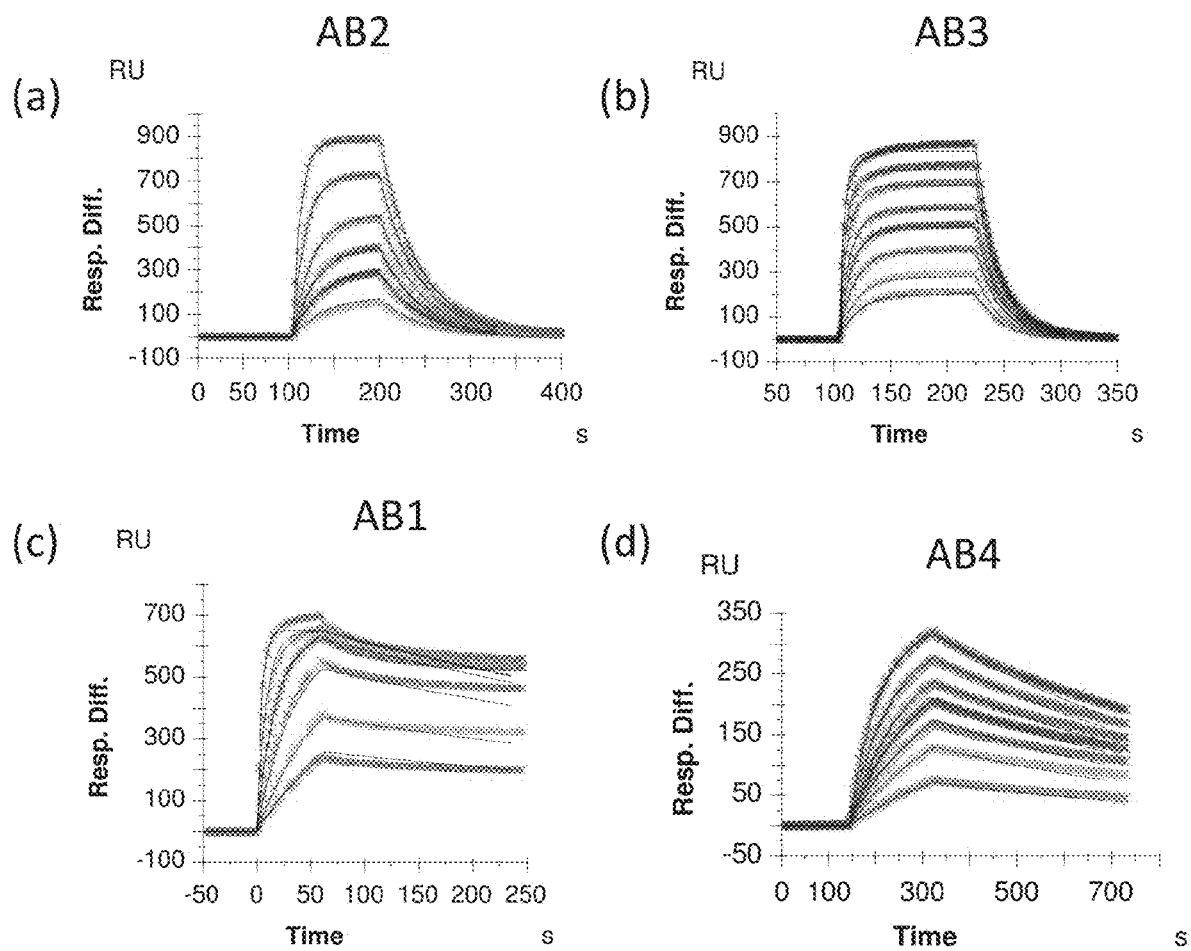
FIG. 2 shows binding of AB1 (SEQ ID NO:2), AB2 (SEQ ID NO:13), AB3 (SEQ ID NO:21), and AB4 (SEQ ID NO:27) to human VEGFR-2/Fc.

None of the antibodies showed binding to immobilized mouse VEGFR-2/Fc at the concentration of 150-200 nM, whereas all showed binding to immobilized human VEGFR-2/Fc (Table 1 and FIG. 2). These data indicate that the antibodies are species-specific. SEQ ID NO:7 (AB1) dissociates poorly on the SPR surface and complicated a direct fit of the sensorgram data (FIG. 2) to standard kinetic models. Therefore SEQ ID NO:7 (AB1) kinetic constants were estimated from transformed data shown in FIG. 3.

Example 3: Human & Llama Antibodies Binding to Human VEGFR-2/Fc

Sensorgram overlays showing the binding of (a) SEQ ID NO: 13 (AB2), (b) SEQ ID NO:21 (AB3). (c) SEQ ID NO:7 (AB1), (d) SEQ ID NO:27 (AB4) to immobilized human VEGFR-2/Fc at the concentrations of (a) 0.1, 0.2, 0.3, 0.5, 1 & 2p M, (b) 0.2, 0.3, 0.5, 0.75, 1, 1.5, 2 & 3 µM, (c) 0.15, 0.25, 0.5, 1, 2 & 4 µM, (d) 75, 150, 225, 300, 375, 525 & 750 nM, respectively, are shown in FIG. 2.

Example 4: Kinetic Constant Analyses of AB1 Binding to Human VEGFR-2/Fc

Figure 3:
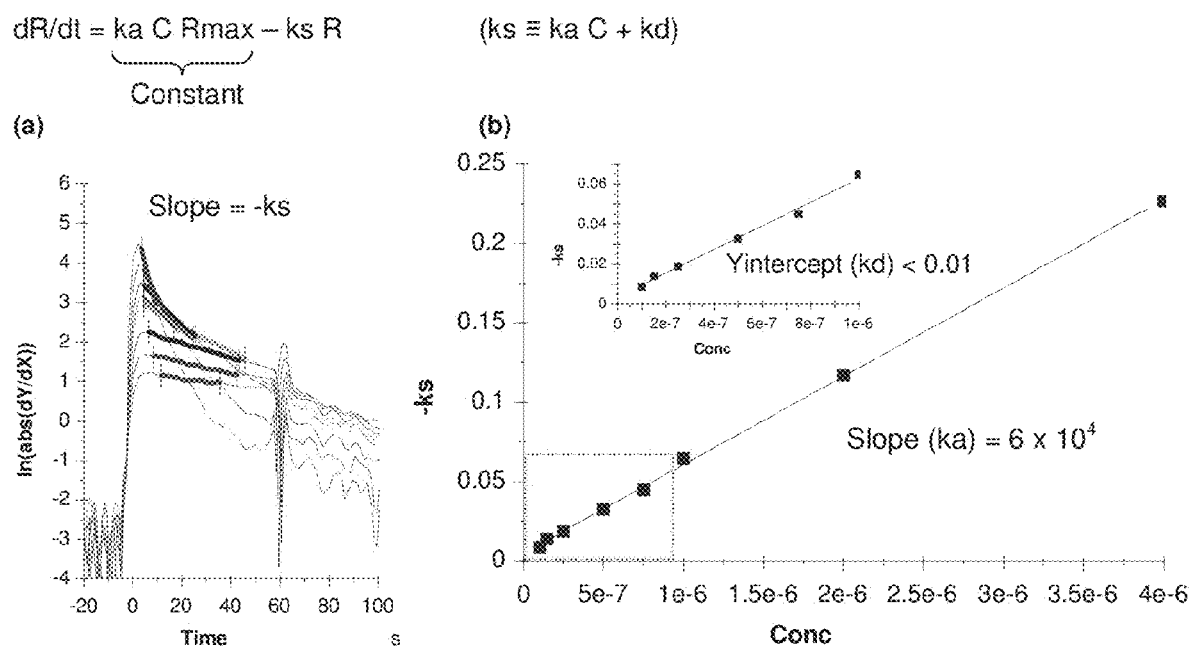
FIG. 3 shows binding kinetics for AB1 (SEQ ID NO:7) binding to human VEGFR-2/Fc.

Derivatized data of AB1 at the concentrations of 0.1, 0.15, 0.25, 0.5, 0.75, 1, 2, & 4 µM are shown in FIG. 3. Plot for Conc. vs -ks (incept showing the concentrations below 1 µM).

$$dR/dt = \underbrace{k_a\, C\, R_{max}}_{\text{constant}} - k_s\, R$$

$$(k_s = k_a\, C + k_d)$$

Example 5: Epitope Mapping

Figure 4:
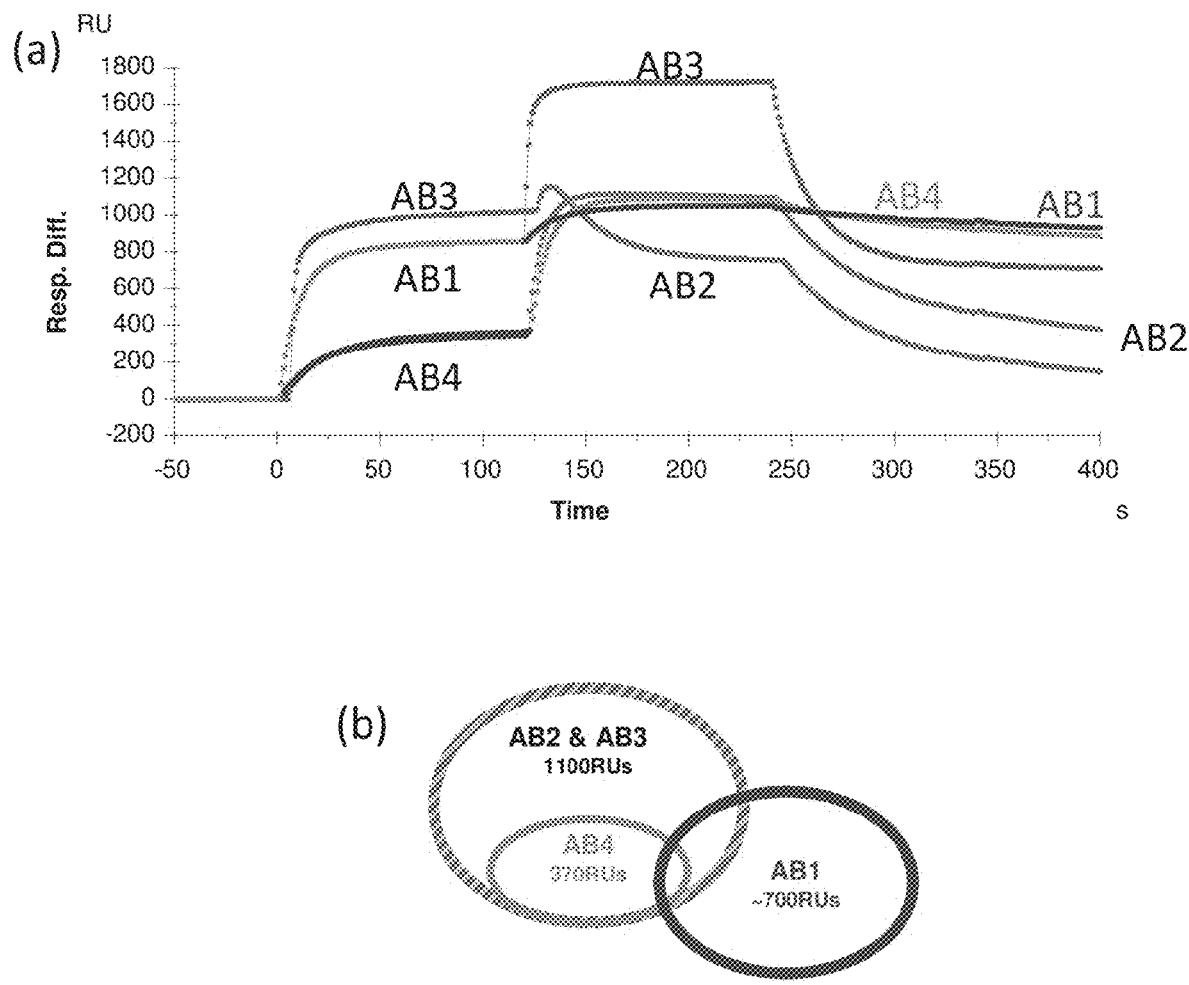
FIG. 4 shows (a) epitope mapping of the single domain anti-VEGFR-2 antibodies of the present invention to VEGFR-2 and (b) overlapping binding of epitopes for AB1 (SEQ ID NO:2), AB2 (SEQ ID NO:13), AB3 (SEQ ID NO:23), and AB4 (SEQ ID NO:27).

Two different antibodies were co-injected one after another at the concentrations >4×$K_D$. Results are shown in FIG. 4A and FIG. 4B. Clear overlap was seen with SEQ ID NO:13 (AB2), SEQ ID NO:21 (AB3) and SEQ ID NO:27 (AB4). Some overlap was seen with SEQ ID NO:7 (AB1).

Figure 7:
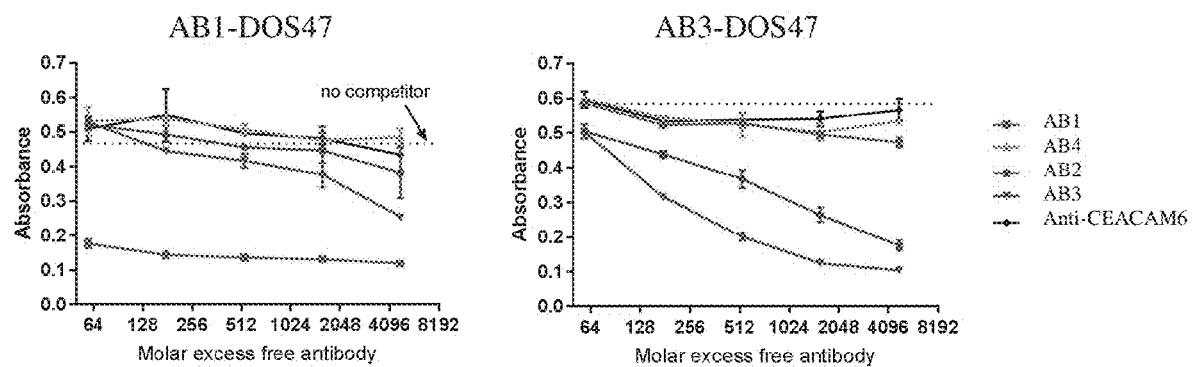
FIG. 7 shows AB1 (SEQ ID NO:9)-DOS47 (A) and AB3 (SEQ ID NO:23)-DOS47 (B) antibody-urease conjugates mixed with each of the four uncoupled antibodies (SEQ ID NO:7, 13, 21, and 27)(or anti-CEACAM6 as a negative control) at a variety of different molar ratios, and then tested for binding to VEGFR2/Fc coated on ELISA plates. Binding of each antibody-urease conjugate was inhibited by the corresponding uncoupled antibody. In addition, the AB3-urease conjugate was inhibited by uncoupled AB2 antibody, suggesting that the two human antibodies share at least partially overlapping epitopes. The uncoupled AB3 antibody also partially inhibited the binding of AB1-DOS47, although only at very high molar ratios.

Epitope information was also provided in competitive ELISA experiments (FIG. 7). The AB3 (SEQ ID NO:23)-urease conjugate was inhibited by uncoupled AB2 (SEQ ID NO:13) antibody, suggesting that the two human antibodies share at least partially overlapping epitopes. The uncoupled AB3 (SEQ ID NO:21) antibody also partially inhibited the binding of AB1 (SEQ ID NO:9)-DOS47, although only at very high molar ratios.

Example 6: VEGFR-2 Binding and Cross-Reactivity to VEGFR-1 and VEGFR-3

Figure 5:
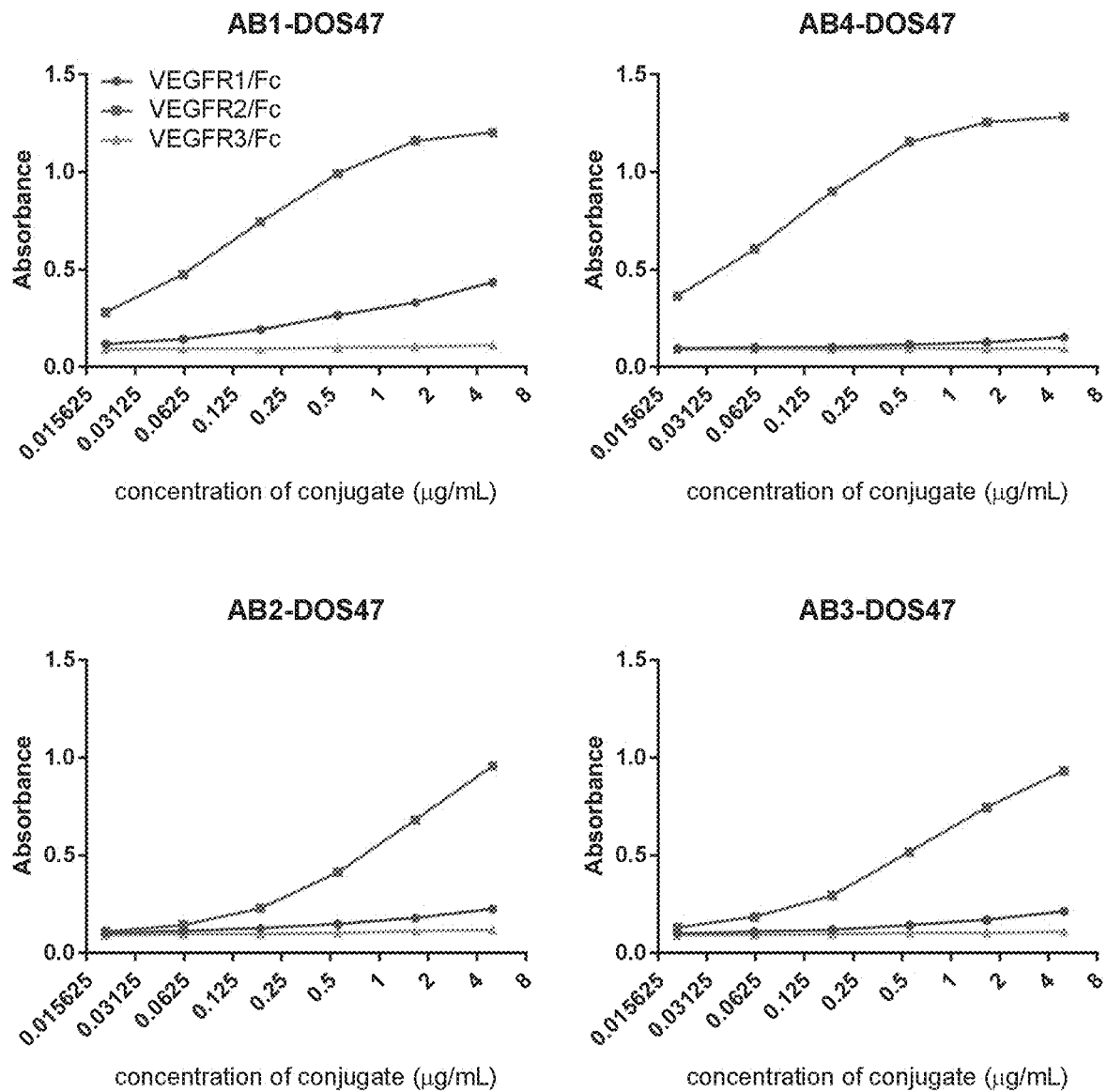
FIG. 5 shows antibody binding and cross-reactivity of AB1m (SEQ ID NO:9), AB2 (SEQ ID NO:13), AB3m (SEQ ID NO:23), and AB4 (SEQ ID NO:27) to VEGFR-1, VEGFR-2 and VEGFR-3. All four single domain antibodies were used to make urease ("DOS47") conjugates. These conjugates were tested by ELISA for their ability to bind the antigen VEGFR-2 and also their ability to cross-react with VEGFR-1 and VEGFR-3. All four antibody conjugates bind to recombinant VEGFR2/Fc, with the strongest binding observed with the llama antibody conjugates (consistent with $K_D$ values determined in FIG. 2). All antibodies show some cross-reactivity to VEGFR1/Fc. There was no detectable binding by any of the antibodies to VEGFR3/Fc.

All four single domain antibodies were used to make urease ("DOS47") conjugates. These conjugates were tested for their ability to bind the antigen VEGFR-2 and also their ability to cross-react with VEGFR-1 and VEGFR-3 (FIG. 5). All four conjugates were able to target VEGFR-2 with some cross-reactivity to VEGFR-1, but there was no detectable binding to VEGFR-3 observed. Results are shown for SEQ ID NO:9, SEQ ID NO:13, SEQ ID NO:23, and SEQ ID NO:27 (AB1, AB2, AB3, and AB4, respectively, comprising linkers).

Example 7: VEGF Competition Assays

Figure 6:
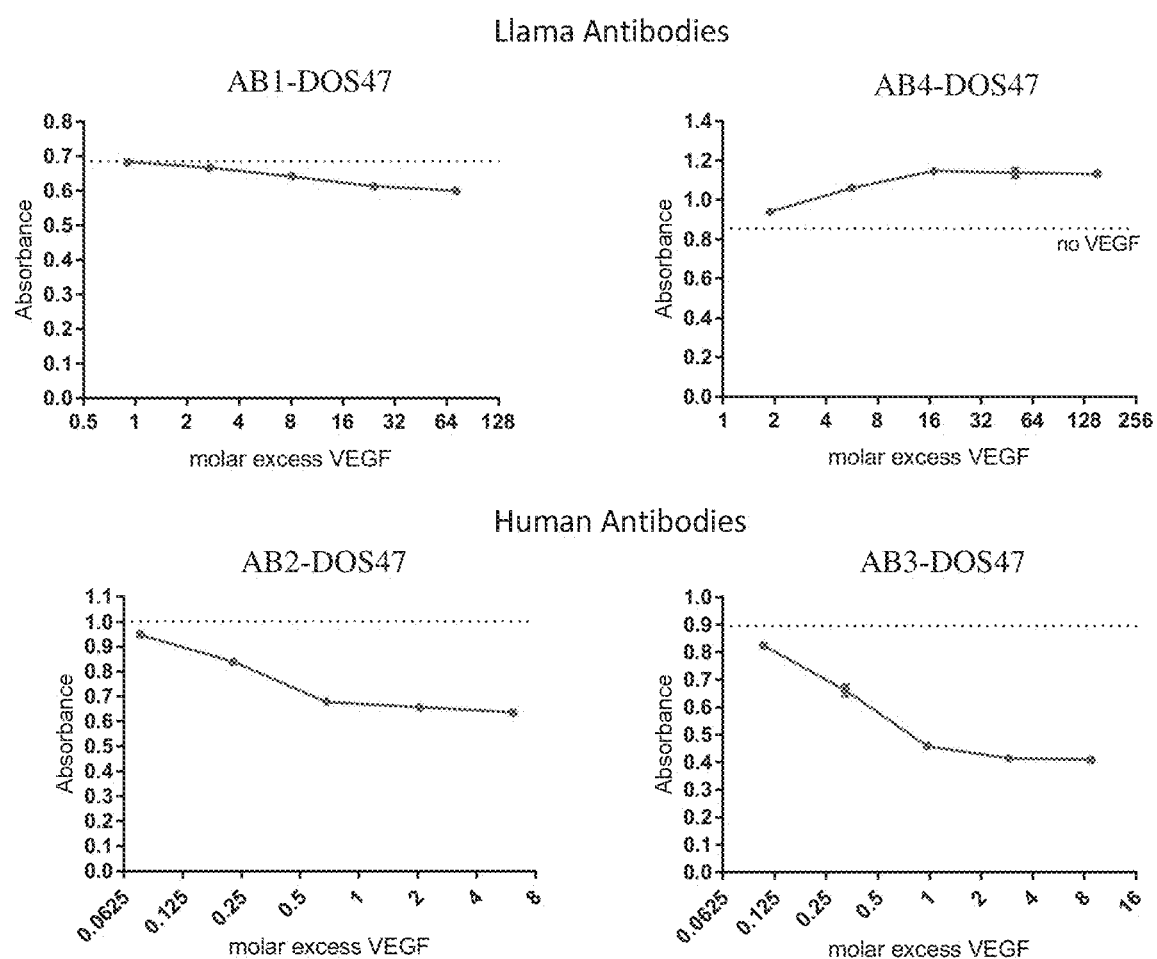
FIG. 6 shows the results of VEGF competition assays for AB1 (SEQ ID NO:2), AB2 (SEQ ID NO:13), AB3 (SEQ ID NO:23), and AB4 (SEQ ID NO:27). This was done to assess whether the antibodies recognize a region near the VEGF binding pocket. Antibody-urease conjugates were mixed with VEGF at a variety of different molar ratios, and then tested for binding to VEGFR2/Fc captured on ELISA plates. The binding of the two human antibody conjugates (AB2—(SEQ ID NO:13) & AB3—(SEQ ID NO:21) DOS47) to VEGFR2 was inhibited by VEGF, suggesting these antibodies and VEGF bind to overlapping sites. The binding of AB1-DOS47 was only minimally affected by VEGF, suggesting that the AB1 antibody and VEGF bind to distinct sites. Interestingly, the binding of AB4-DOS47 to VEGFR2 was enhanced by the presence of VEGF, suggesting that the AB4 antibody binds better to the VEGF/VEGFR2 complex than to VEGFR2 alone.

Urease conjugates were also tested for their ability to bind competitively with VEGF. This was done to assess whether the antibodies recognize a region near the VEGF binding pocket. An example of this analysis is provided in FIG. 6. From this, it can be seen that the binding of the two human antibody-urease conjugates (AB2—(SEQ ID NO:13) & AB3—(SEQ ID NO:23) DOS47) to VEGFR-2 was competitively inhibited by VEGF. However, maximum inhibition was found to be plateaued at ~40% for AB2—(SEQ ID NO: 13) DOS47 and ~60% for AB3—(SEQ ID NO:23) DOS47. This suggested that AB2 and AB3 only bind near the VEGF binding pocket. VEGF had a minimal effect on AB1—(SEQ ID NO:9) DOS47 complex binding to VEGFR2. Thus, it appears that AB1 binds a site remote from the VEGF binding pocket. The binding of AB4—(SEQ ID NO:27) DOS47 to VEGFR2 was enhanced by the presence of VEGF, suggesting that the AB4 antibody binds better to the VEGF/VEGFR2 complex than to VEGFR2 alone.

Example 8: Antibody Binding to VEGFR2 Expressed on 293/KDR Cells

Figure 8:
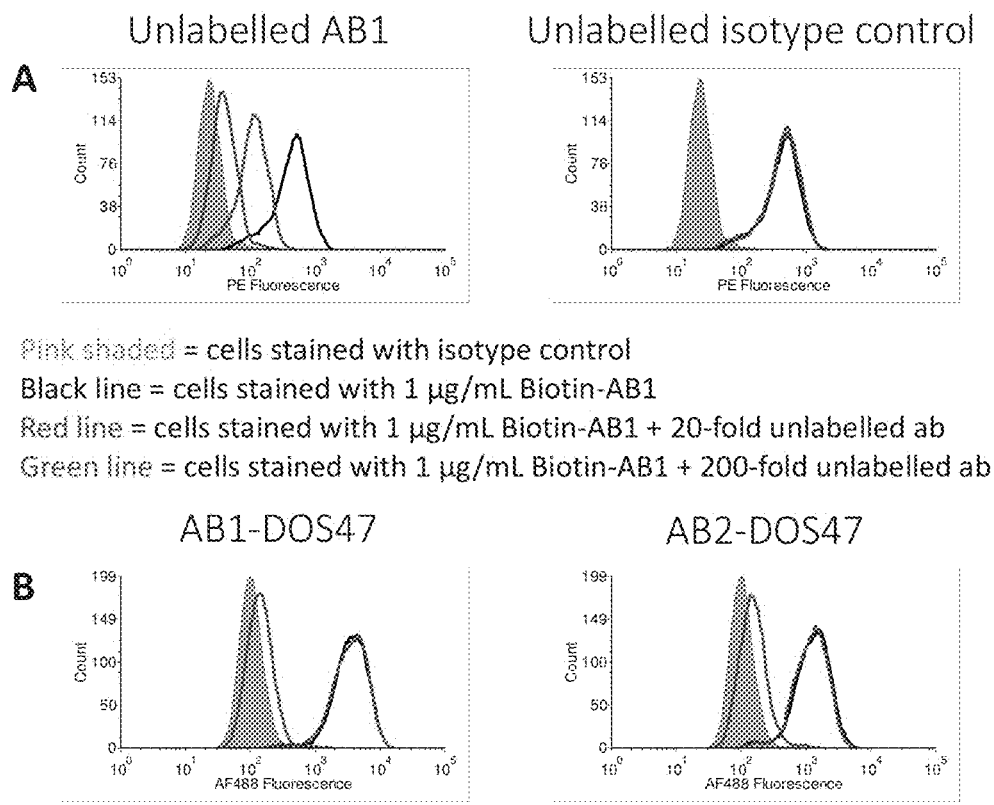
FIG. 8 shows binding of antibodies and antibody-urease conjugates to 293/KDR cells, which are HEK293 cells that have been transfected to stably express VEGFR2 (KDR). 293/KDR cells were stained with antibodies or antibody-urease conjugates and binding was detected by flow cytometry. Antibodies AB1 (SEQ ID NO:6) and AB2 (SEQ ID NO:18) bind to VEGFR2 expressed on 293/KDR cells.

Flow cytometry experiments were performed to test the binding of antibodies and/or antibody-urease conjugates to 293/KDR cells. 293/KDR cells are 293 cells that have been stably transfected to express human VEGFR2 (also called KDR). FIG. 8A shows the binding of biotinylated AB1 antibody (SEQ ID NO:6) to 293/KDR cells. This binding is inhibited by molar excess free AB1 antibody, but not an irrelevant antibody. FIG. 8B shows the binding of the AB1—(SEQ ID NO:6) urease conjugate and the AB2—(SEQ ID NO:18) urease conjugate to 293/KDR cells. The results shown in FIG. 8 confirm that the AB1 and AB2 antibodies described herein bind to VEGFR2 expressed on 293/KDR cells.

Example 9

V21-DOS47 is composed of a camelid single domain anti-VEGFR2 antibody (V21) and the enzyme urease (DOS47). The conjugate specifically binds to VEGFR2 and urease converts endogenous urea into ammonia, which is toxic to tumor cells. Previously, we developed a similar antibody-urease conjugate, L-DOS47, which is currently in clinical trials for non-small cell lung cancer. Although V21-DOS47 was designed from parameters learned from the generation of L-DOS47, additional work was required to produce V21-DOS47. In this study we describe the expression and purification of two versions of the V21 antibody: V21H1 (SEQ ID NO:3) and V21H4 (SEQ ID NO:6). Each was conjugated to urease using a different chemical cross-linker. The conjugates were characterized by a panel of analytical techniques including SDS-PAGE, SEC, Western blotting, and LC-MS$^E$ peptide mapping. Binding characteristics were determined by ELISA and flow cytometry assays.

To improve the stability of the conjugates at physiologic pH, the pIs of the V21 antibodies were adjusted by adding several amino acid residues to the C-terminus. For V21H4, a terminal cysteine was also added for use in the conjugation chemistry. The modified V21 antibodies were expressed in the E. coli BL21 (DE3) pT7 system. V21H1 was conjugated to urease using the heterobifunctional cross-linker succinimidyl-[(N-maleimidopropionamido)-diethyleneglycol] ester (SM(PEG)$_2$), which targets lysine residues in the antibody. V21H4 was conjugated to urease using the homobifunctional cross-linker, 1,8-bis(maleimido)diethylene glycol (BM(PEG)$_2$), which targets the cysteine added to the antibody C-terminus. V21H4-DOS47 was determined to be the superior conjugate as the antibody is easily produced and purified at high levels, and the conjugate can be efficiently generated and purified using methods easily transferrable for cGMP production. In addition, V21H4-DOS47 retains higher binding activity than V21H1-DOS47, as the native lysine residues are unmodified.

We have developed an antibody-drug conjugate (ADC) approach to suppress angiogenesis. Unlike most of the anti-angiogenic agents which interrupt the kinase signaling cascade by blocking the dimerization of VEGFR2 or by inhibiting kinase activity, our antibody-drug conjugate, V21-DOS47, kills VEGFR2-expressing cells by inducing cytotoxic activity at the target cells. Similar to our previous anti-tumor immunoconjugate, L-DOS47 (Tian el al., 2015), V21-DOS47 is composed of a camelid antibody and the enzyme urease (derived from jack beans. *Canavalia ensiformis*): the V21 antibody binds to VEGFR2, thus targeting the complex to VEGFR2 expressing cells, whereas the urease enzyme converts endogenous urea into ammonia in situ to induce cytotoxicity. Since VEGFR2 is not only expressed in the tumor vasculature but has also been identified on the surface of a variety of tumors (Itakura et al., 2000; Tanno et al., 2004; Guo et al., 2010), V21-DOS47 targets both VEGFR2$^+$ vascular endothelial cells and VEGFR2$^+$ tumor cells. The elevated local concentration of ammonia also neutralizes the acidic environment surrounding the tumor microvasculature, which is otherwise favorable to cancer cell growth (Wong et al., 2005). As urease is a plant product with no known mammalian homolog, it is likely to be immunogenic, although an auto-immune reaction is not expected. L-DOS47 is currently being tested in clinical trials and results show that anti-urease antibodies are formed, but no known severe immune toxicity is observed. The full impact of urease immunogenicity is still being studied.

One advantage of camelid antibodies is their relatively small size (approximately 15 kDa) compared to conventional immunoglobulins (approximately 150 kDa). This is particularly important when coupling antibodies to urease, as urease is a large protein with a molecular weight of 544 kDa. By using llama antibodies, multiple antibodies can be coupled to each urease molecule with a relatively minor increase in overall molecular weight. This allows for the generation of a high avidity therapeutic reagent that retains an acceptable biodistribution profile. Other benefits of camelid antibodies (De Genst et al., 2006; Maass et al., 2007; Harmsen and De Haard, 2007) are that they are easy to clone and express recombinantly (Arbabi Ghahroudi et al., 1997; Frenken et al., 2000), are generally more thermally and chemically stable than conventional IgG (van der Linden et al., 1999; Dumoulin et al., 2002), and they bind to epitopes that are not recognized by conventional antibodies (Lauwereys et al., 1998). In addition, they are not particularly immunogenic as human $V_H$ and camelid $V_HH$ domains share approximately 80% sequence identity (Muyldermans et al., 2001) and renal clearance is high (Cortez-Retamozo et al., 2002).

Antibody-urease conjugates are complex and large proteins: with multiple antibodies per urease, the molecular weight of the conjugate can reach 680 kDa. This provides a challenge to large-scale production. In our previous report, we described conjugation chemistry and separation procedures designed to address these challenges (Tian et al., 2015). In this study, we evaluated additional antibody production and conjugation chemistry methods to generate a novel antibody-urease conjugate, V21-DOS47.

In order to produce high affinity antibodies to VEGFR2, a llama was immunized with recombinant VEGFR2 and a $V_HH$ phage display library was generated. The V21 antibody was isolated by panning this library with recombinant VEGFR2. Additional amino acid residues were added to the C-terminus of the V21 antibody in order to fulfill multiple objectives: to optimize the antibody pI, to target antibody expression to bacterial inclusion bodies, and to provide a unique target for cross-linking chemistry. In this report we describe two versions of the V21 antibody, designated V21H1 and V21H4, and the different methods used to conjugate each antibody to urease. Both antibody-urease conjugates were characterized with a variety of analytical techniques, including size exclusion chromatography (to evaluate protein purity), SDS-PAGE (to determine the average number of antibodies conjugated per urease) and ESI mass spectrometry (to identify conjugation sites on both the antibody and urease). The effects of conjugation ratio were examined, and the binding of the two conjugates with the same conjugation ratio were compared. Binding to VEGFR2 expressed at the cell surface was confirmed by flow cytometry.

Material and Methods

Purification of High Purity Urease (HPU)

Crude urease (Cat #U-80, 236 U/mg) was purchased from BioVectra Inc. (Charlottetown, PE Canada). Prior to use in conjugation, crude urease was purified to remove jack bean matrix protein contaminants such as canavalin and concanavalin A. One million units of crude urease were dissolved in 430 ml of high purity (HP) water at room temperature. The solution was brought to pH 5.15 with 10% (v/v) acetic acid and then centrifuged at 9000rcf and 4° C. for 40 minutes. The urease-containing supernatant was cooled to 4° C. and fractionated by adding chilled ethanol to a final concentration of 25% (v/v) while maintaining the temperature at 0-8° C. The mixture was stirred overnight and then centrifuged at 9000rcf and 4° C. for 40 minutes. The pellet was resuspended in 150 ml of acetate-EDTA buffer (10 mM sodium acetate, 1 mM EDTA, 1 mM TCEP, pH 6.5) and then centrifuged at 4° C. and 9000rcf for 40 minutes. The supernatant was concentrated to 75 ml using a Minimate TFF system (Masterflex Model 7518-00 with a Minimate TFF capsule, MWCO 100 kDa), diafiltered 3 times with 200 ml of acetate-EDTA buffer, and then concentrated down to 100 ml. The diafiltered urease solution was collected, and the strained solution in the capsule and tubing connections was expelled from the system with 50 ml acetate-EDTA buffer and added to the collected solution (total volume ~50 ml). The ethanol fractionated urease solution was further purified by anion exchange chromatography using a Bio-Rad Biologic LP system. The urease solution was loaded at a flow rate of 3.5 ml/min onto a 35 ml DEAE column (DEAE Sepharose Fast Flow, GE Healthcare, Cat #17-0709-01) which was pre-equilibrated with 150 ml of IEC Buffer A (20 mM imidazole, 1 mM TCEP, pH 6.5). The column was washed with 100 ml of IEC Buffer A, followed by 80 ml of 40% Buffer B (Buffer A with 0.180M NaCl). The urease was eluted with 100% Buffer B at a flow rate of 3.5 ml/min and fractions with $A_{280}$>0.1 were pooled. The pooled fractions were concentrated to a target protein concentration of 6-8 mg/ml using a Minimate capsule with a 100 kDa MWCO membrane and then diafiltered against acetate-EDTA buffer (20 mM sodium acetate, 1 mM EDTA, pH 6.5). The high purity urease (HPU) was stored at −80° C. The yield from this purification protocol is typically >55% of the starting activity.

Expression of V21H1 and V21H4

Both antibodies were expressed in the *E. coli* BL21 (DE3) pT7 system with kanamycin as the selection antibiotic. Transformation of BL21(DE3) competent *E. coli* cells (Sigma, B2935-10×50 µl) was according to the manufacturer's instructions. One colony from a transformation plate was aseptically inoculated to 200 ml of LB broth (LB media EZ mix. Sigma Cat #L76581, 20 g/L) supplemented with 50 mg/L kanamycin. Cultures were incubated at 200 rpm and 37° C. Once the culture reached an $OD_{600}$ greater than 0.6, 50 ml of culture was transferred to four 2 L flasks, each containing 1 L of LB broth with 50 mg/L kanamycin. Flasks were incubated in a shaker incubator at 200 rpm and 37° C. Once the culture reached an $OD_{600}$ of 0.9-1.0, antibody expression was induced by the addition of 1 mM IPTG and overnight incubation at 200 rpm and 37° C. The cells were harvested by centrifugation into aliquots, one per 2 L culture.

Purification of V21H1

The majority of the V21H1 protein was expressed in the *E. coli* cytosolic solution, not in the inclusion bodies. An aliquot of cell pellet was lysed in 100 ml of lysis buffer (50 mM Tris, 25 mM NaCl, pH 6.5) by sonication in an ice-water bath for 10 minutes (Misonix 3000 sonicator, tip Part #4406; each sonicating cycle: sonicating 30 seconds, cooling 4 minutes, power 8). The lysate was centrifuged at 9000rcf and 4° C. for 30 minutes. In order to remove the most abundant bacterial matrix proteins, the supernatant was mixed with ice-cold ethanol to a final concentration of 10% (v/v) and incubated in an ice-water bath for 30 minutes, followed by centrifugation at 9000rcf and 4° C. for 30 minutes. The supernatant was mixed with ice-cold ethanol to a final concentration of 45% (v/v) and stirred in an ice-water bath for 60 minutes, followed by centrifugation at 9000rcf and 4° C. for 30 minutes, the pellet was resuspended in 200 ml of wash buffer (50 mM acetate, 0.1% Triton X-100, 1 mM DTT, 25 mM NaCl. pH 5.0). After centrifugation at 9000rcf and 4° C. for 30 minutes, the pellet was resuspended in 100 ml of SP Buffer A (50 mM acetate, 8M urea, pH 4.0) supplemented with 2 mM DTT, and filtered through a 0.45 µm filter. The filtered solution was loaded on to a 1 ml SP FF column (GE Healthcare, catalog #17-5054-01) with a peristatic pump at 2 ml/minute, and the column was then connected to an ACTA FPLC system (Amersham Bioscience, UPC-920). After washing the column with 10 ml of SP Buffer A at 1 ml/min, the V21H1 antibody was eluted by a gradient of 0-50% SP Buffer B (SP Buffer A with 0.7M NaCl) over 30 minutes at a flow rate of 1 ml/min. The $OD_{280}$ of the peak fraction was determined and the concentration was calculated with an extinction coefficient of 1.967/mg/ml. DTT was added to the SP column peak fraction to a final concentration of 1 mM and the pH of the solution was adjusted to 8-8.5 with 2M Tris-Base. The refolding of the antibody was performed by adding the pH adjusted SP peak fraction drop by drop to refolding buffer (100 mM Tris, 10 µM $CuSO_4$, pH 8.8) and continuous stirring at 4° C. until the refolding was completed. The refolding process was monitored by intact protein LC-MS. After refolding, the solution was centrifuged at 9000rcf and 4° C. for 30 minutes before loading on to a 1 ml QHP column. The column was connected to a FPLC system and washed with 10 ml of Q Buffer A (50 mM HEPES, pH 7.0) at a flow rate of 1 ml/min. The antibody was eluted by a gradient of 0-40% Q Buffer B (Q Buffer A with 0.7M NaCl) in 40 minutes at a flow rate of 1 ml/min. The peak fractions from 8 L of cell culture were pooled, concentrated to 2-4 mg/ml and dialyzed against 20 mM HEPES, pH 7.1 overnight (MWCO 5-8 kDa, volume ratio 1:50) at 4° C. The final V21H1 antibody solution was filtered through a 0.22 µm syringe filter and stored at 4° C.

Purification of V21H4

In contrast to V21H1, the majority of the V21H4 protein was expressed in the *E. coli* inclusion bodies. The cell pellet from each 2 L culture was resuspended in 100 ml of lysis buffer (50 mM Tris, 25 mM NaCl, pH 6.5) and mixed with lysozyme to a final concentration of 0.2 mg/ml. The cell suspension was incubated at room temperature for 30 minutes, then lysed by sonication in an ice-water bath for 10 minutes (Misonix 3000 sonicator, tip Part #4406; each sonicating cycle: sonicating 30 seconds, cooling 4 minutes, power 8). The lysate was centrifuged at 9000rcf and 4° C. for 30 minutes. The pellet was washed twice with 400 ml of Pellet Wash Buffer (50 mM Tris, 25 mM NaCl. pH 6.5, 1% Triton X-100, 2 mM DTT) and once with 50 mM of acetic acid containing 2 mM DTT. The pellet was resuspended in 100 ml of SP Buffer A (50 mM acetate, 8M urea, pH 4.0) supplemented with 2 mM DTI and centrifuged at 9000rcf and 4° C. for 30 minutes. The resulting supernatant was filtered through a 0.45 µm filter and loaded on to a 5 ml SP-XL column (GE Healthcare, catalog #17-1152-01) at a flow rate of 5 ml/min. After washing the column with 50 ml of SP Buffer A, the protein was eluted by a gradient of 0-50% SP Buffer B (SP Buffer A with 0.7M NaCl) over 30 minutes at a flow rate of 5 ml/min. Peak fractions were collected when $A_{280}$>700 mU. DTT was added to the pooled SP peak fraction to a final concentration of 1.0 mM and the pH was adjusted to pH 8.6-8.7 with saturated Tris base. Refolding was initiated by mixing the SP peak fraction with refolding buffer (50 mM Tris, 2M urea, 1.0 mM DTT pH 8.6-8.7). After stirring at room temperature for 2 hours, 1.2 mM cystamine was added to the refolding mixture. Refolding continued at room temperature and was monitored by RP-HPLC (Agilent 1100 system; ZORBAX-C3 column, PN883750-909; Solvent A: 0.025% (v/v) TFA in water; Solvent B: 0.025% TFA in acetonitrile; Gradient: 20-60% B over 30 minutes at a flow rate of 0.25 ml/min. 100 µl of sample was collected various time points and acidified by immediately adding 1.0 µl of neat formic acid. 30 µl of each sample was injected to the column to record the chromatogram). The resulting refolding mixture was centrifuged at 9000rcf and 4° C. for 30 minutes before loading to a 5 ml QHP column (GE Healthcare, 17-1154-01) at a flow rate of 5 ml/min. After washing the column with 50 ml of Q Buffer A (50 mM HEPES, pH 8.7), the protein was eluted by a gradient of 0-70% Q Buffer B (Q Buffer A with 0.7M NaCl). Peak fractions with $A_{280}$>700 mU were pooled. The Q peak fractions were pooled, concentrated to 6-10 mg/ml, and buffer exchanged with 10 mM HEPES, pH 7.1. The final V21H4 antibody solution was filtered through a 0.22 µm filter and stored at 4° C.

Conjugation of V21H1 to Urease 10 mg of V21H1 antibody was activated with cross-linker at an antibody to cross-linker molar ratio of 1:2.4 by adding 700 µl of SM(PEG)$_2$ (10.0 mg/ml in DMF) stock solution to the V21H1 antibody while vortexing. The reaction solution was incubated at room temperature for 90 minutes. The reaction was quenched by adding 300 mM of Tris buffer (pH 7.6) to a final concentration of 10 mM and incubating at room temperature for 10 minutes. The unconjugated, hydrolyzed and quenched cross-linker was removed with a 20 ml G25 desalting column pre-equilibrated with 50 mM Tris buffer containing 50 mM NaCl and 1 mM EDTA, pH 7.1. After removing the excess cross-linker, the desalting column fraction was pooled and a 100 µl sample was collected for intact protein mass spectrometric analysis and peptide mapping analysis to evaluate the activation sites on the V21H1 antibody. The remaining pooled fraction was chilled in an ice-water bath for 5 minutes. 20 mg of high purity urease (HPU) was thawed and incubated in another ice-water bath for 5 minutes. The chilled HPU solution was poured into the activated V21H1 antibody solution while stirring. The stirring continued in an ice-water bath for five minutes, and then the reaction solution was moved to a bench at room temperature. After the conjugation reaction solution was incubated at room temperature for 90 minutes, cysteine solution (200 mM in 300 mM Tris, pH 7-7.5) was added to a final concentration of 5 mM to quench the reaction. The reaction solution was concentrated down to approximately 4 ml by centrifugation in a 15 ml centrifuge filter (MWCO 100 kDa) at 4° C. and 2000 rcf. The resulting concentrated reaction solution was divided into three aliquots before SEC separation. The separation was performed by loading each aliquot of reaction solution to a Superose 6 100/300 GL column (GE) connected to an AKATA FPLC system. The protein was eluted by an isocratic flow at 0.5 ml/min with SEC buffer (50 mM NaCl, 0.2 mM EDTA, pH 7.2) and the major peak fractions of $A_{280}$>200 mU were pooled. The peak fractions from all three SEC separations were pooled and dialyzed against 1L of formulation buffer (10 mM histidine, 1% (w/v) sucrose, 0.2 mM EDTA, pH7.0). The resulting conjugate solution was filtered through a 0.22 µm filter and divided into 0.8 ml aliquots. Aliquots were stored at −80° C.

Conjugation of V21H4 to Urease 20 mg of V21H4 was mixed with TCEP (100 mM in 300 mM Tris buffer, pH 7-7.5) to a final concentration of 1.5 mM and incubated at room temperature for 60 minutes. The excess TCEP and the resulting cysteamine were removed by a 25 ml G25 desalting column using Tris-EDTA buffer (50 mM Tris, 1 mM EDTA, pH 7.1). The resulting desalting fraction was pooled in a 40 ml beaker and diluted with Tris-EDTA buffer to a total volume of 30 ml. The activation reaction was performed by quickly dispensing 0.420 ml of BM(PEG)$_2$ stock solution (10 mg/ml in DMF) into the V21H4 antibody solution in the beaker while stirring. After incubation at room temperature for 10 minutes, the reaction solution was transferred to a 200 ml Amicon diafiltration concentrator with a filter membrane (MWCO 5 kD) and mixed with Tris-EDTA buffer up to 100 ml. The excess cross-linker was removed by connecting the diafiltration concentrator to a 70 psi nitrogen source, and concentrated down to 20 ml while stirring. After 5 cycles of dilution and concentration, the diafiltration concentrator was detached from the nitrogen source and a 100 µl sample was collected to determine the antibody activation sites (using intact protein mass spectrometric analysis and peptide mapping analysis). Tris-EDTA buffer was added to the concentrator to dilute the solution up to the 50 ml marker. The concentrator with the activated V21H4 antibody was chilled in an ice-water bath for 10 minutes while stirring. After completely thawing at 4° C., 80 mg of HPU was incubated in another ice-water bath for 5 minutes and then poured into the activated V21H4 antibody solution in the concentrator while stirring in its ice-water bath. After stirring in the ice-water bath for 5 minutes, the concentrator with the reaction solution was moved to a lab bench and incubated at room temperature for 90 minutes. The conjugation reaction was quenched by adding cysteine (100 mM in 300 mM Tris, pH 7-7.5) to a final concentration of 5 mM. After quenching the reaction at room temperature for 5 minutes, the reaction solution was transferred to another container and the concentrator was cleaned and re-installed with a new filtration membrane (MWCO 100 kDa). The reaction solution was transferred back to the concentrator and formulation buffer (10 mM histidine, 1% (w/v) sucrose and 0.2 mM EDTA, pH 7.0) was added to the 160 ml marker. The concentrator was connected to a 10 psi nitrogen source and concentrated down to 20 ml while stirring. After the dilution-concentration cycle was repeated 4 times, the diafiltration concentrator was detached from the nitrogen source and the V21H4-DOS47 conjugate solution was transferred to a new container and diluted to 40 ml. The conjugate solution was filtered through a 0.22 µm filter and divided into 0.8 ml aliquots. The aliquots were stored at −80° C.

Size Exclusion Chromatography (SEC)

A Waters 2695 HPLC system with a 996 PAD was employed with Empower 2 software for data acquisition and processing. Chromatograms were recorded over 210-400±4 nm with the signal at 280 nm extracted for processing. Separation was performed on a Superose 6 100/300 GL column (GE). Proteins were eluted in 10 mM phosphate, 50 mM NaCl, 0.2 mM EDTA, pH 7.2. Separation was carried out with an isocratic flow at 0.5 ml/min after injection of a certain volume of neat samples. The column temperature was kept at room temperature while the sample temperature was controlled at 5±2° C.

SDS-PAGE

A Bio-Rad Mini Gel Protein Electrophoresis kit and a Bio-RAD Molecular Imager Gel Doc XR+ with ImageLab software were employed to analyze V21-DOS47 conjugation ratios. 10 µg of protein samples were mixed with 60 µl of protein gel loading buffer and the mixture was heated to 70° C. for 10 minutes. Denatured samples were loaded (10 uL/well) to a 4-20% Tris-Glycine gel (Invitrogen, REF #XP04200) and electrophoresis was performed at a constant voltage of 150V with current <40 mA until the electrophoresis front reached the gel bottom. After washing, staining and destaining, the gel image was scanned with the Gel Doc XR+ imager for analysis. SDS-PAGE was also used to calculate the average number of antibodies conjugated per urease molecule. This was determined by interrogating the intensities of the five bands in the main cluster (see Tian et al., 2015 for further details). All conjugation ratios reported are average values.

ELISA Assays

A 96-well plate was coated with 100 μL/well of goat anti-human IgG-Fc (Sigma, 5 μg/mL in PBS) at room temperature for 6 hours and then blocked with 200 μL/well of 3% BSA/PBS at 2-8° C. overnight. After washing 2× with T-TBS (50 mM Tris, 0.15 M NaCl, pH 7.6, containing 0.05% Tween-20), 100 μL/well of VEGFR1/Fc, VEGFR2/Fc or VEGFR3/Fc (R&D Systems, 0.25 μg/mL in TB-TBS (0.1% BSA/T-TBS)) was added and the plate was incubated at room temperature for 1 hour with gentle shaking. After washing 3× with T-TBS, 100 μL/well of antibody-urease conjugate or biotinylated antibody dilutions (in TB-TBS) were added and the plate was incubated at room temperature for 2 hours with gentle shaking. For antibody-urease conjugates, plates were washed 3× with T-TBS, 100 μL/well of rabbit anti-urease (1/6,000 or 1/10,000-fold dilution in TB-TBS, Rockland) was added and the plate was incubated at room temperature for 1 hour with gentle shaking. For all samples, the plate was washed 3× with T-TBS and 100 μL/well of goat anti-rabbit-AP (1/8,000-fold dilution in TB-TBS, Sigma) was added to detect antibody-urease conjugates or streptavidin-alklaline phosphatase (0.5 μg/mL in TB-TBS, Sigma) was added to detect biotinylated antibodies, and the plate was incubated at room temperature for 1 hour with gentle shaking. After washing 3× with T-TBS, 100 μL/well of substrate (4-nitrophenyl phosphate disodium salt hexahydrate, Fluka, 1 mg/mL in diethanolamine substrate buffer, Pierce) was added to each well and incubated at room temperature for 5-15 minutes with gentle shaking. The absorbance at 405 nm ($A_{405}$) of each well was acquired by scanning the plates with a UV-Vis spectrophotometer.

Urease Activity Assay

Urease catalyzes the hydrolysis of urea to ammonia. One unit of urease activity is defined as the amount of enzyme which liberates one micromole of ammonia per minute at 25° at pH 7.3. V21H4-DOS47 samples were diluted in sample dilution buffer (0.02M potassium phosphate containing 1 mM EDTA and 0.1% (w/v) BSA, pH 7.3). 100 μl of the diluted sample was mixed with 2.00 ml of 0.25M urea (in phosphate buffer containing 0.3M sodium phosphate and 0.5 mM EDTA, pH 7.3), and incubated at 25±0.1° C. for five minutes, then the reaction was quenched by adding 1.00 ml of 1.0N HCl. To determine the concentration of ammonium ion produced in the enzyme reaction solution, 100 μl of the quenched reaction solution was mixed with 2.00 ml of phenol solution (0.133M phenol containing 0.25 mM sodium nitroferricyanide) in a 15 ml testing tube. After 30 seconds, 2.50 ml of NaOH—NaOCL solution (0.14N NaOH containing 0.04% sodium hypochlorite) was added to the testing tube, mixed, and incubated at 37° C. for 15 minutes. The absorbance of the solution was determined at 638 nm with the reagent reaction solution (without sample) as the blank. The urease enzyme activity was calculated according to the following equation: $U/ml=D\times(A\times Tc\times Te)/(5\times E\times Sc\times Se)$ where A=absorbance at 638 nm, Tc=total volume of color reaction (4.60 ml), Te=total volume of enzyme reaction (3.10 ml), E=molar extinction coefficient of indophenol blue per assay condition ($20.10$ $mM^{-1}\cdot cm^{-1}$), Sc=sample volume for color reaction (0.10 ml), Se=sample volume for enzyme reaction (0.10 ml) and D=dilution time. The protein concentration of each sample was determined with a Sigma total protein kit (TP0200) following the manufacturer's instructions. Urease activity/mg of conjugate was calculated by dividing the urease activity (U/ml) by the amount of protein tested (mg/ml). Specific urease activity was calculated by dividing the activity/mg conjugate by the proportion of the conjugate's mass which was composed of urease.

Western Blot

V21H4-DOS47 test samples and controls were resolved by SDS-PAGE gel electrophoresis and then transferred to a nitrocellulose membrane using a Bio-Rad blot kit. 1.2 μg of HPU and 4.0 μg of V21H4 as controls, and 2.0 μg of V21H4-DOS47 samples were mixed with 60.0 μl of protein gel loading buffer. The resulting sample mixtures were denatured by heating to 60° C. for 10 minutes and 10 μl of each sample was loaded per lane. Duplicate blots were made from gels run in parallel for urease and V21H4 antibody probing. For urease detection, a rabbit anti-urease IgG (Rockland) was used. To detect the V21H4 antibody, a rabbit anti-llama IgG (ImmunoReagents Inc.) was used. A goat anti-rabbit IgG conjugated to AP (Sigma) was used as the secondary visualization antibody. Final development of the Western blots was performed with AP buffer containing NBT/BCIP.

Mass Spectrometry

A Waters Xevo G2 QTOF mass spectrometer and an Acquity UPLC system H class were employed for all mass spectrometry analyses. A lock mass of 785.8426 Da was applied for real time point to point mass calibration. LC-MS data acquisition was controlled by Masslynx V4.1 software.

Intact Protein Mass Spectrometry Analyses

Cross-linker activated antibody samples were reacted with 5 mM cysteine at room temperature for 30 minutes, diluted to 0.5-1 mg/ml in water, and acidified by adding neat formic acid to a final concentration of 1% (v/v). A BEH300 C4 (1.7 μm, 2.1×50 mm) column was used. The column temperature was set at 60° C. and Solvent A (0.025% v/v TFA in water) and Solvent B (0.025% TFA in acetonitrile) were used for UPLC separation. The UPLC was performed with a flow rate of 0.15 ml/min with a gradient from 20 to 60% Solvent B over 30 minutes. LC-MS TIC (total ion counts) data acquisition was carried out in an M/Z range of 500-3500 Da in resolution mode with a scan rate of 0.3/s, capillary voltage 3.0 kV, sample cone voltage 40V, extraction cone voltage 4.0 kV. Ion source temperature was set at 100° C. and desolvation temperature was set at 350° C. Desolvation gas flow rate was 600 L/hour. A real time lock mass TIC raw data set (scan/20 s) was acquired with 100 fmole/μl Glu-Fib B at a flow rate of 6.0 μl/min. Mass spectrometric raw data were processed with BioPharmalynx software (v1.2) in intact protein mode with a resolution of 10000. Mass match tolerance was set at 30 ppm, and the protein sequence of each antibody containing one disulfide bond was input as the match protein for protein match searches.

Tryptic Digestion of V21H1-SM(PEG)$_2$-Cys and V21H4-BM(PEG)$_2$-Cys

The cross-linker activated antibody samples were reacted with 10 mM cysteine at room temperature for 30 minutes and then diluted to 0.5 mg/ml with 100 mM ammonia hydrogen carbonate. Neat acetonitrile was added to the diluted sample solution to a final concentration of 20% (v/v). Trypsin/Lys-C Mix (Promega, Ref #V507A) was added at a protein:protease ratio of 20:1 and digested at 37° C. for 16-20 hours. DTT was added to the digested sample to a final concentration of 10 mM and samples were incubated at 37° C. for 30 minutes to reduce the core disulfide bond. The digestion was stopped by adding neat formic acid to 1% (v/v) before mass spectrometry analysis.

Tryptic Digestion of V21H4-DOS47

100 µg of V21H4-DOS47 was mixed with DTT to a final concentration of 10 mM and neat acetonitrile was added to a final concentration of 20% (v/v). To reduce the disulfide bond and denature the conjugated proteins, the sample mixture was heated at 60° C. for 30 minutes. The denatured protein precipitate was pelleted by centrifugation at 16000rcf at room temperature for 5 minutes. 5.0 µl of 0.20M iodoacetamide and 100 µl of water were added to the pellet then mixed by vortexing. The suspension was centrifuged at 16000rcf at room temperature for 5 minutes and the supernatant was discarded. The resulting pellet was dissolved in 100 µl of Tris-guanidine buffer (4M guanidine chloride, 50 mM Tris, 10 mM $CaCl_2$ and 10 mM iodoacetamide, pH 8.0). After this alkylation reaction was performed at room temperature in the dark for 30 minutes, the reaction was quenched with 5 mM DTT. The resulting solution was diluted 4 times with Tris buffer (50 mM Tris, 10 mM $CaCl_2$ pH 8.0). Trypsin/LysC mix was added to the diluted sample solution at a protein:protease ratio of 25:1. After the digestion was performed at 37° C. for 16-20 hours, the reaction was stopped by adding neat formic acid at a final concentration of 1% (v/v).

LC-$MS^E$ Peptide Mapping of V21H1-SM(PEG)$_2$-Cys, V21H4-BM(PEG)$_2$-Cys, and V21H4-DOS47 Tryptic Digests A BEH300 C18 (1.7 µm, 2.1×150 mm) column was used for UPLC separation. The column temperature was set at 60° C. Solvent A (0.075% v/v formic acid in water) and Solvent B (0.075% formic acid in acetonitrile) were used for peptide elution. UPLC was performed with a flow rate of 0.15 mL/min. A gradient of 0 to 30% solvent B in 50 minutes was used for the separation of the tryptic digests of V21H1-SM(PEG)$_2$-Cys and V21H4-BM(PEG)$_2$-Cys samples. For the tryptic digests of V21H4-DOS47, a gradient of 0 to 45% Solvent B in 150 minutes was used. LC-$MS^E$ TIC (total ion counts) data acquisitions were carried out in an M/Z range of 50-2000 Da in resolution mode with a scan rate of 0.3/s, capillary voltage 3.0 kV, sample cone voltage 25 V, and extraction cone voltage 4.0 kV. Ion source temperature was set at 100° C. and desolvation temperature was set at 350° C. Desolvation gas flow rate was 600 L/hour. A real time lock mass TIC raw data set (scan/20 s) was acquired with 100 fmole/µL Glu-Fib B at a flow rate of 3.0 µL/min. With the instrument setup, two interleaved scan functions are applied for data acquisitions. The first scan function acquires MS spectra of intact peptide ions in the sample while applying no energy to the collision cell. The second scan function acquires data over the same mass range; however, the collision energy is ramped from 20 to 60 eV. This scan is equivalent to a non-selective tandem mass spectrometric (MS/MS) scan, and allows for the collection of $MS^E$ fragment spectra from the ions in the preceding scan. The high energy collision induced fragmentation randomly cleaves peptide backbone bonds. For each C—N peptide backbone bond cleaved, the amino-terminal ion generated is called the "b" ion and the C-terminal ion generated is called the "y" ion. In Tables 1-3, the column entitled "MS/MS b/y Possible" indicates the theoretical maximum number of b and y ions that would be produced for each peptide if all peptide bonds in the protein were equally likely to be broken. The column entitled "MS/MS b/y Found" indicates the actual number of b and y ions identified for each peptide. The identification of b/y ions provides unambiguous confirmation of peptide identity. Mass spectrometric raw data were processed with BiopharmaLynx software (v 1.2) in peptide map mode with a resolution of 20000. A lock mass of 785.8426 Da was applied for real time point to point mass calibration. The low energy MS ion intensity threshold was set at 3000 counts and the $MS^E$ high energy ion intensity threshold was set at 300 counts. Mass match tolerances were set at 10 ppm for MS and at 20 ppm for $MS^E$ data sets. Peptides with 1 missed cleavage site were included in mass match searching. V21H1, V21H4 and urease (Uniprot P07374) protein sequences were respectively input into the sequence library for peptide matching/identification. Variable modifiers including Deamidation N, Deamidation succinimide N, Oxidation M, +K, +Na, and Carbamidomethyl C (for alkylated cysteine) were applied for peptide map analysis. SM(PEG)$_2$-Cys (429.1206 Da) was set as a variable modifier to identify the activation sites of V21H1 conjugation, whereas BM(PEG)$_2$-Cys (431.1362 Da) was input as a variable modifier to identify the activation sites of V21H4 conjugation. For the V21H4-DOS47 tryptic digests, GGGEEDDGC-BM(PEG)$_2$ (SEQ ID NO:72) (1145.3453 Da) was set as a variable modifier to identify the conjugation sites on urease.

Flow Cytometry 293 or 293/KDR cells were detached from flasks using non-enzymatic cell dissociation buffer (Sigma). Cells were centrifuged at 300×g for 5 minutes and then resuspended in staining buffer at $10^6$ cells/mL (PBS with $Ca^{2+}$ and $Mg^{2+}$, 0.02% $NaN_3$, 2% FBS). 100 µL of cells was added to wells of a 96-well plate. The plate was centrifuged at 350×g for 4 minutes, buffer removed, and then cells were resuspended in 50 µL of antibody-urease conjugate or biotinylated antibody (diluted in staining buffer) and then incubated at 2-8° C. for 1 hour. For cells stained with antibody-urease conjugates, cells were washed 3× with staining buffer and then resuspended in mouse anti-urease (Sigma, cat #U-4879) at 5.8 µg/mL (diluted in staining buffer) incubated for 30 minutes at 2-8° C. For all samples, cells were washed 3× with staining buffer and then resuspended in AF488-anti-mouse IgG (Jackson, cat #115-545-164) at 3 µg/mL (diluted in staining buffer) for antibody-urease samples or with PE-SA (Biolegend, cat #405204) at 133 ng/mL (diluted in staining buffer) for biotinylated antibodies. All cells were incubated for 30 minutes at 2-8° C. in the dark, washed 3× with staining buffer, then resuspended in 1% paraformaldehyde (diluted in PBS). The plate was incubated for 15 minutes at room temperature, covered with tin foil. The plate was then centrifuged as above, paraformaldehyde removed, and the cells were resuspended in staining buffer. The plate was covered in tin foil and stored at 2-8° C. until analysis using a Guava flow cytometer and guavaSoft software (Millipore). S/N values are the ratio of V21H4-DOS47 binding to 293/KDR cells vs V21H4-DOS47 binding to 293 cells or the ratio of biotin-V21H4 vs biotin-isotype control antibody (anti-CEACAM6) binding to 293/KDR cells.

Results

Production and Purification of V21H1

When generating single-domain antibodies for immunoconjugate drugs, high purity antibodies must be produced at high yield and with controllable processes, including expression, protein refolding, and purification. Other considerations include the following: the pI of the antibody should be such that the antibody-conjugate is stable and soluble at physiologic pH, the properties of the antibody should be suitable for the conjugation chemistry, and the modifications of the antibody residues during conjugation reactions should not compromise the affinity of the antibody binding to its antigen.

The V21 camelid antibody has 122 amino acids (SEQ ID NO:2). Eleven amino acids were added to the C-terminus of the V21 antibody in order to generate V21H1 (SEQ ID NO:3). By adding these amino acids, the pI of the antibody was changed from 8.75 to 5.44, as required for conjugate stability and solubility. The hetero-bifunctional chemical cross-linker SM(PEG)$_2$ reacts with amine and sulfhydryl groups and was selected for use in conjugating V21H1 to urease:

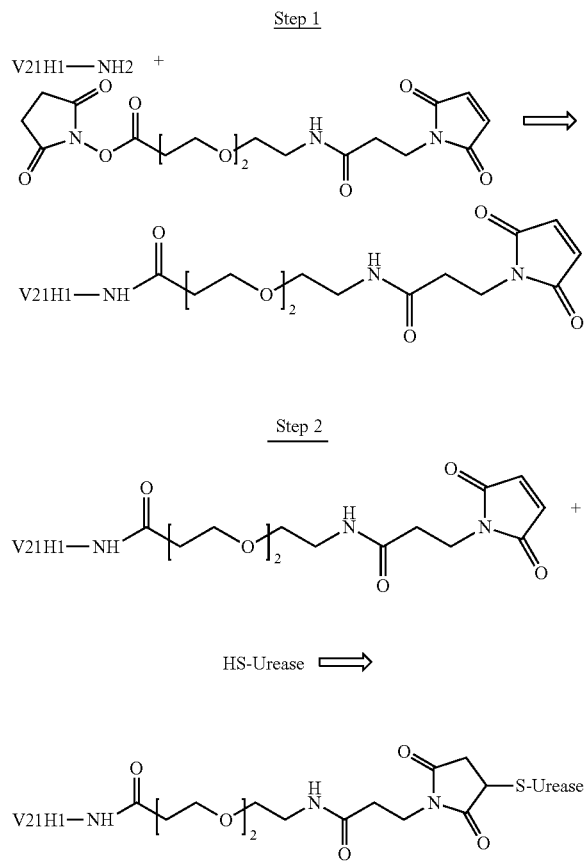

Step 1 is the activation of the antibody using SM(PEG)$_2$. Step 2 conjugates the activated antibody to urease.

There are five lysine residues in the core V21 sequence, two of which (Lys$_{66}$ and Lys$_{101}$) are located in the CDR2 and CDR3 sequences respectively. As these amino acids could be modified by the amine conjugation chemistry utilized by SM(PEG)$_2$, potentially altering antibody activity, two extra lysine residues were added to the antibody C-terminus to minimize this probability.

V21H1 was expressed primarily in the cytosolic solution of BL21(DE3) bacteria, with virtually no expression in inclusion bodies. Therefore, after cell lysis, the antibody was separated from bacterial proteins by ethanol crystallization and cation-exchange chromatography. After antibody refolding, the native antibody was further purified by anion-exchange chromatography. To confirm that the molecular mass of the purified antibody matched the designed protein sequences, LC-MS intact protein analysis was performed. No impurity proteins were detected from the LC-MS TIC chromatograms and the detected molecular mass of V21H1 matched the theoretical value calculated from its protein sequence within 30 ppm mass match error (data not shown). However, the yield of purified V21H1 was very low (4-6 mg/L of culture) and the purification processes used are not suitable for large scale cGMP production.

Cross-Linker Activation of V21H1

V21H1 was activated by SM(PEG)$_2$ at pH 7.0 using conditions previously found to be optimal for activation of AFAIKL2 antibody with SIAB in the production of the antibody-urease conjugate L-DOS47. Since the NHS-ester reaction is the same for SIAB and SM(PEG)$_2$ and the LC-MS spectra are similar for AFAIKL2 and V21H1 reaction products (data not shown), these conditions should also be optimal for activation of V21H1 with SM(PEG)$_2$.

Figure 9:
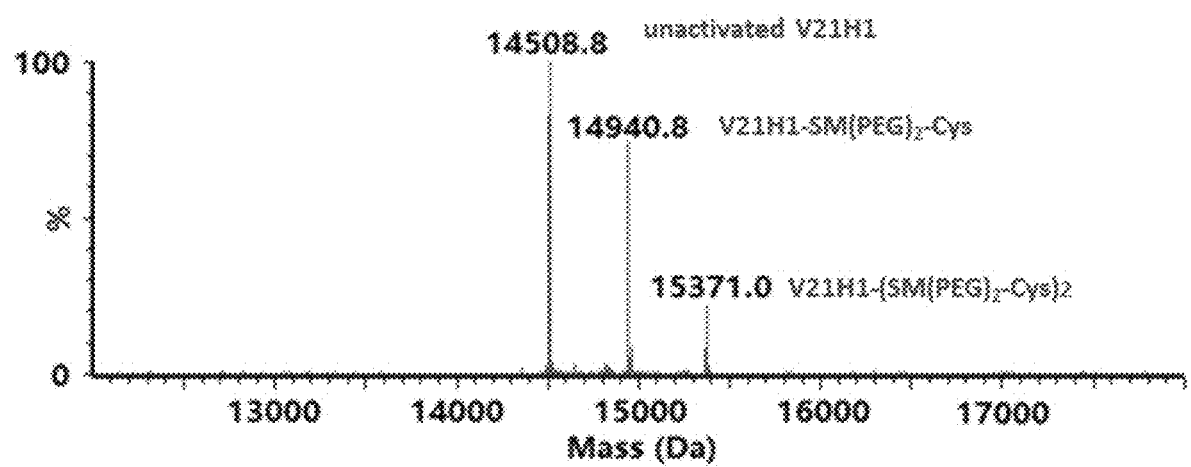
FIG. 9 shows a deconvoluted mass spectrum of the V21H1 (SEQ ID NO:3) antibody after activation by crosslinker and linkage to cysteine showing the distribution of non-activated antibody, antibody activated by one crosslinker and antibody activated by two cross-linkers.

Only the NHS-ester group of SM(PEG)$_2$ can react with V21H1. The two cysteine residues in the V21H1 antibody form a disulfide bond and are thus unavailable to react with the maleimido end of the cross linker. The primary amines from the antibody N-terminus and the lysine residues from the protein sequence can all potentially react with the NHS-ester of the cross-linker. The maleimido end of the antibody-carrying cross-linker then reacts with cysteines on the surface of urease molecules. The probability of each amine being activated depends on its accessibility due to its surrounding native structure. To avoid urease dimer and polymers forming in the second reaction step, ideally only one amine per antibody would be activated by the NHS-ester. However, since multiple primary amines are present in each antibody, it is statistically inevitable that some V21H1 antibodies will be activated by more than one cross-linker molecule. The optimal activation condition was selected, which minimizes the percentage of antibodies that are activated by more than one cross-linker while maximizing the total amount of activated antibody. To assess the activation distribution, the SM(PEG)$_2$ activated V21H1 was reacted with excess cysteine and evaluated by intact mass spectrometric analysis. The mass spectrum is shown in FIG. 9. Approximately 50% of the V21H1 was activated by SM(PEG)$_2$ and of the activated antibody, approximately 30% was activated by two cross-linkers. Thus, only 35% of the V21H1 antibody is optimally activated for cross-linking with urease.

In order to determine which lysines of V21H1 were targeted by SM(PEG)$_2$, V21H1-SM(PEG)$_2$-Cys was subjected to tryptic digestion followed by LC-MS$^E$ analysis. Trypsin cleaves peptide backbone bonds at the C-terminal side of arginine and lysine residues (unless proline is immediately C-terminal to K or R). If a lysine is activated by SM(PEG)$_2$, the polarity and side-chain structure of the lysine is altered and spatially blocked. Thus, this tryptic site is no longer accessible to the protease. For example, if K$_{66}$ of V21H1 is activated by SM(PEG)$_2$, it is linked to -SM(PEG)$_2$-Cys and is no longer be available for tryptic digestion; therefore, a peak with a molecular mass of 2862.3018 (2431.1656+431.1362) Da should be observed, which represents the —SM(PEG)$_2$-Cys linked lysine-in-middle peptide, (ELVAAISWSDDSTYYANSVK66GR)-SM(PEG)$_2$-Cys (SEQ ID NO: 94). In the LC-MS$^E$ peptide mapping analysis, all possible activation sites can be identified by searching all the lysine carrying peptides and the N-terminal peptide with the —SM(PEG)$_2$-Cys (431.1362 Da) as a variable modifier. The detected tryptic peptides along with conjugation sites are listed in Table 2.

TABLE 2

List of identified peptides and activation sites of V21H1-(PEG)$_2$-Cys. The following sets of tryptic peptides are related groups of peptides used to calculate % of activation for each activation site (Tryptic Peptides T001 through T001-002; T004 through T005; T006 through T007; and T009 through T012).

| Tryptic Peptide # | Activation Site | Calculated Mass (Da) | MS/MS b/y Possible | MS/MS b/y Found | Intensity | Mass match error ppm | % of activation |
|---|---|---|---|---|---|---|---|
| T001 | | 1985.0364 | 38 | 37 | 28847130 | −2.4 | |
| T001* | M$_1$-SM(PEG)$_2$-Cys | 2416.1726 | 38 | 32 | 5688300 | 0.2 | 15.7 |
| T001-002 | | 2730.3904 | 54 | 28 | 1681792 | 0.8 | |
| T002 | | 763.3647 | 14 | 9 | 14953790 | 0.9 | |
| T002-003 | | 2066.9456 | 36 | 2 | 16053 | 2.8 | |
| T003 | | 1321.5913 | 20 | 18 | 87904800 | −2.4 | |
| T003-004 | | 180.8562 | 30 | nd | nd | nd | |
| T004 | | 499.2754 | 8 | 7 | 238539 | 0.4 | |
| T004-005 | | 784.4191 | 12 | 9 | 1334242 | 1.1 | |
| T004-005* | K$_{44}$-SM(PEG)$_2$-Cys | 1215.5553 | 12 | 6 | 369637 | 0.9 | 18.4 |
| T005 | | 303.1543 | 2 | 0 | 61996 | −3 | |
| T005-006 | | 2503.1868 | 42 | 28 | 5351105 | −1.2 | |
| T006 | | 2218.043 | 38 | 33 | 20205530 | −0.2 | |
| T006-007 | | 2431.1655 | 42 | 10 | 203405 | −3 | 12.4 |
| T006-007* | K$_{66}$-SM(PEG)$_2$Cys | 2862.3018 | 42 | 29 | 2900557 | −0.1 | |
| T007 | | 231.1331 | 2 | 1 | 147694 | −2.2 | |
| T007-008 | | 835.4664 | 12 | 9 | 1990138 | −2.8 | |
| T008 | | 622.3439 | 8 | 6 | 19702980 | 0 | |
| T008-009 | | 1050.5458 | 16 | 11 | 747025 | 0.1 | |
| T009 | | 446.2125 | 6 | 5 | 269841 | −1.3 | |
| T009-010 | | 3129.49 | 54 | nd | nd | nd | |
| T009-010* | K$_{77}$-SMP(EG)$_2$-Cys | 3560.6262 | 54 | 31 | 4111249 | 1.9 | 3.6 |
| T010 | | 2701.2881 | 46 | 36 | 108301696 | −2.7 | |
| T010 | | 2701.2881 | 46 | 36 | 108301696 | −2.7 | |
| T010* | K$_{88}$-SM(PEG)$_2$-Cys | 3132.4241 | 46 | 23 | 1836133 | −0.8 | 1.7 |
| T010-011 | | 6145.7744 | 108 | nd | nd | nd | |
| T010-011 | K$_{101}$-SM(PEG)$_2$-Cys | 6576.9103 | 60 | nd | nd | nd | |
| T011 | | 3462.4971 | 60 | 7 | 105092 | 1.9 | |
| T011-012 | | 3590.592 | 62 | 43 | 48704060 | 0.1 | |
| T011-012* | K$_{131}$-SM(PEG)$_2$-Cys | 4021.7283 | 62 | 12 | 258662 | −1.7 | 0.5 |
| 1012 | | 146.1055 | 0 | nd | nd | nd | |
| T012 | K$_{132}$-SM(PEG)$_2$-Cys | 577.2418 | 0 | nd | nd | nd | | nd = not detected

All tryptic peptides were detected with mass match errors of less than 5 ppm and the amino acid sequence recovery was 100%. Assuming that ESI sensitivity is not affected by the linkage of the modifier, an activation percentage was assessed by comparing the intensity of the cross-linker modified peptide with the sum intensity of all the related peptides. Under the activation conditions used, lysine residue $K_{66}$ in CDR2 was substantially (~25% of the entire activated V21H1 antibody) activated by the cross-linker; however, $K_{101}$ in CDR3 was not modified during cross-linker activation. Surprisingly, the two C-terminal lysine residues that were intentionally added for conjugation chemistry purposes were not modified by the cross-linker.

Production and Purification of V21H4

The antibody V21H4 was designed to improve upon the issues identified during production, purification and cross-linker activation of V21H1. The amino acid sequence of the V21H4 antibody is shown in SEQ ID NO:6. As for V21H11, a number of amino acid residues were added to the V21 antibody C-terminus ($G_{123}$-$C_{136}$) and the pI of the antibody was adjusted from 8.75 to 5.43. With V21H1, the presence of SM(PEG)$_2$ cross-linker activated $K_{66}$ in the antibody CDR2 region was a concern as this could impair antibody binding affinity. Thus, a cysteine residue ($C_{136}$) was added to V21H4 for sulfhydryl-to-sulfhydryl crosslinking using a different cross-linker, BM(PEG)$_2$:

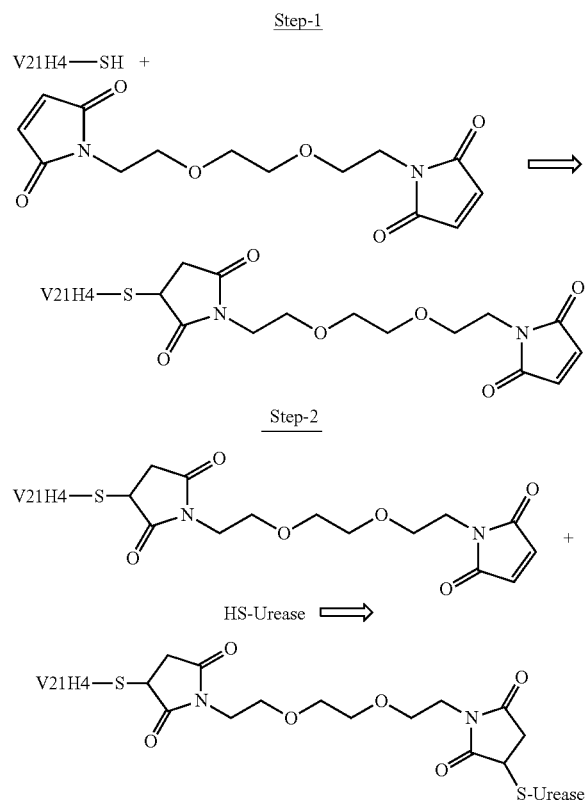

Step 1 is the activation of the antibody using BM(PEG)$_2$. Step 2 conjugates the activated antibody to urease.

The inclusion of a C-terminal cysteine also allowed the antibody to be expressed in bacterial inclusion bodies. As the two core cysteine residues of the V21 antibody form a disulfide bond and are unavailable for chemical conjugation, the additional C-terminal cysteine residue provides a unique activation site for targeted conjugation.

Figure 10:
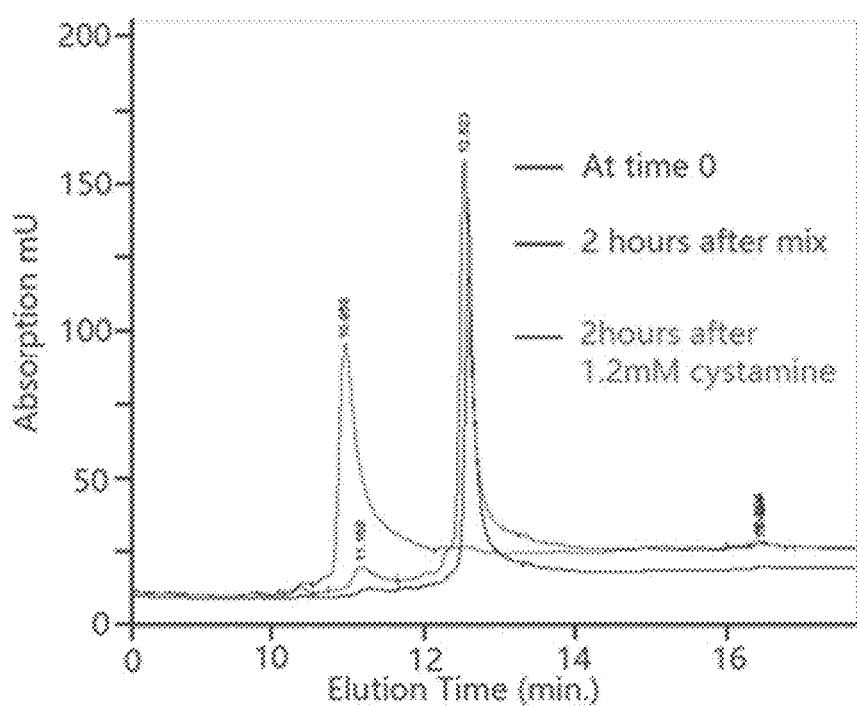
FIG. 10 shows RP-HPLC chromatograms of V21H4 (SEQ ID NO:6) samples at different refolding time points. Blue line: sample at refolding time 0, immediately after the SP pooled fraction was mixed with refolding buffer. Red line: refolding time point 2 hours after mixing. Green line: refolding sample 4 hours after time 0 and 2 hours after addition of 1.2 mM cystamine. Unfolded antibody elutes at 12.513 min and folded antibody elutes at 10.958 min.

V21H4 was expressed at high levels in inclusion bodies. After cell lysis, antibody was separated from bacterial matrix proteins by centrifugation. The denatured antibody was purified by cation exchange chromatography to remove nucleic acids and other proteins. The refolding of the V21H4 antibody was performed in an easily controllable manner and was monitored by HPLC (FIG. 10).

The refolding process was initiated by mixing the peak fraction of the cation exchange column with refolding buffer. While the folding process was very slow without cystamine, folding was complete in two hours at room temperature after cystamine was added to a final concentration of 1.2 mM. Anion exchange chromatography was used to isolate the properly folded protein, and yields of greater than 80% were generally observed. The typical yield of purified V21H4 is 20-40 mg/L culture, which is considerably higher than that of V21H1. In addition, the method used to produce and purify V21H4 is amenable to scale up and cGMP procedures.

Cross-Linker Activation of V21H4

Figure 11:
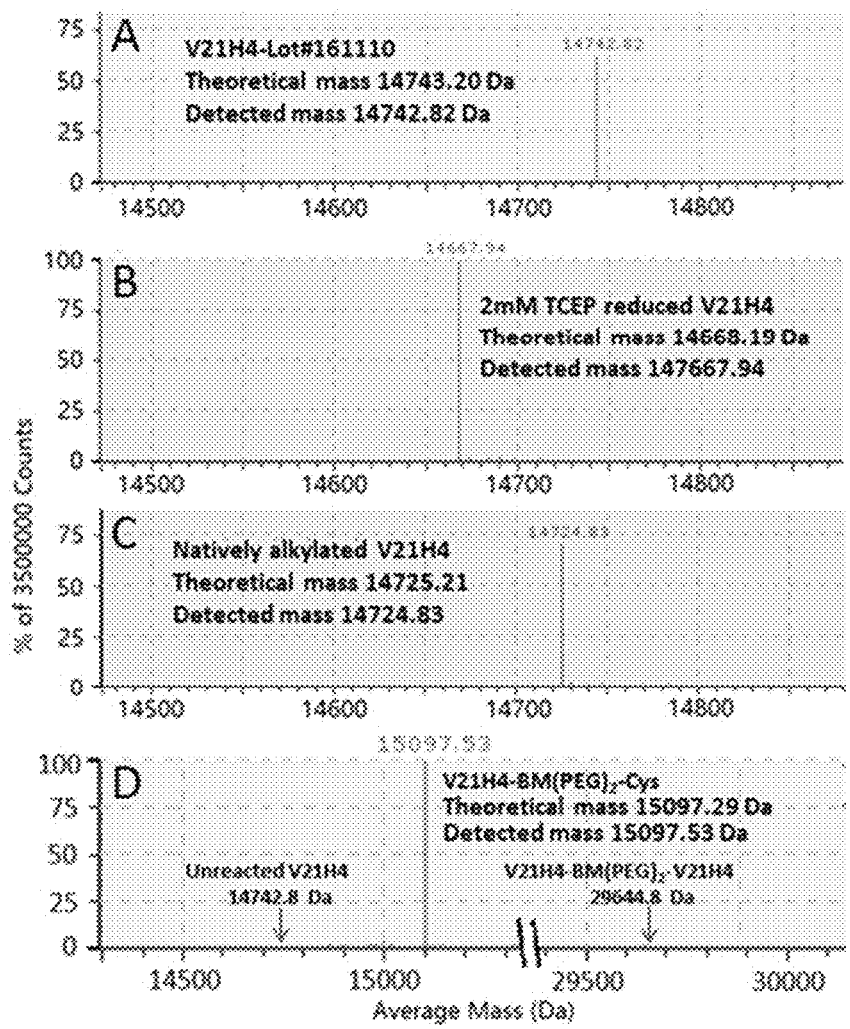
FIG. 11: (A-C) Screen snapshots of intact protein mass spectra of V21H4 (SEQ ID NO:6) samples from BiopharmaLynx. (A) Deconvoluted spectrum of V21H4 (SEQ ID NO:6) showing the attachment of a half-cystamine to the C-terminal cysteine by forming a disulfide bond during refolding. (B) The deconvoluted spectrum of V21H4 after reduction with 2 mM TCEP showing the detachment of the C-terminal half-cystamine. (C) The deconvoluted spectrum of the reduced V21H4 after alkylation with iodoacteamide showing the C-terminal cysteine is accessible to a sulfhydryl activation cross-linker. (D) Deconvoluted mass spectrum of V21H4 after activation by cross-linker and linkage to cysteine. V21H4 antibody activated by BM(PEG)$_2$ generates a single activated species.

The C-terminal cysteine of V21H4 is required for conjugation to urease. However, as cystamine was included in the V21H4 refolding buffer, the C-terminal cysteine was modified by forming a disulfide bond with a half cystamine (cysteamine-H). This was confirmed by LC-MS intact protein analysis (FIG. 11A). Thus, the half cystamine must be removed and the cysteine must subsequently be available for activation by cross-linker. In addition, this removal must occur using a controllable mild reduction under the native conditions to be used for conjugation purposes and it must not reduce the antibody's internal disulfide bond. As shown in FIG. 11B, after reducing V21H4 with 2 mM TCEP at pH 7.1 for one hour at room temperature, the detected antibody molecular mass was 14667.94 Da, suggesting that the protective half cystamine had been removed. In order to confirm that the de-protected cysteine residue was active to the cross-linking reagent, 10 mM iodoacetamide was added to the de-protected V21H4 antibody. After 30 minutes at room temperature at pH 7.5-8.0, the resulting detected molecular mass was increased to 14724.83 Da (FIG. 11C), suggesting a carboxymethyl group (57.05 Da) was alkylated to the cysteine residue. In summary, the C-terminal half cystamine can be removed and the resulting de-protected cysteine is available for chemical conjugation. The alkylated antibody was also digested with trypsin and evaluated by LC-MS$^E$ peptide mapping. The LC-MS$^E$ peptide map (data not shown) covered 100% of the amino acid sequence and the C-terminal cysteine was specifically and effectively alkylated, confirming the specificity of the de-protective reduction reaction and the suitability of the C-terminal cysteine in targeted sulfhydryl cross-linking chemistry.

The V21H4 antibody was activated by the cross-linker BM(PEG)$_2$. As BM(PEG)$_2$ is a homo-bifunctional cross-linker, it is possible that both maleimido groups of BM(PEG)$_2$ could react with and link two V21H4 molecules, leading to the generation of antibody dimers that cannot conjugate to urease. The frequency of antibody dimers generated depends upon the molar ratio of the reactants, the native hydrophobicity environment of the cysteine residue and the relative mobility of the molecules in the reaction solution. This reaction was performed with a 10:1 cross-linker to antibody molar ratio. In addition, the molecular weight of the cross-linker is 308.29 Da, which is approximately 50-fold less than the molecular weight of the antibody. To evaluate the activated V21H4 antibody, 100l of the activated antibody solution was reacted with excess cysteine and evaluated by intact mass spectrometric analysis (FIG. 11D). Under the experimental conditions used, more than 99% of the V21H4 was coupled to a single cross-linker, leaving the cross-linker's other maleimido group available for the subsequent reaction to urease.

In order to confirm that the C-terminal cysteine was the sole target of BM(PEG)$_2$, V21H4-BM(PEG)$_2$-Cys was subjected to tryptic digestion followed by LC-MS$^E$ analysis. If the C-terminal cysteine is activated by the cross-linker, a peak with a mass of 1266.3652 Da representing the cross-linker activated peptide GGGEEDDGC$_{136}$-BM(PEG)$_2$-Cys (SEQ ID NO:73) should be detected. If the core disulfide bond is reduced by TCEP before cross-linker activation, then two peaks—one representing the peptide LSC$_{23}$AASGR-BM(PEG)$_2$-Cys (SEQ ID NO:74) (1192.4852 Da) and the other representing SAVYLQMNSLKPEDTAVYYC$_{97}$AAHK-BM(PEG)$_2$-Cys (SEQ ID NO:75) (3130.4087 Da) should be identified. The detected tryptic peptides along with the cross-linker activation sites are listed in Table 3.

Conjugation of V21H1 and V21H4 to Urease and Initial Characterization

Jack bean urease is a homohexameric enzyme with each subunit approximately 91 kDa. Among the 15 unbound cysteine residues per subunit, five are on the surface of the native structure and are available for linking to single-domain antibodies through maleimido cross-linkers (Takishima et al., 1998). Different conjugation chemistries are widely used for protein conjugations. Copper-free click chemistry has been preferentially used in protein labeling and protein-drug conjugations (Thirumurugan et al., 2013) and was a potential option in our conjugations of antibodies to urease. However, either the NHS-ester or maleimido activation step would be needed before performing the click chemistry. Thus, traditional cross-linking chemistries are simpler and are suitable to this particular case.

Figure 12:
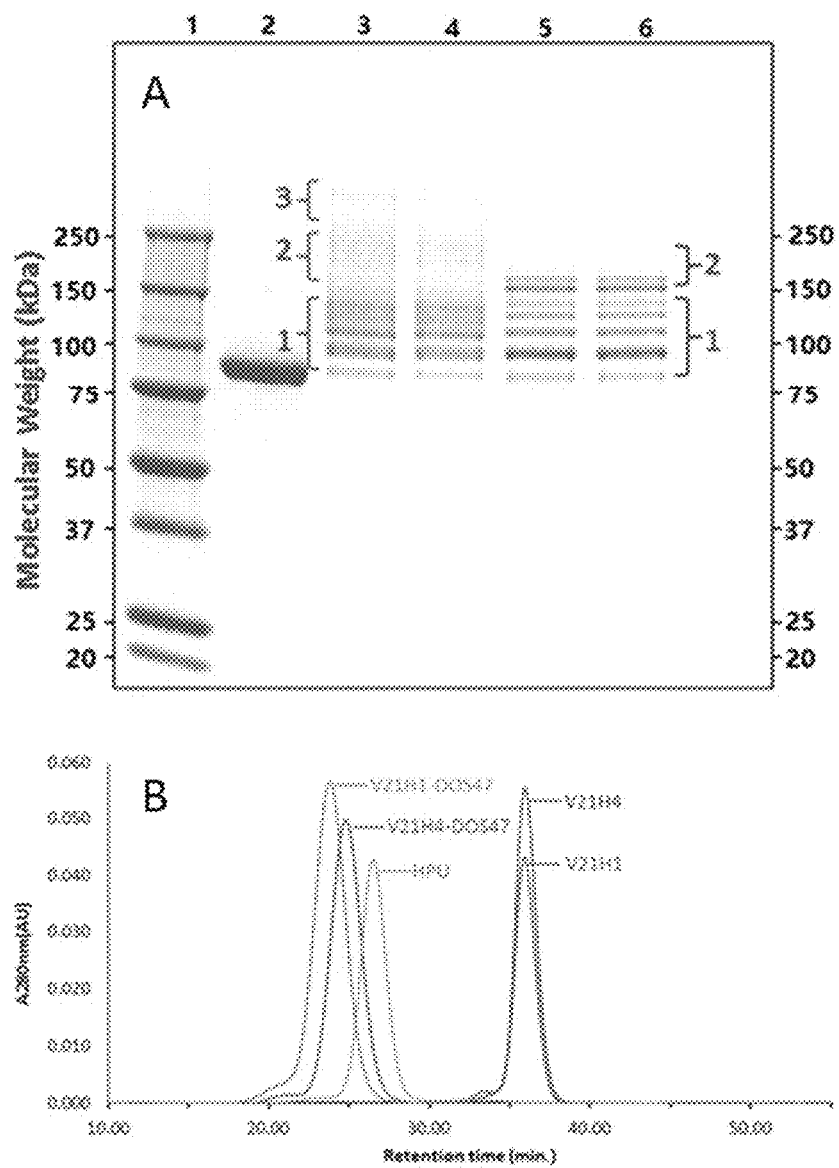
FIG. 12: (A) SDS-PAGE of V21H1-(SEQ ID NO:3) DOS47 and V21H4-(SEQ ID NO:6) DOS47. Bands labelled in red with 1, 2 or 3 are cluster numbers. Lane 1: molecular weight ladder. Lane 2: HPU. Lanes 3 and 4: V21H1-DOS47. Lanes 5 and 6: V21H4-DOS47. (B) Size exclusion chromatograms of V21H1, V21H4, high purity urease (HPU), V21H1-DOS47 and V21H4-DOS47.

After V21H1 and V21H4 were cross-linked, they were then conjugated to urease to generate V21H1-DOS47 and V21H4-DOS47, respectively. In both cases, sulfhydryl chemistry was used to conjugate the antibody-linker to urease. SDS-PAGE was performed to evaluate both conjugates (FIG. 12A).

TABLE 3

List of identified peptides and activation sites of V21H4-(PEG)$_2$-Cys. The following sets of tryptic peptides are related groups of peptides used to calculate % of activation for each activation site (Tryptic Peptides T002 through T002-003; T009-010 through T010-011; and T011-012 through T012).

| Tryptic Peptide # | Activation Site | Calculated Mass (Da) | MS/MS b/y Possible | MS/MS b/y Found | Intensity | Mass match error ppm | % of activation |
|---|---|---|---|---|---|---|---|
| T001 | | 1985.0364 | 38 | 34 | 25539260 | 1.2 | |
| T001-002 | | 2730.3904 | 54 | 17 | 55292 | 0.6 | |
| T002 | | 763.3647 | 14 | 8 | 7457241 | −0.7 | |
| T002* | C$_{23}$-BM(PEG)$_2$-Cys | 1192.4852 | 14 | 5 | 169047 | 2.1 | 2.2 |
| T002-003 | | 2066.9456 | 36 | nd | nd | nd | |
| T003 | | 1321.5913 | 20 | 18 | 29459300 | −0.5 | |
| T003-004 | | 1802.8562 | 30 | nd | nd | nd | |
| T004 | | 499.2754 | 8 | 5 | 254649 | −2.6 | |
| T004-005 | | 784.4191 | 12 | 8 | 1083205 | −2.7 | |
| T005 | | 303.1543 | 2 | 1 | 69756 | −4 | |
| T005-006 | | 2503.1868 | 42 | 27 | 4016949 | 3 | |
| T006 | | 2218.043 | 38 | 35 | 10074250 | −0.4 | |
| T006-007 | | 2431.1655 | 42 | 2 | 57264 | 4 | |
| T007 | | 231.1331 | 2 | 1 | 168759 | −4.3 | |
| T007-008 | | 835.4664 | 12 | 10 | 1210281 | −2.9 | |
| T008-009 | | 1050.5458 | 16 | 6 | 92188 | −2.4 | |
| T009 | | 446.2125 | 6 | 5 | 247926 | −0.9 | |
| T009-010 | | 3129.49 | 54 | nd | nd | nd | |
| T010 | | 2701.2881 | 46 | 35 | 62124531 | 1.3 | |
| T010* | C$_{97}$-BM(PEG)$_2$-Cys | 3130.4087 | 46 | 7 | 334626 | 3.3 | 0.5 |
| T010-011 | | 5613.6455 | 98 | nd | nd | nd | |
| T011 | | 2930.3682 | 50 | 37 | 18549570 | −1.4 | |
| T011-012 | | 3749.6023 | 68 | nd | nd | nd | |
| T012 | | 837.2446 | 16 | 8 | 150911 | −2.1 | |
| T012* | C$_{136}$-BM(PEG)$_2$-Cys | 1266.3652 | 16 | 10 | 1885506 | −0.2 | 92.6 | nd = not detected.

All tryptic peptides were detected with mass match errors of less than 5 ppm, and the amino acid sequence recovery was 100%. As expected, more than 90% of the C-terminal cysteine was activated by the cross-linker, and only trace amounts of cross-linker activated core cysteine residues (Cys$_{23}$ and Cys$_{97}$) were detected. This is a much more desirable scenario than that observed with V21H1 and SM(PEG)$_2$, in which multiple lysines are targeted, including the one in CDR2.

During conjugation, each of the six monomeric urease subunits could potentially be cross-linked with up to five antibody molecules; therefore, under denaturing SDS-PAGE conditions, both V21H1-DOS47 and V21H4-DOS47 would be expected to generate a pattern of six discrete bands ranging from ~90-180 kDa. However, it appears that a maximum of four antibodies are conjugated per urease, as only five discrete bands are observed (FIG. 12A, cluster 1).

This suggests that one of the five cysteine residues on the surface of urease has little or no ability to react with maleimide.

In addition to the expected five discrete bands, additional clusters of bands are observed for both V21H1-DOS47 and V21H4-DOS47. For V21H1-DOS47, two additional clusters are apparent. Cluster 2 (effective MW from ~200 to 250 Da) and cluster 3 (effective MW>300 Da) are likely urease dimers and polymers generated by V21H1 species carrying multiple SM(PEG)$_2$ cross-linkers. While these higher molecular weight species could be composed of multiple native urease molecules, the low levels (less than 5%) of dimer and polymer peaks observed by size exclusion chromatography (FIG. 12B) suggests that the majority of these species are composed of inter-subunit linkages of a single native urease molecule and not inter-molecular linkages.

For V21H4-DOS47, since only the C-terminal cysteine is activated by BM(PEG)$_2$, theoretically only one band cluster should be present. However, as demonstrated in Lanes 5 and 6, an additional cluster is observed in the V21H4-DOS47 lanes (MW≥than 150 kDa). The second cluster could be composed of non-covalent dimers that form as the conjugated subunits migrate in the gel. This was confirmed by SDS-PAGE capillary electrophoresis (not shown) in which no dimer clusters were observed. Therefore, V21H4-DOS47 does not contain cross-linked urease dimers or polymers.

SDS-PAGE was also used to determine the antibody:urease conjugation ratio for each native urease hexamer-antibody conjugate. Band intensities (FIG. 12A) in cluster 1 depend upon the relative abundance of urease monomers linked to different numbers of antibody molecules. Image-Lab software was used to generate histograms corresponding to band intensities and to integrate the peak areas of each histogram. The conjugation ratio (CR) for native urease hexamers was calculated as follows:

$$CR=6*(PK_1*0+PK_2*1+PK_3*2+PK_4*3+PK_5*4)/(PK_1+PK_2+PK_3+PK_4+PK_5)$$

Where $PK_i$ (i=1-5) is the peak area of the urease monomer linked with i−1 antibody molecules.

Although there is a variable number of antibodies conjugated to each urease monomer, one would predict less variability in the number of antibodies per urease hexamer, as the monomers randomly cluster to form hexamers. This was confirmed by SEC of native V21H4-DOS47 in which the conjugate is observed to migrate as a tight peak (FIG. 12B). The V21H4-DOS47 conjugation method reproducibly produced conjugates with 8.7-9.2 antibodies per urease (based on three batches).

The purities and the effective molecular weights of the antibodies, HP urease, and conjugates were assessed by size exclusion chromatography (SEC) under native conditions (FIG. 12B).

V21H1 and V21H4 antibodies elute at comparable times (35.9 minutes). Free HP urease elutes at 26 minutes. As antibody molecules are linked to urease molecules for both V21H1-DOS47 and V21H4-DOS47, making the conjugates larger than free urease, the conjugates elute earlier than free urease. However, it is interesting that V21H1-DOS47 elutes one minute before V21H4-DOS47 (22.80 vs 23.80 minutes). Both conjugates have nearly identical conjugation ratios (8.8 antibodies/urease for V21H1-DOS47 and 8.7 antibodies/urease for V21H4-DOS47). The V21H4 antibody has three more amino acids (159.20 Da) than V21H1; however, the theoretically larger V21H4-DOS47 conjugate appears smaller in effective molecular size in SEC than its counterpart V21H1-DOS47. This implies that V21H4-DOS47 is more compact than V21H1-DOS47 under native conditions.

The majority of each species is in the monomeric form, with small dimer peaks appearing in front of each monomeric peak. It is notable that the V21H1-DOS47 conjugation procedure requires a SEC step in order to achieve high purity (96%). The SEC step removes urease polymers that are generated by V21H1 antibodies activated by two cross-linkers. However, the SEC step is not necessary to produce V21H4-DOS47, as V21H4 antibodies are activated by one cross-linker only. For V21H4-DOS47, a purity of greater than 97% is typically achieved using only diafiltration to remove unbound V21H4 antibody. As SEC methods are not easily transferred to large-scale GMP processes, it would be technically more difficult and expensive to produce V21H1-DOS47 for clinical use.

Activity of V21H1-DOS47 and V21H4-DOS47

Figure 13:
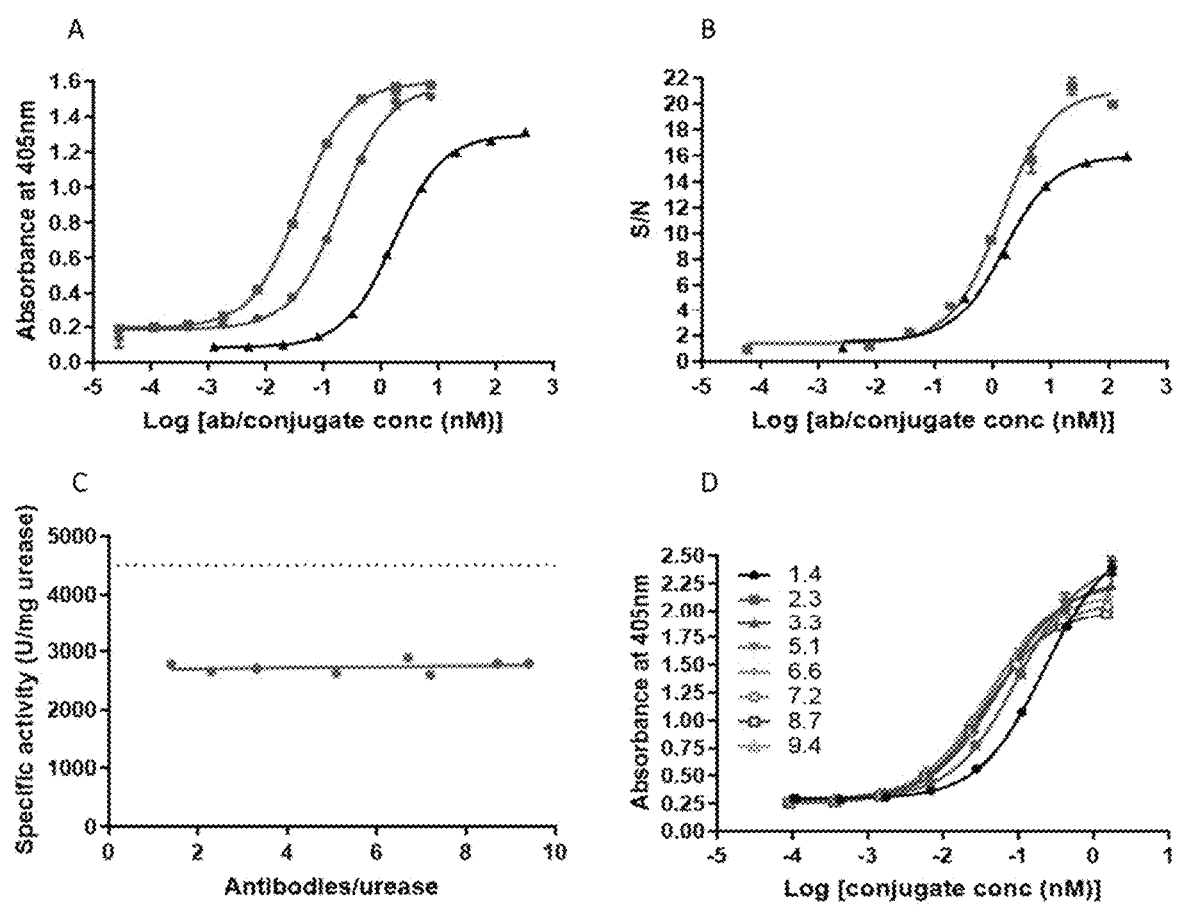
FIG. 13: (A) ELISA of biotin-V21H4 (SEQ ID NO:6) (black), V21H1-DOS47 (SEQ ID NO:3) (green) and V21H4-(SEQ ID NO:6) DOS47 (red) binding to recombinant VEGFR2/Fc. Results shown are representative of 2-5 experiments performed for each sample and are presented as the means and SE of samples tested in triplicate. (B) Binding of biotin-V21H4 (black) and V21H4-DOS47 (red) to VEGFR2 expressed by 293/KDR cells. Binding was quantified by flow cytometry. Results shown are representative of 2-3 experiments performed for each sample and are presented as the means and SE of samples tested in duplicate. (C) Urease enzyme activity of V21H4-DOS47 at different antibody/urease conjugation ratios. The dotted line represents unconjugated urease activity. (D) ELISA of V21H4-DOS47 with different antibody-urease conjugation ratios binding to recombinant VEGFR2/Fc. Results shown are representative of two experiments performed for each sample and are presented as the means and SE of samples tested in duplicate.

An ELISA assay was performed to evaluate the binding of V21H1-DOS47 (9.2 antibodies/urease), V21H4-DOS47 (8.8 antibodies/urease) and biotin-V21H4 to recombinant VEGFR2/Fc (FIG. 13A). V21H4-DOS47 (EC$_{50}$=44 pM) binds to VEGFR2/Fc with approximately five-fold higher affinity than does V21H1-DOS47 (EC$_{50}$=226 pM). As a substantial amount of V21H1 was conjugated to urease via the lysine present in CDR2, this is not surprising. V21H4-DOS47 also binds to VEGFR2/Fc with approximately 40-fold higher affinity than does V21H4 antibody alone (EC$_{50}$=1.8 nM). This is most likely due to the multivalent nature of the conjugate. As V21H4-DOS47 is the superior conjugate, subsequent characterization was performed for V21H4-DOS47 only.

The ability of V21H4 antibody and V21H4-DOS47 conjugate to bind to cells expressing VEGFR2 (293/KDR) was evaluated by flow cytometry (FIG. 13B). Biotin-V21H4 (EC$_{50}$=1.6 nM) binds to 293/KDR cells with a similar affinity as to recombinant VEGFR/Fc (EC$_{50}$=1.8 nM, FIG. 13A). This suggests that the VEGFR2 antibody epitope is equally accessible in recombinant VEGFR2/Fc in the ELISA assay and on the cell surface of 293/KDR cells. Interestingly, the binding of V21H4-DOS47 (EC$_{50}$=1.2 nM) to the 293/KDR cells is very similar to the binding of biotin-V21H4 antibody to these cells (EC$_{50}$=1.6 nM). Although there was an improved affinity observed for V21H4-DOS47 compared to V21H4 antibody in the ELISA assay with VEGFR2/Fc, this was not observed for cell binding. This suggests that the density of VEGFR2 expressed on the surface of 293/KDR cells is lower than in the wells of the ELISA plate.

Several factors contribute to determination of an ideal antibody/urease conjugation ratio. During the conjugation reaction, the urease molecule is altered by linkage to the V21 antibody; therefore, depending on the conjugation ratio, urease enzyme activity could be affected. On the other hand, the avidity of the antibody-urease complex increases as more antibodies are coupled to urease. To evaluate the effects of conjugation ratio on both the urease enzyme activity and on binding activity, V21H4-DOS47 conjugates with different conjugation ratios (1.4 to 9.4 V21H4 per urease) were produced by adjusting the V21H4/HPU molar ratios.

The activity of unmodified urease is approximately 4500 U/mg. When antibody is conjugated to urease, approximately 40% of the activity is lost (FIG. 13C). However, the urease enzyme activity is independent of the number of antibodies conjugated, as activity remains consistent at all conjugation ratios tested. An ELISA assay using recombinant VEGFR2/Fc was performed to evaluate the binding of conjugates with different numbers of antibodies per urease (FIG. 13D). When increasing from 1.4 to 2.3 antibodies per urease, the binding of the conjugate to VEGFR2/Fc improves, as indicated by a decrease in $EC_{50}$ values from 226 pM to 93 pM. Addition of one more antibody (3.3 antibodies/urease) further reduces the $EC_{50}$ to 58 pM However, addition of subsequent antibodies/urease has a limited benefit: with 9.4 antibodies per urease, the $EC_{50}$ is 31 pM. Thus, there is only a slight improvement in affinity when greater than 3.3 antibodies per urease are present. Thus, a conjugation ratio of 3.3 antibodies per urease is sufficient for optimal urease activity and conjugate binding.

Additional Characterization of V21H4-DOS47

Figure 14:
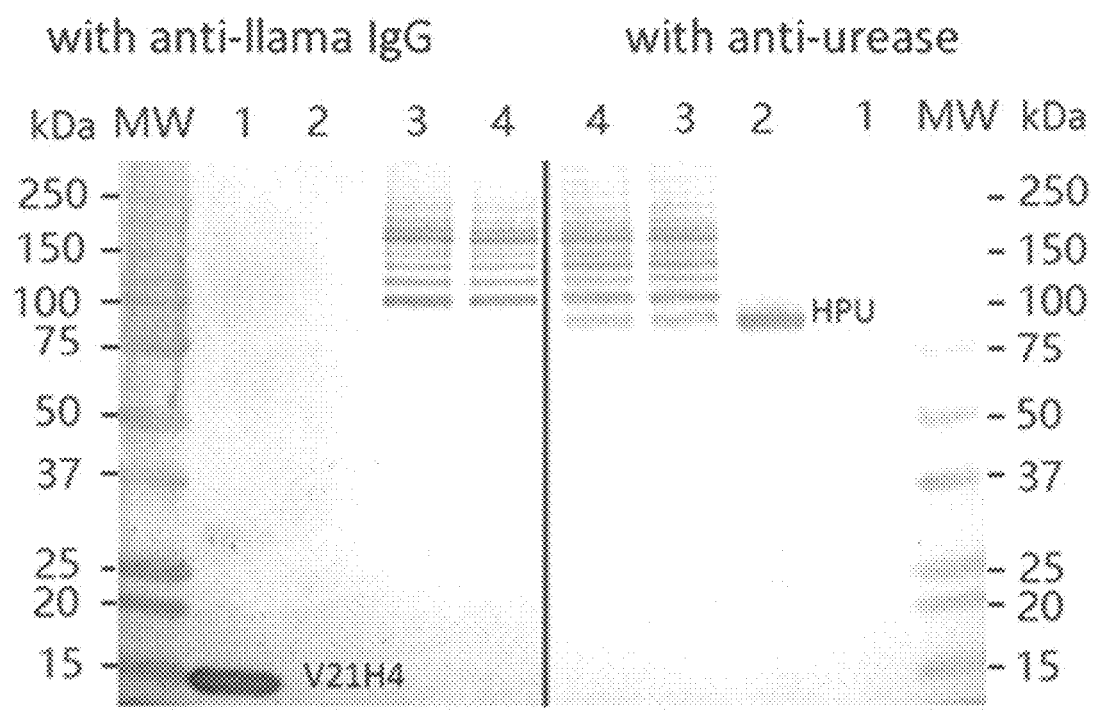
FIG. 14: Western blot of V21H4 (SEQ ID NO:6), HPU, and V21H4-(SEQ ID NO:6) DOS47. Blots were probed with (A) an anti-llama antibody or (B) an anti-urease antibody. Lane MW: molecular weight ladder. Lane 1: V21H4. Lane 2: HPU. Lanes 3 and 4: V21H4-DOS47.

Dual-panel Western blotting (FIG. 14) of V21H4-DOS47 was performed to confirm the banding pattern seen by SDS-PAGE. In Western blotting, the dimer and polymer clusters formed in-gel are more prominent than they appeared in SDS-PAGE (FIG. 12A). When probed with anti-urease antibody, the urease band is visualized at molecular weight ~85 kDa, and the bands of urease subunits bound to 1 to 4 antibodies match with the pattern seen by SDS-PAGE. When probed with an anti-llama antibody, the free urease subunit band is not observed and the antibody-urease conjugate bands are seen in the same pattern as when probed with an anti-urease antibody. The ability of V21H4-DOS47 to be visualized by both the anti-llama and anti-urease antibodies demonstrates the presence of both species in the conjugate.

Figure 15:
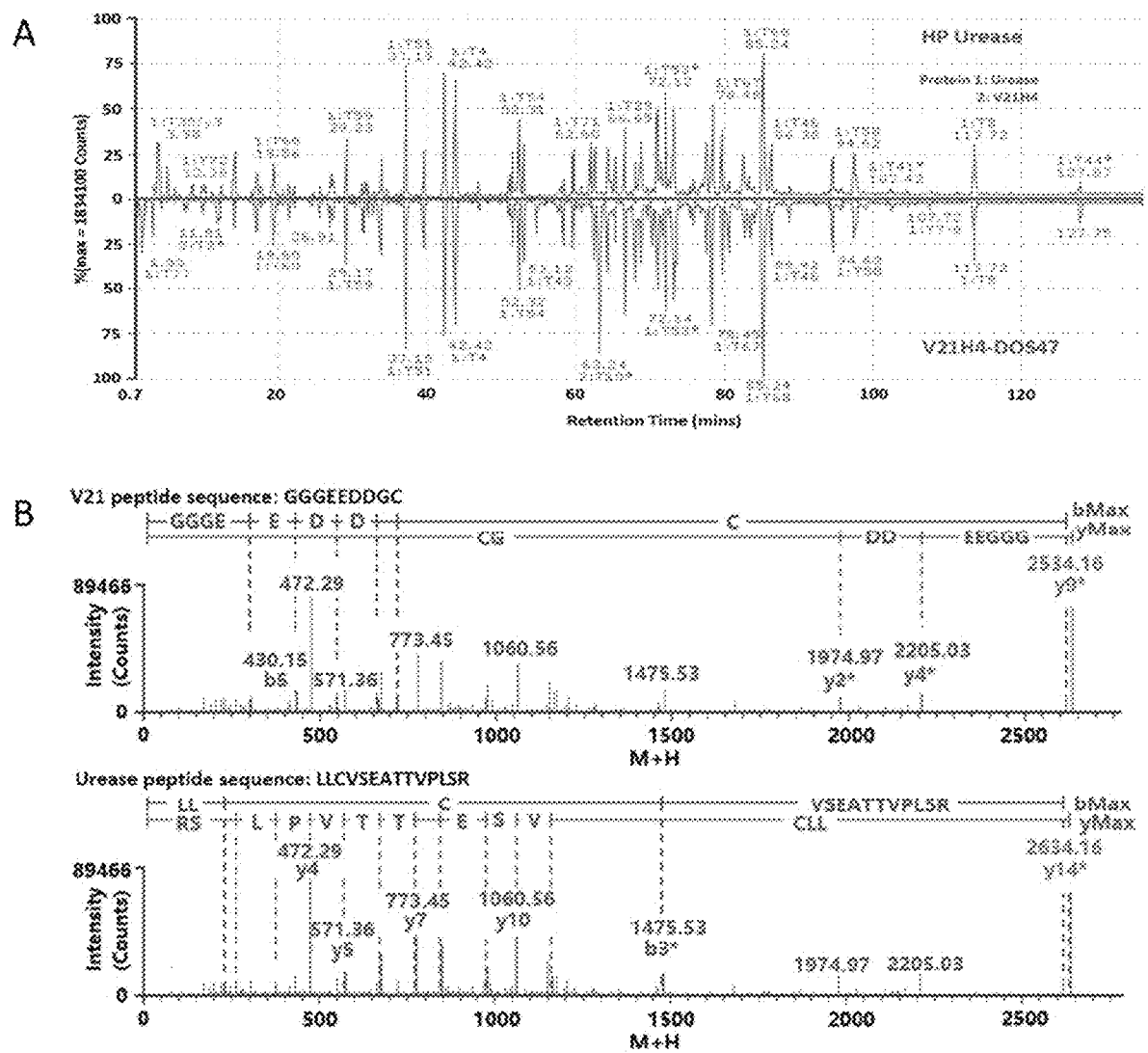
FIG. 15: (A) Screen snapshots of raw LC-MS (TIC) chromatograms of tryptic digests of HP urease (top) and V21H4-(SEQ ID NO:6) DOS47 (bottom) samples processed by BiopharmaLynx software. (B) Screen snapshots of b/y fragment profiles of conjugation site UC$_{824}$-VC$_{136}$ mapped as the V21H4 peptide GGGEEDDGC (SEQ ID NO: 91) (top) modified by UC$_{824}$-BM(PEG)$_2$ and as the urease peptide LLCVSEATTVPLS (SEQ ID NO: 92) (bottom) modified by VC$_{136}$-BM(PEG)$_2$.

ESI-LC-$MS^E$ peptide mapping analysis was employed to confirm the identities of V21H4 and urease and to identify the conjugation sites of V21H4-DOS47. The LC-MS (TIC) chromatograms of V21H4-DOS47 and HPU are shown in FIG. 15A.

The identified peptides covered 100% of V21H4 and urease protein sequences with mass match errors less than 4 ppm. All identified peptides with greater than three residues were confirmed by elevated energy MS/MS with at least half of the b/y ions identified. Since only the C-terminal GGGEEDDGC (SEQ ID NO:76) (837.2446 Da) of V21H4 is linked to different cysteine-carrying peptides of urease, the conjugation sites (denoted as $UC_x$-$VC_{136}$, where x is the amino acid in the urease protein sequence) are those urease peptides modified by GGGEEDDGC-BM(PEG)$_2$ (SEQ ID NO:72) (1145.3453 Da). To identify those covalent conjugation sites, ESI LC-$MS^E$ raw data of the tryptic digests from V21H4-DOS47 samples were processed by BiopharmaLynx and searched against the urease protein sequence with a variable modifier of 1145.3453 Da applied to all 15 urease cysteine residues. In order to assess the relative frequency of each conjugation site, the peptide intensities of the conjugated peptides $UC_x$-$VC_{136}$ were compared with the sum intensities of all the peptides related to $UC_x$ to generate the % of conjugation (Table 4).

TABLE 4

ESI LC-$MS^E$ peptide mapping analysis. Identification of urease cysteine residues modified by V21H4-(PEG)$_2$-Cys. na = not applicable.

| Conjugation sites searched from the urease side | | | | | | | |
|---|---|---|---|---|---|---|---|
| Urease peptide | Conjugation Site | Calculated Mass (Da) | MS/MS b/y Possible | MS/MS b/y Found | Intensity | Mass match error ppm | % of conjugation |
| 1:T010* | $UC_{59}$-$VC_{136}$ | 2784.2053 | 28 | 10 | 335045 | 2.6 | 2.6 |
| 1:T026* | $UC_{207}$-$VC_{136}$ | 1939.6624 | 12 | 0 | 10296 | 1.9 | 0.6 |
| 1:T063* | $UC_{663}$-$VC_{136}$ | 2316.7554 | 18 | 4 | 46812 | 2.9 | 4.2 |
| 1:1081* | $UC_{824}$-$VC_{136}$ | 2633.1372 | 26 | 13 | 495879 | 2.1 | 26.7 |

| Conjugation sites searched from the antibody side | | | | | | | |
|---|---|---|---|---|---|---|---|
| V21H4 C-term peptide | Conjugation Site | Calculated Mass (Da) | MS/MS b/y Possible | MS/MS b/y Found | Intensity | Mass match error ppm | % of conjugation |
| 2:T012 | na | 837.2446 | 16 | 2 | 10403 | −3.9 | 0.4 |
| 2:T012* | −$UC_{824}$ | 2633.1472 | 16 | 7 | 1609854 | 1.2 | 59.1 |
| 2:T012* | −$UC_{663}$ | 2784.2153 | 16 | 5 | 726682 | 1.6 | 26.7 |
| 2:T012* | −$UC_{59}$ | 2316.7654 | 16 | 4 | 343529 | −1.4 | 12.6 |
| 2:T012* | −$UC_{207}$ | 1939.6724 | 16 | 0 | 33038 | −3.6 | 1.2 |

Among the 15 cysteine residues of each urease subunit, only 4 were conjugated (consistent with bands observed by SDS-PAGE, FIG. 12A). The most accessible cysteine is $C_{824}$ (26.7%), followed in order by $C_{663}$ (4.2%), $C_{59}$ (2.6%), and $C_{207}$ (0.6%). No conjugation was detected to cysteine residue $C_{592}$, which is essential to urease enzyme activity. This is consistent with the observation that urease activity is comparable at all conjugation ratios (FIG. 13B).

Conjugation sites were also identified as V21H4 peptides modified by -$UC_x$ ($UC_x$+308.1008 Da). This was done by searching the V21H4 antibody protein sequence against -$UC_x$ as the variable modifier to the C-terminal cysteine of V21H4 (Table 3). Among the identified tryptic peptides, 0.4% of them were unmodified (T:012). This trace amount of peptide could be the portion of V21H4 activated by the cross-linker through $C_{23}$ and $C_{97}$ of the core sequence. Alternately, this peptide could be a trace amount of V21H4 attached to the C-terminal half cystamine that was not deprotected in the TCEP reduction step. These results are consistent with those observed with urease peptides modified by -$VC_{136}$. Most of the V21H4 C-terminal cysteine was conjugated to urease via $C_{824}$ (59%), with less conjugation at $C_{663}$ (27%), $C_{59}$ (12%), and $C_{207}$ (1.2%).

The identities of the conjugation sites were confirmed with b/y ion mapping of urease and V21H4 peptides. Among the 16 possible V21H4 b/y ions, only a few (4-7) were identified from the three major urease conjugation sites. This could be a result of the ESI ionization property of the GGGEEDDGC (SEQ ID NO:76) residues, which causes a lack of positive charge center in the ionization environment. However, the MS/MS b/y fragment profiles (FIG. 15B) can be assessed by looking at both V21H4 and urease proteins. As an example, the conjugated peptide $UC_{663}$-$VC_{133}$ whose sequence is (LLCVSEATTVPLSR)-linkage-(GG-GEEDDGC) (SEQ ID NOs: 77 and 76) and which has a peptide mass of 2633.1472 was identified with a mass match error of 2.1 ppm by searching it as LLCVSEATTVPLSR (SEQ ID NO:77), a urease peptide modified with (GG-GEEDDGC)-linkage (1145.3453 Da; SEQ ID NO: 76) from the V21H4 side as the modifier. The same peptide was also identified with a mass match error of 2.1 ppm by searching it as GGGEEDDGC (SEQ ID NO: 76), a V21H4 C-terminal peptide modified with (LLCVSEATTVPLSR)-linkage (1795.9026 Da; SEQ ID NO: 77) from the urease side as the modifier. The $MS^E$ collision induced MS/MS spectrum of this conjugated peptide was mapped with 13 b/y fragment ions from the urease side by searching it as a urease peptide modified with the modifier from the V21H4 side. The same spectrum was also mapped with 7 b/y ions from the V21H4 side by searching it as a V21H4 peptide with the modifier from the urease side.

Discussion

Antibody drug conjugates are emerging as a promising class of anti-cancer drugs. By delivering drugs directly to the target site, non-specific side effects are reduced. We have previously described the production and characterization of L-DOS47, an ADC composed of the enzyme urease and an anti-CEACAM6 antibody (Tian et al., 2015). L-DOS47 is currently in phase I/II trials for the treatment of non-small cell lung cancer. In this study, the conjugate V21H4-DOS47 was generated and characterized, which targets VEGFR2. Although L-DOS47 and V21H4-DOS47 were both generated by conjugating urease to a llama antibody, considerable research was required to produce a successful V21H4-DOS47 conjugate. For example, initial V21-DOS47 conjugates generated using the same linker as in L-DOS47, SIAB, was not as successful (SIAB is a short and rigid linker) as using $PEG_2$ class of linkers, which are relatively long and flexible, and now it is herein demonstrated that the binding activity of the conjugate was considerably improved.

In this study we developed procedures to conjugate and purify the V21-DOS47 immunoconjugate that are suitable for large scale cGMP production. Single domain camelid antibodies are ideal for use in generating antibody-enzyme conjugates. Their small molecular size allows them to be produced affordably in large amounts. Importantly, they were presently be modified by adding a short amino acid tag at the C-terminus. The tag serves several purposes, including modification of the antibody pI, promotion of targeted antibody expression, and addition of a specific reaction site. Since the pI of urease is in the 4.8 to 5.1 range, an antibody-urease conjugate generated with the unmodified core antibody would produce a conjugate with a pI of approximately 7. At this pI, the conjugate is unstable and forms precipitates during and after conjugation. The addition of a short C-terminal peptide tag adjusts the pI of the antibody from 8.75 to 5.43 leading to a conjugate with a pI between 4.8 and 5.5 which is stable during conjugation and purification. The C-terminal tag also improves the yield of antibody production by targeting expression to bacterial inclusion bodies. This allowed antibody purification using only ion exchange chromatography. As the V21 sequence contains two lysine residues in the CDR2 and CDR3 sequences respectively, lysine-to-sulfhydryl cross-linking chemistry could modify these lysine residues, compromising the binding affinity of the conjugate to its target antigen. For this reason, a C-terminal cysteine residue was included in the C-terminal tag of V21H4 for use in sulfhydryl-to-sulfhydryl cross-linking chemistry. $LC-MS^E$ characterization confirmed the modification of the CDR2 lysine residue by lysine-to-sulfhydryl cross-linking chemistry and an ELISA binding assay confirmed that the affinity of the V21H4-DOS47 produced by sulfhydryl-to-sulfhydryl cross-linking chemistry was approximately six-fold stronger than that of the V21H1-DOS47 conjugate produced by lysine-to-sulfhydryl cross-linking chemistry.

Although the addition of a C-terminal cysteine residue proved extremely useful in the conjugation of V21H4-DOS47, it will be understood that, when working with other llama antibodies, it may be necessary to evaluate the status of any core cysteine residues before determining if this strategy can be used. This is because the sulfhydryl-to-sulfhydryl chemistry uniquely targets the C-terminal cysteine only because the core cysteine residues are joined in a disulfide bond, and thus unavailable for modification.

Protein refolding can be a slow and unreproducible process. Typically, refolding is performed by dilution or dialysis, and the process can take several days. In addition, yield is generally low (Yamaguchi and Miyazaki, 2014). The introduction of a DTT/cystamine redox couple led to a short and reproducible refolding process that generated high yields of active V21H4 antibody, which is useful for large scale production.

One benefit of conjugating antibodies to urease is the apparent increased affinity of the conjugate compared to antibody alone. By clustering multiple antibodies per urease, avidity increases as the relative off-rate of the complex is slower than for free antibody. However, the improvement in antibody avidity must be balanced by the potential detrimental effects of adding antibody to urease, including impairment of urease activity and increased immunogenicity of the conjugate. In addition, high conjugation ratios increase production costs and complexity. Each antibody-urease conjugate may have a different ideal conjugation ratio, as the availability of the target antigen differs and the orientation and activity of the antibody presented on the urease surface changes with different conjugation chemistries. In this study, we observed little improvement in antigen binding at conjugation ratios greater than 3.3. This is in contrast with L-DOS47, in which binding increased until eight antibodies were conjugated per urease. The use of a more flexible linker to generate V21H4-DOS47 compared to L-DOS47 may partially explain this difference, as the antibodies may be more accessible to target antigen. However, the difference between the two conjugates is most likely due to the fact that AFAIKL2, the antibody component of L-DOS47, has a much lower affinity for its target antigen than does V21 for VEGFR2 (data not shown). Thus, antibody multimerization has a more pronounced effect for AFAIKL2 than for V21.

REFERENCES

Arbabi Ghahroudi, et al. (1997). *FEBS Lett.* 414, 521-526.
Cortez-Retamozo, et al. (2002). *Int. J. Cancer.* 98, 456-462.
Das, M., Wakelee, H. (2014). *Transl. Lung Cancer Res.* 3, 397-399.
De Genst, et al. (2006). *Dev. Comp. Immwwol.* 30, 187-198.
Dumoulin, et al. (2002). *Protein Sci.* 11, 500-515.

Faivre et al. (2007). *Nat. Rev. Drug Discov.* 6, 734-745.
Frenken, et al. (2000). *J. Biotechnol.* 78, 11-21.
Guo, et al. (2010). *Biochim. Biophys. Acta.* 1806, 108-121.
Hanahan, D. and Folkman, J. (1996). *Cell.* 86, 353-364.
Harmsen, M. M., De Haard, H. J. (2007). *Appl. Microbiol. Biotechnol.* 77, 13-22.
Itakura, et al. (2000). *Int. J. Cancer.* 85, 27-34.
Lauwereys, et al. (1998). *EMBO J.* 17, 3512-3520.
Maass, et al. (2007). *J. Immunol. Methods.* 324, 13-25.
Muyldermans, et al. (2001) *Trends Biochem. Sci.* 26, 230-235.
Olsson, et al. (2006). *Nat. Rev. Mol. Cell. Biol.* 7, 359-371.
Ribatti, D. (2011). *Int. J. Dev. Biol.* 55, 383-388.
Risau, W. (1997). *Nature.* 386, 671-674.
Takishima, et al. (1988). *Eur. J. Biochem.* 175, 15-165.
Tanno, et al. (2004). *Lung Cancer.* 46, 11-19.
Thirumurugan, et al. (2013). *Chem. Rev.* 113, 4905-4979.
Tian, et al. (2015). *Bioconjugate Chem.* 26, 1144-1155.
van der Linden, et al. (1999). *Biochin. Biophys. Acta.* 1431, 37-46.
Wilhelm, et al. (2006). *Nat. Rev. Drug Discov.* 5, 835-844.
Wong, et al. (2005). *J. Exp. Ther. Oncol.* 5, 93-99.
Yamaguchi, H., Miyazaki, M. (2014). *Biomolecules.* 4, 235-251.

Example 10

A CAR-T vector was constructed to express the V21 extracellular domain. This vector was then tested for activity against tumor cells that express VEGFR-2. Cytotoxicity was measured using a LDH-release assay and T-cell activity was evaluated by measuring IL-2 and IFN-γ cytokine levels secreted into the surrounding tissue culture media.

Protocol 1. Construction of CAR Vector

Figure 23:
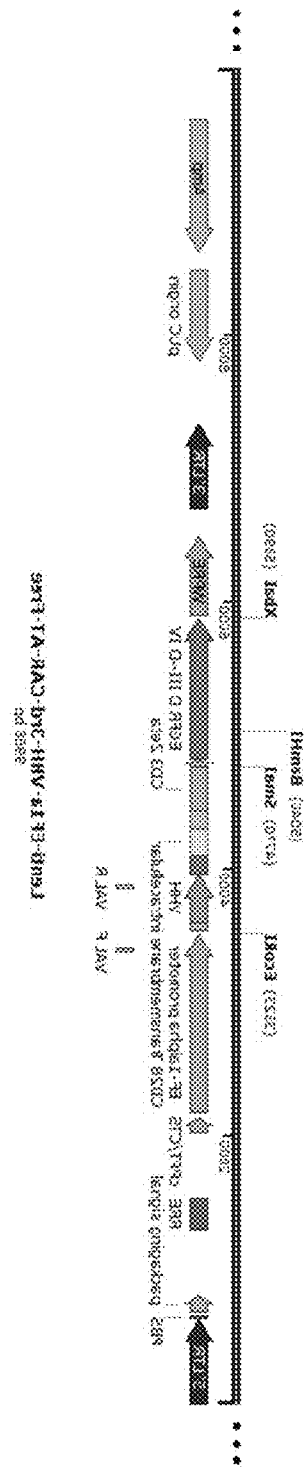
FIG. 23 shows the structure of a full length chimneric antigen receptor synthesized and subcloned into a Lentivirus vector.

The full length chimeric antigen receptor was synthesized and subcloned into Lentivirus vector. The insert was confirmed by Sanger sequencing. The structure of chimeric antigen receptor is shown in FIG. 23.

Protocol 2. Preparation of Lentivirus 1. 15 cm culture dishes were prepared and inoculated with $5 \times 10^6$ cells per culture dish; 25 mL complete culture medium (DMEM$_{high\ glucose}$, 10% FBS, penicillin-streptomycin) was added, and placed the dish into a 37° C., 5% $CO_2$ incubator overnight.
2. Defrosted the 100 μM PEI and lentivirus packaging system (Lenti-EF1a-VHH-3rd-CAR, pGP, pVSVG) at room temperature and thoroughly mixed by pipetting up and down; adding 2 mL PBS into one well of a 6-well-plate, and add 10 μg Lenti-EF1a-VHH-3rd-CAR, 4 μg pGP, 2 μg pVSVG, respectively; then, adding 18 μL 100 μM PEI and mix well before standing at room temperature for 10 min to form DNA/PEI complex.
3. Added the DNA/PEI complex into 15 cm culture dish dropwise and waggled the dish back and forth to mix well; placed the culture dish at 37° C. 5% $CO_2$ incubator for 6-8 hours; then refreshed the culture medium.
4. After 48 hours, harvest the culture medium containing lentiviral particles and filter the supernatant with 0.45 μm membrane; then centrifuge at 50000×g for 2 hours at 4° C.; after centrifugation, remove the supernatant in a biocabinet and add 500 μL PBS buffer to resuspend the pellet; aliquot the virus and preserve at −80° C.

Protocol 3. Lentivirus Titration

1. Recovery HT1080 cells from liquid nitrogen, adjust the cells until they are at logarithmic phase.
2. Plant HT1080 cells into a new 24-well-plate at 50000 cells/well. Add media to a final volume of 500 μL, then sit the plate in a 5% $CO_2$ 37° C. incubator overnight.
3. Add 10 μL of concentrated lentivirus to the wells, at the same time, polybrene is added to a concentration of 6 μg/mL.
4. Sit the plate in a 5% $CO_2$ 37° C. incubator for 96 hours.
5. Wash the cells with PBS. Extract genomic DNA with Genomic DNA Purification Kit (Lifetech, CAT #K0512). The concentration of extracted genomic DNA was determined by NanoDrop2000.
6. Dilute the PUCWPRE and PUCALB plasmids for 10 times. Prepare the standard sample for fluorescent quantitative PCR.
7. Prepare pre mixed solution for PCR reaction according to the table below.

| Reagents | Volume (for 20 μL reaction system) |
|---|---|
| 2xPCR Mix | 10 |
| Probe Mix (WPRE probe, ALB probe) | 0.4 |
| Primer mix (WPRE F&R, ALB F&R) | 0.4 |
| PCR grade water | 4.2 |

The information of primers of PCR

| Primers | 5'-3' | Fluorescent group |
|---|---|---|
| WPRE_forward | GGCACTGACAATTCCGTGGT (SEQ ID NO: 81) | N.A. |
| WPRE_revserse | AGGGACGTAGCAGAAGGACG (SEQ ID NO: 82) | N.A. |
| WPRE_probe | ACGTCCTTTCCATGGCTGCTCGC (SEQ ID NO: 83) | FAM-BHQ1 |
| Alb_forward | GCTGTCATCTCTTGTGGGCTGT (SEQ ID NO: 84) | N.A. |
| Alb_reverse | ACTCATGGGAGCTGCTGGTTC (SEQ ID NO: 85) | N.A. |
| Alb_probe | CCTGTCATGCCCACACAAATCTCTCC (SEQ ID NO: 86) | FAM-BHQ1 |

8. Add 5 μL/well of standard or genomic DNA samples to a 96-well-plate. 15 μL/well of pre mixed solution is added in the plate. Seal the plate with paperfilm and centrifuge for 1 min.
9. Conduct PCR reaction according to the following procedures.

| | Temp (° C.) | Time (sec) |
|---|---|---|
| Initial Hot Start/denaturation | 95 | 30 |
| Steps 1-2 are repeated through 40 cycles | | |
| Step 1 | 95 | 5 |
| Step 2 | 60 | 30 |

Protocol 4. Isolation of Primary T Cells
1. Mix Lymphoprep reagent by inverting end-to-end.
2. Add 15 mL Lymphoprep into a 50 mL tube.
3. Dilute the blood samples with PBS+2% FBS at 1:1.
4. Layer the diluted samples onto the Lymphoprep reagent carefully and slowly.

5. Centrifuge at 800×g for 20 min at 20° C.
6. After centrifugation, aspirate the white cell layer into a new tube, and wash the cells with PBS once.
7. Adjust the cell density to 1*10⁸ cells/mL (total volume within 2.5 mL) and place the cells into a 5 mL tube with round bottom.
8. Add 100 μl/mL cocktail into the tube and incubate at 15 min at room temperature.
9. Mix the beads and add 50 μl beads/mL to the sample, incubate at room temperature for 10 min.
10. Add complete medium until the volume reaches up to 2.5 mL, place the tube into magnet and sit for 5 min at room temperature.
11. After incubation, keep the tube in the magnet and pour the liquid.
12. Resuspend the cells with X-vivo 15 medium and add 10% human AB serum, 300 U/mL IL-2, 5 ng/mL IL-15 and 10 ng/mL IL-7.

Protocol 5. Transduction of T Cells with Lentivirus
1. Adjust the cell density to 1*10⁶ cells/mL, add the cytokines and antibodies to activate primary T cells for 48 hours. The cytokines and antibodies consists of 300 U/mL IL-2, 10 ng/mL IL-7, 5 ng/mL IL-15, 1 μg/mL Anti-CD3 (OKT3) and 2 μg/mL Anti-CD28.
2. Set MOI to 20 and calculate the volume of lentivirus for transduction.

Virus volume (mL)=(MOI*cell number)/virus titer

3. Quickly defrost lentivirus in a 37° C. water bath; add 6 μg/mL polybrene and virus, and mix thoroughly; seal the plate with paperfilm and centrifuge at 800×g for 1 hour.
4. After centrifugation, peel off the paperfilm and place the plate in a 37° C. 5% CO₂ incubator for 24 hours.
5. After centrifugation at 250×g for 10 min, remove the supernatant, then resuspend the cell pellet with fresh medium and continuously culture the cells for extra 3-6 days.

Protocol 6. CAR Expression Validation
1. Collect 2×10-6 CAR-T cells, divided the cells into two tubes with 1×10⁻⁶ CAR-T cells each. Resuspend the cells in 100 μL PBS.
2. Add 10 μL anti-EGFR antibody to one of the tube and incubate for 30 min at room temperature.
3. Centrifuge at 800×g for 5 min, remove the supernatant and wash the cells with 1 mL PBS for 3 times.
4. Add 10 μL APC-Anti-human IgG to both of the tubes and incubate at dark for 30 min at room temperature.
5. Centrifuge at 800×g for 5 min, remove the supernatant and wash the cells with 1 mL PBS for 3 times.
6. Resuspend the cells in 500 μL PBS and detect the CARs on the surface of T cells by FACS.

Protocol 7. Lysis of Target Tumor Cells with CAR-T
10. Adjust the target cells until they are at logarithmic phase. Generally, passage the cells twice before assay.
11. Lift the adherent cells with trypsin and adjust the cell density to 5×10⁵ cells/mL; inoculate 100 μL cell suspension into each well of a 96-well-plate. Add 100 μL sterilized water into all the unused wells to minimize the evaporation of the assay wells. Sit the plate in a 5% CO₂ 37° C. incubator overnight.
12. Harvest the CAR-T cells by centrifugation prepared in step 2 and resuspend the cell pellet with RPMI1640 medium without FBS; take out the 96-well-plate containing the target tumor cells and aspirate the culture completely and wash the cells with sterilized PBS; Add the CAR-T cells into each well according to the E/T ratio and supplement the final volume to 100 μL/well; meanwhile reserve four wells containing target cells without T cells as Maxi lysis and Mini lysis, respectively. Place the plate in a 5% CO₂ 37° C. incubator for 6 hours.
13. After cultivation, take out the plate and add cell lysis buffer into the Maxi lysis wells; centrifuge the plate at 1200×g for 5 min and transfer 50 μL supernatant into a new plate and add LDH detection reagent. Finally record the OD value with a Multiscan Spectrum.
14. The formulation of calculating the percentage of target cell lysis:

$$\text{Lysis \%} = \frac{(OD \text{ each well} - OD \text{ mini lysis})}{OD \text{ maxi lysis}} \times 100\%$$

Protocol 8. Detection of Cytokines by ELISA Assay
1. Adjust the target cells until they are at logarithmic phase. Generally passage the cells twice before assay.
2. Lift the adherent cells with trypsin and adjust the cell density to 5×10⁵ cells/mL; inoculate 100 μL cell suspension into each well of a 96-well-plate. Add 100 μL sterilized water into all the unused wells to minimize the evaporation of the assay wells. Sit the plate in a 5% CO₂ 37° C. incubator overnight.
3. Harvest the CAR-T cells by centrifugation and resuspend the cell pellet with 1640 medium without FBS; take out the 96-well-plate containing the target tumor cells and aspirate the culture completely and wash the cells with sterilized PBS; Add the CAR-T cells into each well according to the E/T ratio and supplement the final volume to 100 μL/well. Place the plate in a 5% CO₂ 37° C. incubator for 6 hours.
4. After cultivation, centrifuge the plate at 1200×g for 5 min at room temperature. Transfer 50 μL supernatant for detection of IL-2 and IFN-γ using ELISA assay kit.
5. Analyzing the data with GraphPad Prism 6.0.

Results of CAR and CAR-T
Protein sequence of VHH was that of SEQ ID NO:2.

Figure 16:
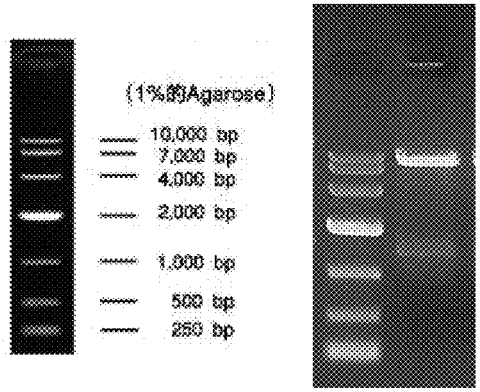
FIG. 16 is a restriction digestion map showing results of the endonuclease digestion validating the molecular weight of the inserted fragment (CAR cassette).

CAR Construction Validation
The recombinant lentiviral vector was digested with EcoRI-BamHI and a fragment around 1500 bp was generated (the estimated fragment was about 1518 bp). The results of endonuclease digestion showed that the molecule weight of inserted fragment was in accordance with the design (FIG. 16).

CAR Sequencing Validation
The recombinant vector was further sequenced and it was found that the sequence of constructed plasmid was in accordance with the design.

Lentivirus Titration

TABLE 1

| Sample | Ct value of the virus | | | |
|---|---|---|---|---|
| | WPRE | | ALB | |
| VHH-CAR | 24.3 | 24.71 | 28.69 | 28.76 |

Formula for Virus Titer Calculation:

$$\text{Lentivirus Titer } TU/\text{mL} = \frac{(\text{Copy } WPRE/\text{Copy } ALB * 2) * \text{Cell No.}}{\text{Volume of virus}}$$

TABLE 2

Lentivirus Titer

| Sample | Lentivirus Titer |
| --- | --- |
| VHH-CAR | 1.13*10$^8$ TU/mL |

Figure 17:
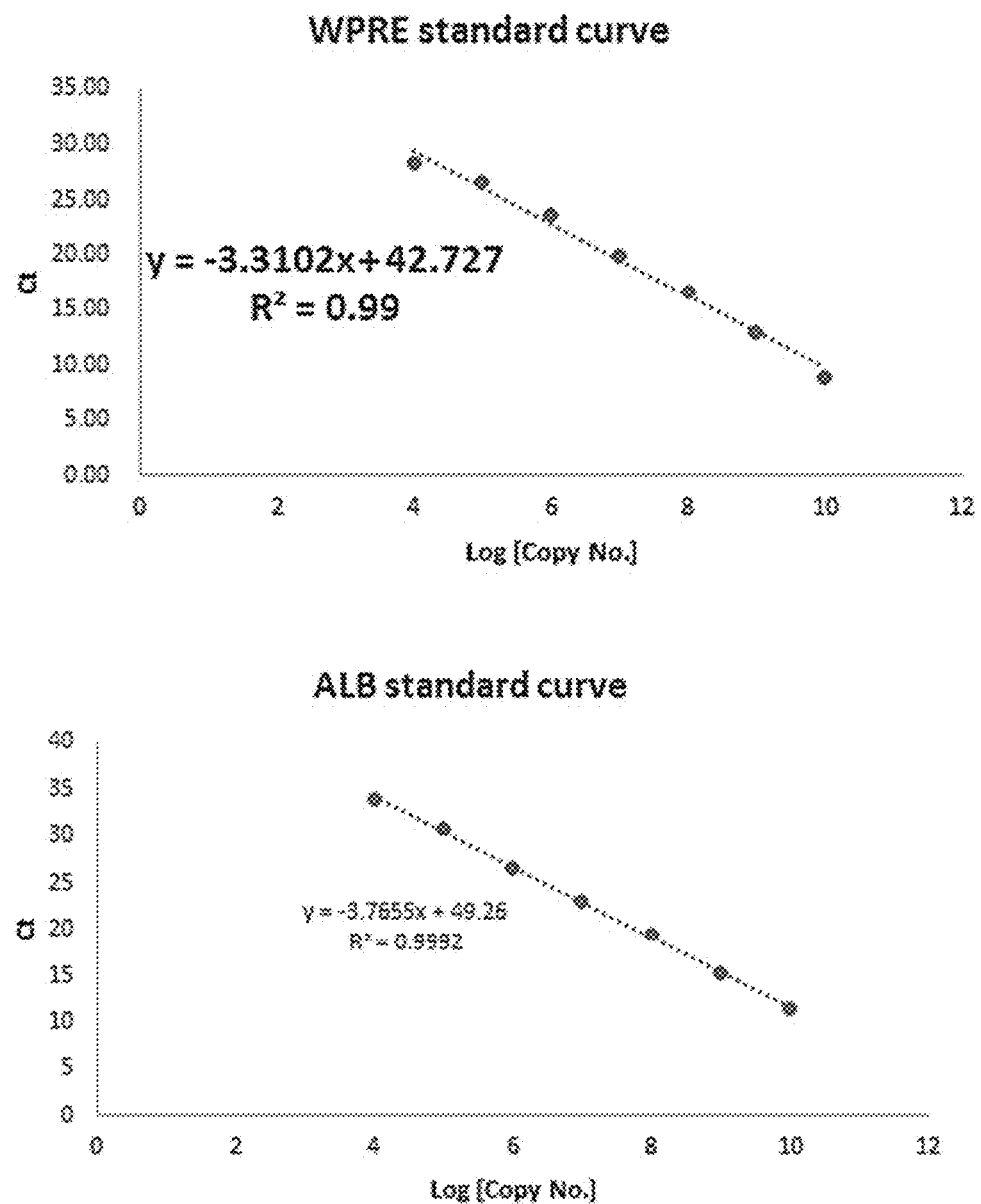
FIG. 17 shows the qPCR standard curve used to determine lentivirus titration.

The results of lentivirus titration showed that the lentiviral vector was prepared at a high titer. The qPCR standard curves used are shown in FIG. 17.

CAR Expression Validation

Figure 18:
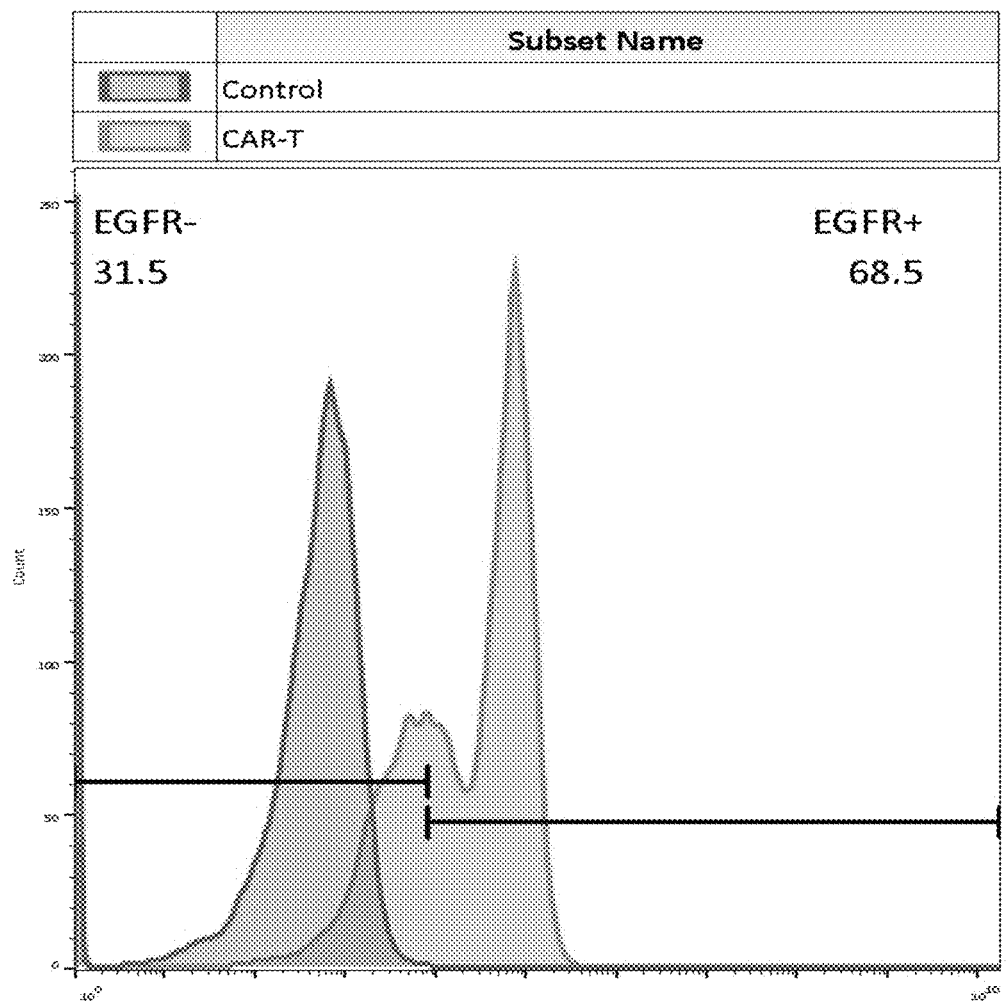
FIG. 18 shows the FACS detection of the CAR expression.

In the lentiviral vector, a truncated EGFR (Domain III&IV) is linked to VHH-CAR through the peptide and the expression of this EGFRt is driven by the same promoter. Therefore, detection the EGFRt reflects the information of the CAR expression. The FACS results showed that the lentiviral transduction was successful and the transduction efficiency (68.5%) was satisfactory (FIG. 18). Note: 40%-60% transduction efficiency is considered OK after two rounds of lentiviral infection.

Lysis of Target Tumor Cells by CAR-T

Figure 19:
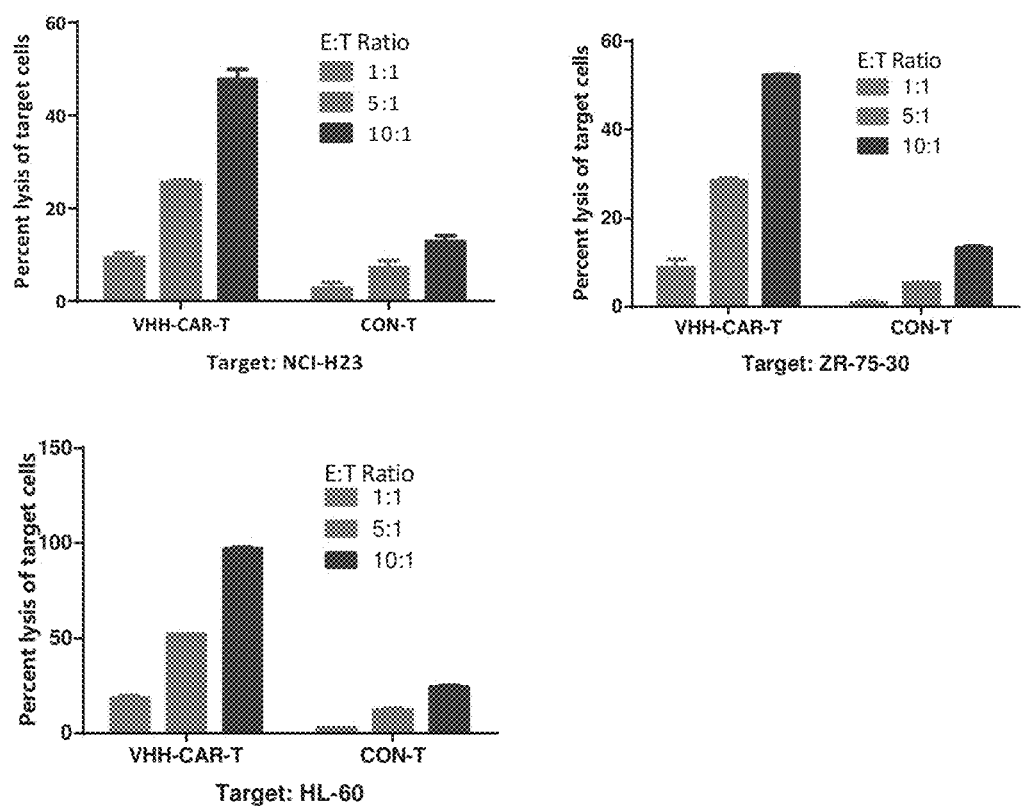
FIG. 19 are graphs showing LDH assays of lysis of target tumor cells with CAR-T of the invention showing the effectiveness of the anti-VEGFR-2 CAR-T in vitro in lung (NCI-H23), breast (ZR-75-30) and leukemia cells (HL-60). CON-T are non-transduced control T cells, CAR-T cells are VHH-CAR-T cells of the invention.

NCI-H23 cells, HL-60 cells, and ZR-75-30 cells were taken as target cells respectively, and were co-cultured with non-transduced control T cells and CAR-T cells at different E/T ratio as indicated in FIG. 19. After co-cultivation, the supernatant was harvested for detection of LDH by using LDH assay kit (FIG. 19). The lysis assay results showed that CAR-T cells targeting VEGFR-2 were able to kill the target cells in a "dose-dependent" way. The untransduced T cells also showed some cytolytic effect, which is due to the non-specific killing effects of activated T cells.

Detection of Cytokines by ELISA Assay

Figure 20:
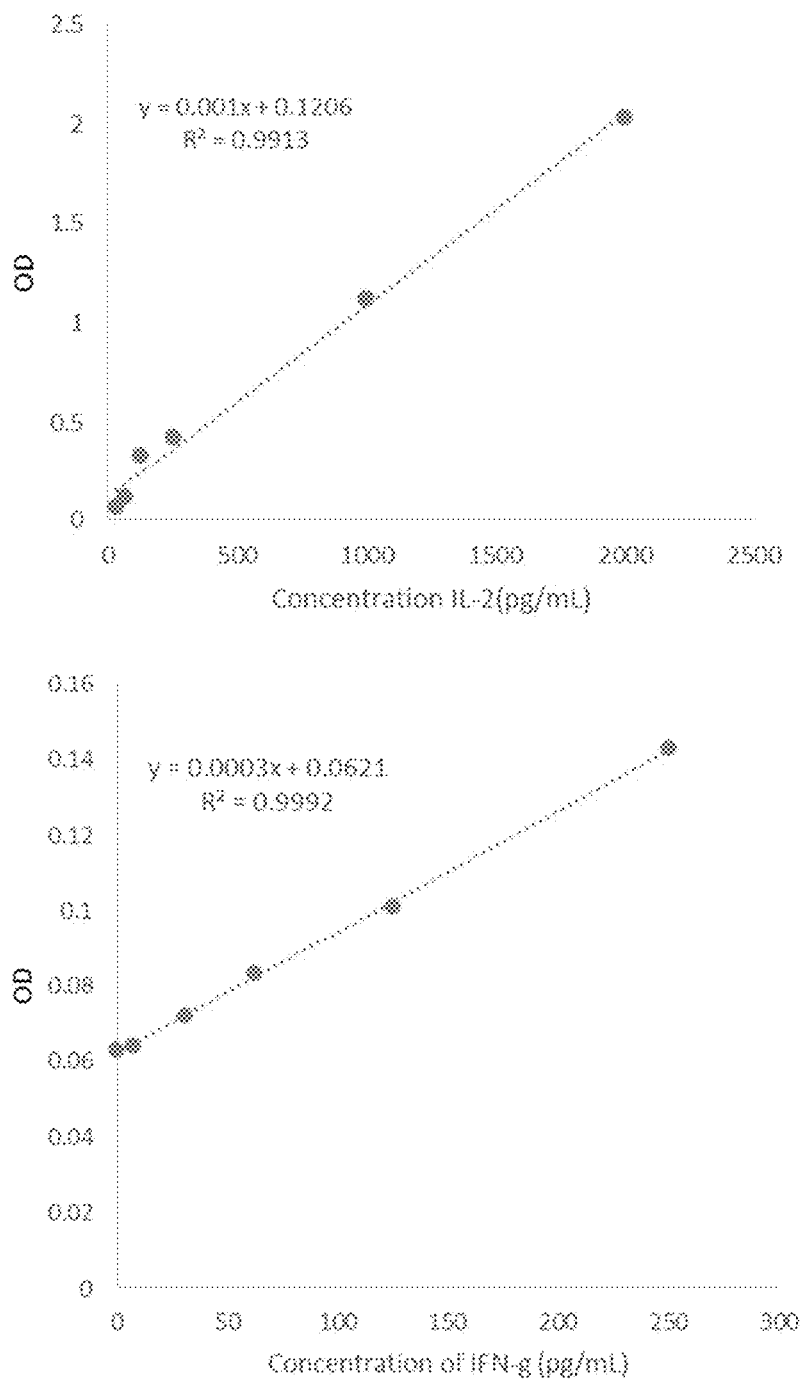
FIG. 20 are graphs showing standard curves for IL-2 and IFN-γ assays.
Figure 21:
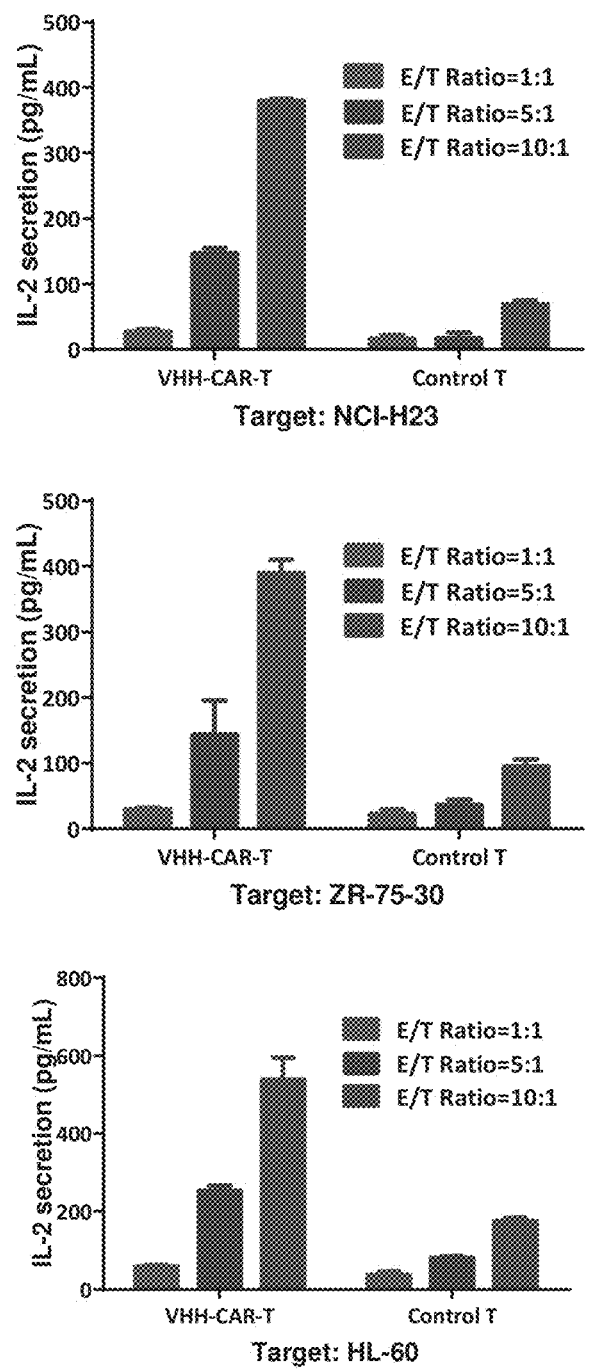
FIG. 21 are graphs showing ELISA detection of IL-2 produced by control T cells and CAR-T cells of the invention.
Figure 22:
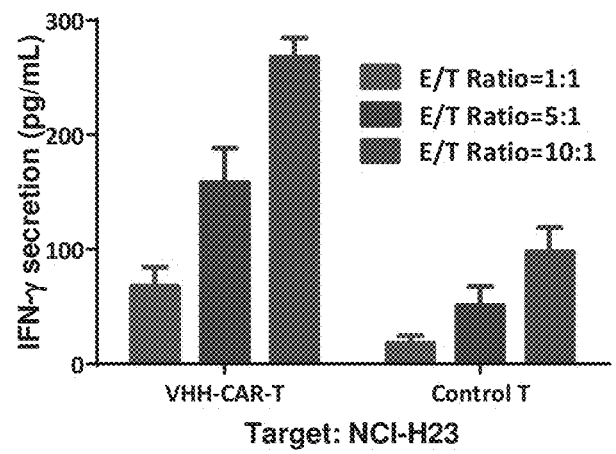
FIG. 22 are graphs showing ELISA detection of IFN-γ produced by control T cells and CAR-T cells of the invention.
Figure 22:
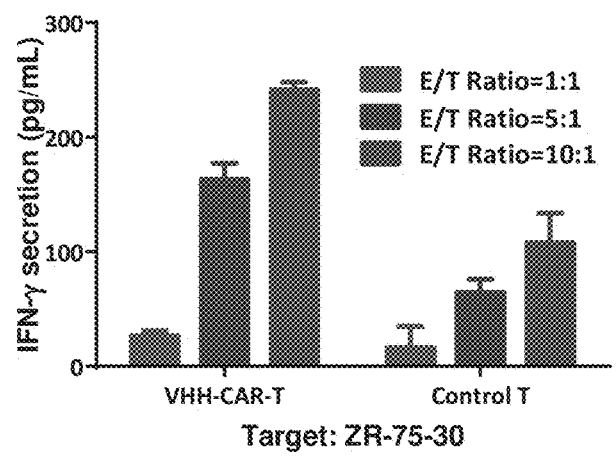
Figure 22:
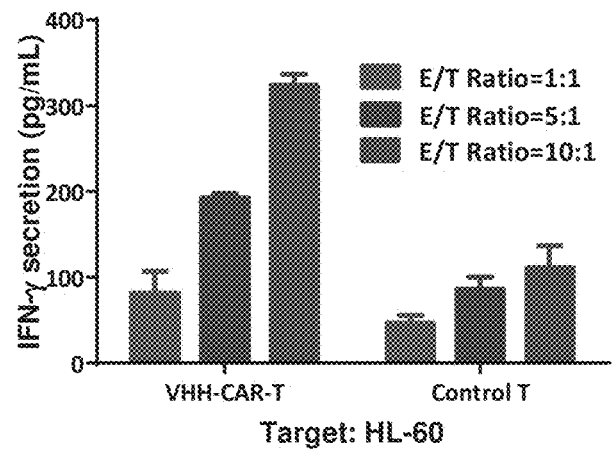

NCI-H23 cells, HL-60 cells, and ZR-75-30 cells were taken as target cells respectively, and were co-cultured with non-transduced control T cells and CAR-T cells at different E/T ratio as indicated in the figures below. The secretion level of IL-2 and IFN-γ was detected by ELISA assay (FIG. 21 and FIG. 22). Standard curves used are shown in FIG. 20. The cytokine release assay results showed that CAR-T cells secreted more cytokines than untransduced T cells after co-incubation with target cells, which indicate the recognition of target cells and activation of CAR-T cells.

The foregoing description and examples have been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A chimeric antigen receptor (CAR) that binds to VEGFR-2, an epitope or fragment thereof, or a variant thereof, wherein said CAR comprises a single domain antibody or a fragment thereof for binding to VEGFR-2, and wherein said CAR comprises the sequence of SEQ ID NO:78 or a sequence at least 90% identical thereto.

2. The CAR of claim 1, wherein said single domain antibody is a camelid single domain antibody or fragment thereof.

3. The CAR of claim 2, wherein said CAR binds to an epitope of VEGFR-2.

4. The CAR of claim 3, wherein said CAR binds to an epitope found in SEQ ID NO:1.

5. The CAR of claim 1, wherein said single domain antibody comprises a complementarity determining region (CDR) I; a CDR2; and/or a CDR3, wherein at least one of CDR1, CDR2 and CDR3 bind to VEGFR-2.

6. The CAR of claim 1, wherein the single domain antibody comprises at least one CDR having a sequence selected from the group consisting of SYAMG (,SEQ ID NO:87), AISWSDDSTYYANSVKG (SECID NO:88), HKSLQRPDEYTY (SECS ID NO:89) and a sequence at least 70% identical thereto which binds VEGFR2.

7. The CAR of claim 1, comprising a spacer molecule, a transmembrane region and one or more cell signaling domains selected from the group consisting of a human CD8-alpha protein, a human CD28 protein, a human CD3-zeta protein, a human FcRy protein, a CD27 protein, an OX40 protein, a human 4-IBB protein, modified versions of any of the foregoing, and any combination of the foregoing.

8. The CAR of claim 1, wherein the single domain antibody comprises a sequence selected from the group consisting of SEQ ID NO:2-30 or a fragment or variant thereof.

9. The CAR of claim 1, wherein the single domain antibody comprises a sequence selected from the group consisting of SEQ 11) NO:2-30 or a sequence at least 85%, at least 86%, at least 87%, at least 88%, at least 89%, at least 90%, at least 91%, at least 92%, at least 93%, at least 94% or at least 95% identical thereto, or a sequence substantially identical thereto.

10. The CAR of claim 9, wherein the sequence comprises a linker sequence selected from the group consisting of SEQ :ID NO:54-69.

11. The CAR of claim 10, wherein the linker sequence may further comprise a C-terminal cysteine.

12. The CAR of claim 11 wherein the linker sequence comprises GSEQKGGGEEDDGC (SEQ NO:66) or a variant thereof.

13. An immune cell comprising the CAR of claim 1.

14. The immune cell of claim 13, wherein said cell is a T cell or a cytokine induced killer (OK) cell.

15. The immune cell of claim 13, further comprising at least a second CAR.

16. The immune cell of claim 13, further comprising a transposon/transposase system that is optionally hyperactive.

17. The immune cell of claim 16, wherein the transposon/transposase system is a Sleeping Beauty transposon/transposase system.

18. The immune cell of claim 16, wherein the transposon/transposase system is the SB100X transposon/transposase system.

19. The immune cell of claim 13, further comprising a suicide gene.

20. The immune cell of claim 13, formulated into a composition comprising a pharmaceutically carrier, diluent, and/or excipient.

21. A nucleic acid molecule encoding the chimeric antigen receptor (CAR) of claim 1.

22. A method of treating cancer in a mammal, the method comprising administering the immune cell of claim 13 to the mammal in an amount effective to treat the cancer in the mammal.

23. A method to reduce angiogenesis in a tumor, the method comprising administering the immune cell of claim 13 to the mammal in an amount effective to reduce angiogenesis.

24. The CAR of claim 1 comprising a structure Signal peptide-VHH-CD8 hinge-CD28-4-1BB-CD3zeta-T2A-EGFR$_t$ encoded by the nucleic acid sequence of SEQ ID NO:79.

25. The CAR of claim 1 comprising a structure Signal peptide-VHH-CD8 hinge-CD28-4-1BB-CD3zeta-T2A-EGFRt that comprises an amino acid sequence of SEQ ID NO:78.

* * * * *

SEQUENCE LISTING

```
<160> NUMBER OF SEQ ID NOS: 94

<210> SEQ ID NO 1
<211> LENGTH: 1356
<212> TYPE: PRT
<213> ORGANISM: Homo sapiens

<400> SEQUENCE: 1

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175
```

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr

-continued

```
                595                 600                 605
Leu Trp Lys Leu Asn Ala Thr Met Phe Ser Asn Ser Thr Asn Asp Ile
610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Arg His Cys Val Val
                    645                 650                 655
Arg Gln Leu Thr Val Leu Glu Arg Val Ala Pro Thr Ile Thr Gly Asn
                    660                 665                 670
Leu Glu Asn Gln Thr Thr Ser Ile Gly Glu Ser Ile Glu Val Ser Cys
                    675                 680                 685
Thr Ala Ser Gly Asn Pro Pro Pro Gln Ile Met Trp Phe Lys Asp Asn
690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                    725                 730                 735
Cys Gln Ala Cys Ser Val Leu Gly Cys Ala Lys Val Glu Ala Phe Phe
                    740                 745                 750
Ile Ile Glu Gly Ala Gln Glu Lys Thr Asn Leu Glu Ile Ile Ile Leu
                    755                 760                 765
Val Gly Thr Ala Val Ile Ala Met Phe Phe Trp Leu Leu Leu Val Ile
770                 775                 780
Ile Leu Arg Thr Val Lys Arg Ala Asn Gly Gly Glu Leu Lys Thr Gly
785                 790                 795                 800
Tyr Leu Ser Ile Val Met Asp Pro Asp Glu Leu Pro Leu Asp Glu His
                    805                 810                 815
Cys Glu Arg Leu Pro Tyr Asp Ala Ser Lys Trp Glu Phe Pro Arg Asp
                    820                 825                 830
Arg Leu Lys Leu Gly Lys Pro Leu Gly Arg Gly Ala Phe Gly Gln Val
                    835                 840                 845
Ile Glu Ala Asp Ala Phe Gly Ile Asp Lys Thr Ala Thr Cys Arg Thr
850                 855                 860
Val Ala Val Lys Met Leu Lys Glu Gly Ala Thr His Ser Glu His Arg
865                 870                 875                 880
Ala Leu Met Ser Glu Leu Lys Ile Leu Ile His Ile Gly His His Leu
                    885                 890                 895
Asn Val Val Asn Leu Leu Gly Ala Cys Thr Lys Pro Gly Gly Pro Leu
                    900                 905                 910
Met Val Ile Val Glu Phe Cys Lys Phe Gly Asn Leu Ser Thr Tyr Leu
                    915                 920                 925
Arg Ser Lys Arg Asn Glu Phe Val Pro Tyr Lys Thr Lys Gly Ala Arg
                    930                 935                 940
Phe Arg Gln Gly Lys Asp Tyr Val Gly Ala Ile Pro Val Asp Leu Lys
945                 950                 955                 960
Arg Arg Leu Asp Ser Ile Thr Ser Ser Gln Ser Ser Ala Ser Ser Gly
                    965                 970                 975
Phe Val Glu Glu Lys Ser Leu Ser Asp Val Glu Glu Glu Glu Ala Pro
                    980                 985                 990
Glu Asp Leu Tyr Lys Asp Phe Leu Thr Leu Glu His Leu Ile Cys Tyr
                    995                 1000                1005
Ser Phe Gln Val Ala Lys Gly Met Glu Phe Leu Ala Ser Arg Lys
    1010                1015                1020
```

```
Cys Ile His Arg Asp Leu Ala  Ala Arg Asn Ile Leu  Leu Ser Glu
    1025            1030              1035

Lys Asn Val Val Lys Ile Cys  Asp Phe Gly Leu Ala  Arg Asp Ile
    1040            1045              1050

Tyr Lys Asp Pro Asp Tyr Val  Arg Lys Gly Asp Ala  Arg Leu Pro
    1055            1060              1065

Leu Lys Trp Met Ala Pro Glu  Thr Ile Phe Asp Arg  Val Tyr Thr
    1070            1075              1080

Ile Gln Ser Asp Val Trp Ser  Phe Gly Val Leu Leu  Trp Glu Ile
    1085            1090              1095

Phe Ser Leu Gly Ala Ser Pro  Tyr Pro Gly Val Lys  Ile Asp Glu
    1100            1105              1110

Glu Phe Cys Arg Arg Leu Lys  Glu Gly Thr Arg Met  Arg Ala Pro
    1115            1120              1125

Asp Tyr Thr Thr Pro Glu Met  Tyr Gln Thr Met Leu  Asp Cys Trp
    1130            1135              1140

His Gly Glu Pro Ser Gln Arg  Pro Thr Phe Ser Glu  Leu Val Glu
    1145            1150              1155

His Leu Gly Asn Leu Leu Gln  Ala Asn Ala Gln Gln  Asp Gly Lys
    1160            1165              1170

Asp Tyr Ile Val Leu Pro Ile  Ser Glu Thr Leu Ser  Met Glu Glu
    1175            1180              1185

Asp Ser Gly Leu Ser Leu Pro  Thr Ser Pro Val Ser  Cys Met Glu
    1190            1195              1200

Glu Glu Glu Val Cys Asp Pro  Lys Phe His Tyr Asp  Asn Thr Ala
    1205            1210              1215

Gly Ile Ser Gln Tyr Leu Gln  Asn Ser Lys Arg Lys  Ser Arg Pro
    1220            1225              1230

Val Ser Val Lys Thr Phe Glu  Asp Ile Pro Leu Glu  Glu Pro Glu
    1235            1240              1245

Val Lys Val Ile Pro Asp Asp  Asn Gln Thr Asp Ser  Gly Met Val
    1250            1255              1260

Leu Ala Ser Glu Glu Leu Lys  Thr Leu Glu Asp Arg  Thr Lys Leu
    1265            1270              1275

Ser Pro Ser Phe Gly Gly Met  Val Pro Ser Lys Ser  Arg Glu Ser
    1280            1285              1290

Val Ala Ser Glu Gly Ser Asn  Gln Thr Ser Gly Tyr  Gln Ser Gly
    1295            1300              1305

Tyr His Ser Asp Asp Thr Asp  Thr Thr Val Tyr Ser  Ser Glu Glu
    1310            1315              1320

Ala Glu Leu Leu Lys Leu Ile  Glu Ile Gly Val Gln  Thr Gly Ser
    1325            1330              1335

Thr Ala Gln Ile Leu Gln Pro  Asp Ser Gly Thr Thr  Leu Ser Ser
    1340            1345              1350

Pro Pro Val
    1355

<210> SEQ ID NO 2
<211> LENGTH: 122
<212> TYPE: PRT
<213> ORGANISM: Lama glama

<400> SEQUENCE: 2

Met Gln Val Gln Leu Val Glu Ser Gly Gly Gly Leu Val Gln Ala Gly
```

```
                1               5                  10                 15
Gly Ser Leu Arg Leu Ser Cys Ala Ala Ser Gly Arg Ala Phe Ser Ser
                20                  25                 30

Tyr Ala Met Gly Trp Phe Arg Gln Ala Pro Gly Lys Glu Arg Glu Leu
        35                  40                 45

Val Ala Ala Ile Ser Trp Ser Asp Asp Ser Thr Tyr Tyr Ala Asn Ser
    50                  55                 60

Val Lys Gly Arg Phe Thr Ile Ser Arg Asp Asn Ala Lys Ser Ala Val
65                  70                 75                 80

Tyr Leu Gln Met Asn Ser Leu Lys Pro Glu Asp Thr Ala Val Tyr Tyr
                85                  90                 95

Cys Ala Ala His Lys Ser Leu Gln Arg Pro Asp Glu Tyr Thr Tyr Trp
                100                 105                110

Gly Gln Gly Thr Gln Val Thr Val Ser Ser
            115                 120
```

<210> SEQ ID NO 3
<211> LENGTH: 133
<212> TYPE: PRT
<213> ORGANISM: Lama glama

<400> SEQUENCE: 3

```
Met Gln Val Gln Leu Val Glu Ser Gly Gly Gly Leu Val Gln Ala Gly
1               5                  10                 15

Gly Ser Leu Arg Leu Ser Cys Ala Ala Ser Gly Arg Ala Phe Ser Ser
                20                  25                 30

Tyr Ala Met Gly Trp Phe Arg Gln Ala Pro Gly Lys Glu Arg Glu Leu
        35                  40                 45

Val Ala Ala Ile Ser Trp Ser Asp Asp Ser Thr Tyr Tyr Ala Asn Ser
    50                  55                 60

Val Lys Gly Arg Phe Thr Ile Ser Arg Asp Asn Ala Lys Ser Ala Val
65                  70                 75                 80

Tyr Leu Gln Met Asn Ser Leu Lys Pro Glu Asp Thr Ala Val Tyr Tyr
                85                  90                 95

Cys Ala Ala His Lys Ser Leu Gln Arg Pro Asp Glu Tyr Thr Tyr Trp
                100                 105                110

Gly Gln Gly Thr Gln Val Thr Val Ser Ser Gly Ser Glu Glu Glu Asp
            115                 120                 125

Asp Asp Gly Lys Lys
        130
```

<210> SEQ ID NO 4
<211> LENGTH: 135
<212> TYPE: PRT
<213> ORGANISM: Lama glama

<400> SEQUENCE: 4

```
Met Gln Val Gln Leu Val Glu Ser Gly Gly Gly Leu Val Gln Ala Gly
1               5                  10                 15

Gly Ser Leu Arg Leu Ser Cys Ala Ala Ser Gly Arg Ala Phe Ser Ser
                20                  25                 30

Tyr Ala Met Gly Trp Phe Arg Gln Ala Pro Gly Lys Glu Arg Glu Leu
        35                  40                 45

Val Ala Ala Ile Ser Trp Ser Asp Asp Ser Thr Tyr Tyr Ala Asn Ser
    50                  55                 60

Val Lys Gly Arg Phe Thr Ile Ser Arg Asp Asn Ala Lys Ser Ala Val
```

```
                    65                  70                  75                  80
Tyr Leu Gln Met Asn Ser Leu Lys Pro Glu Asp Thr Ala Val Tyr Tyr
                        85                  90                  95

Cys Ala Ala His Lys Ser Leu Gln Arg Pro Asp Glu Tyr Thr Tyr Trp
                100                 105                 110

Gly Gln Gly Thr Gln Val Thr Val Ser Ser Gly Ser Glu Gln Lys Gly
            115                 120                 125

Gly Gly Glu Asp Asp Gly
        130             135

<210> SEQ ID NO 5
<211> LENGTH: 148
<212> TYPE: PRT
<213> ORGANISM: Lama glama

<400> SEQUENCE: 5

Met Lys Ala Ile Phe Val Leu Lys Gly Ser Leu Asp Arg Asp Pro Glu
1               5                   10                  15

Phe Asp Asp Glu Gly Gly Gly Gln Val Gln Leu Val Glu Ser Gly Gly
                20                  25                  30

Gly Leu Val Gln Ala Gly Gly Ser Leu Arg Leu Ser Cys Ala Ala Ser
            35                  40                  45

Gly Arg Ala Phe Ser Ser Tyr Ala Met Gly Trp Phe Arg Gln Ala Pro
        50                  55                  60

Gly Lys Glu Arg Glu Leu Val Ala Ala Ile Ser Trp Ser Asp Asp Ser
65                  70                  75                  80

Thr Tyr Tyr Ala Asn Ser Val Lys Gly Arg Phe Thr Ile Ser Arg Asp
                85                  90                  95

Asn Ala Lys Ser Ala Val Tyr Leu Gln Met Asn Ser Leu Lys Pro Glu
                100                 105                 110

Asp Thr Ala Val Tyr Tyr Cys Ala Ala His Lys Ser Leu Gln Arg Pro
            115                 120                 125

Asp Glu Tyr Thr Tyr Trp Gly Gln Gly Thr Gln Val Thr Val Ser Ser
        130                 135                 140

Gly Ser Glu Gln
145

<210> SEQ ID NO 6
<211> LENGTH: 136
<212> TYPE: PRT
<213> ORGANISM: Lama glama

<400> SEQUENCE: 6

Met Gln Val Gln Leu Val Glu Ser Gly Gly Gly Leu Val Gln Ala Gly
1               5                   10                  15

Gly Ser Leu Arg Leu Ser Cys Ala Ala Ser Gly Arg Ala Phe Ser Ser
                20                  25                  30

Tyr Ala Met Gly Trp Phe Arg Gln Ala Pro Gly Lys Glu Arg Glu Leu
            35                  40                  45

Val Ala Ala Ile Ser Trp Ser Asp Asp Ser Thr Tyr Tyr Ala Asn Ser
        50                  55                  60

Val Lys Gly Arg Phe Thr Ile Ser Arg Asp Asn Ala Lys Ser Ala Val
65                  70                  75                  80

Tyr Leu Gln Met Asn Ser Leu Lys Pro Glu Asp Thr Ala Val Tyr Tyr
                85                  90                  95

Cys Ala Ala His Lys Ser Leu Gln Arg Pro Asp Glu Tyr Thr Tyr Trp
```

```
            100                 105                 110
Gly Gln Gly Thr Gln Val Thr Val Ser Ser Gly Ser Glu Gln Lys Gly
            115                 120                 125

Gly Gly Glu Glu Asp Asp Gly Cys
        130                 135

<210> SEQ ID NO 7
<211> LENGTH: 141
<212> TYPE: PRT
<213> ORGANISM: Lama glama

<400> SEQUENCE: 7

Met Gln Val Gln Leu Val Glu Ser Gly Gly Gly Leu Val Gln Ala Gly
1               5                   10                  15

Gly Ser Leu Arg Leu Ser Cys Ala Ala Ser Gly Arg Ala Phe Ser Ser
            20                  25                  30

Tyr Ala Met Gly Trp Phe Arg Gln Ala Pro Gly Lys Glu Arg Glu Leu
        35                  40                  45

Val Ala Ala Ile Ser Trp Ser Asp Asp Ser Thr Tyr Tyr Ala Asn Ser
50                  55                  60

Val Lys Gly Arg Phe Thr Ile Ser Arg Asp Asn Ala Lys Ser Ala Val
65                  70                  75                  80

Tyr Leu Gln Met Asn Ser Leu Lys Pro Glu Asp Thr Ala Val Tyr Tyr
                85                  90                  95

Cys Ala Ala His Lys Ser Leu Gln Arg Pro Asp Glu Tyr Thr Tyr Trp
            100                 105                 110

Gly Gln Gly Thr Gln Val Thr Val Ser Ser Gly Ser Glu Gln Lys Leu
            115                 120                 125

Ile Ser Glu Glu Asp Leu Asn His His His His His
        130                 135                 140

<210> SEQ ID NO 8
<211> LENGTH: 124
<212> TYPE: PRT
<213> ORGANISM: Lama glama

<400> SEQUENCE: 8

Met Lys Lys Gln Val Gln Leu Val Glu Ser Gly Gly Gly Leu Val Gln
1               5                   10                  15

Ala Gly Gly Ser Leu Arg Leu Ser Cys Ala Ala Ser Gly Arg Ala Phe
            20                  25                  30

Ser Ser Tyr Ala Met Gly Trp Phe Arg Gln Ala Pro Gly Lys Glu Arg
        35                  40                  45

Glu Leu Val Ala Ala Ile Ser Trp Ser Asp Asp Ser Thr Tyr Tyr Ala
50                  55                  60

Asn Ser Val Lys Gly Arg Phe Thr Ile Ser Arg Asp Asn Ala Lys Ser
65                  70                  75                  80

Ala Val Tyr Leu Gln Met Asn Ser Leu Lys Pro Glu Asp Thr Ala Val
                85                  90                  95

Tyr Tyr Cys Ala Ala His Lys Ser Leu Gln Arg Pro Asp Glu Tyr Thr
            100                 105                 110

Tyr Trp Gly Gln Gly Thr Gln Val Thr Val Ser Ser
            115                 120

<210> SEQ ID NO 9
<211> LENGTH: 133
<212> TYPE: PRT
```

-continued

<213> ORGANISM: Lama glama

<400> SEQUENCE: 9

Met Lys Lys Gln Val Gln Leu Val Glu Ser Gly Gly Gly Leu Val Gln
1               5                   10                  15

Ala Gly Gly Ser Leu Arg Leu Ser Cys Ala Ala Ser Gly Arg Ala Phe
            20                  25                  30

Ser Ser Tyr Ala Met Gly Trp Phe Arg Gln Ala Pro Gly Lys Glu Arg
        35                  40                  45

Glu Leu Val Ala Ala Ile Ser Trp Ser Asp Asp Ser Thr Tyr Tyr Ala
    50                  55                  60

Asn Ser Val Lys Gly Arg Phe Thr Ile Ser Arg Asp Asn Ala Lys Ser
65                  70                  75                  80

Ala Val Tyr Leu Gln Met Asn Ser Leu Lys Pro Glu Asp Thr Ala Val
                85                  90                  95

Tyr Tyr Cys Ala Ala His Lys Ser Leu Gln Arg Pro Asp Glu Tyr Thr
            100                 105                 110

Tyr Trp Gly Gln Gly Thr Gln Val Thr Val Ser Ser Gly Ser Glu Glu
        115                 120                 125

Glu Asp Asp Gly
    130

<210> SEQ ID NO 10
<211> LENGTH: 144
<212> TYPE: PRT
<213> ORGANISM: Lama glama

<400> SEQUENCE: 10

Met Lys Ala Ile Phe Val Leu Lys Gly Ser Leu Asp Arg Asp Pro Glu
1               5                   10                  15

Phe Asp Asp Glu Gly Gly Gly Gln Val Gln Leu Val Glu Ser Gly Gly
            20                  25                  30

Gly Leu Val Gln Ala Gly Gly Ser Leu Arg Leu Ser Cys Ala Ala Ser
        35                  40                  45

Gly Arg Ala Phe Ser Ser Tyr Ala Met Gly Trp Phe Arg Gln Ala Pro
    50                  55                  60

Gly Lys Glu Arg Glu Leu Val Ala Ala Ile Ser Trp Ser Asp Asp Ser
65                  70                  75                  80

Thr Tyr Tyr Ala Asn Ser Val Lys Gly Arg Phe Thr Ile Ser Arg Asp
                85                  90                  95

Asn Ala Lys Ser Ala Val Tyr Leu Gln Met Asn Ser Leu Lys Pro Glu
            100                 105                 110

Asp Thr Ala Val Tyr Tyr Cys Ala Ala His Lys Ser Leu Gln Arg Pro
        115                 120                 125

Asp Glu Tyr Thr Tyr Trp Gly Gln Gly Thr Gln Val Thr Val Ser Ser
    130                 135                 140

<210> SEQ ID NO 11
<211> LENGTH: 126
<212> TYPE: PRT
<213> ORGANISM: Homo sapiens

<400> SEQUENCE: 11

Met Gln Val Gln Leu Val Glu Ser Gly Gly Gly Leu Ile Lys Pro Gly
1               5                   10                  15

Gly Ser Leu Arg Leu Ser Cys Ala Ala Ser Gly Phe Arg Phe Ser Ala
            20                  25                  30

-continued

Glu Ser Met Thr Trp Val Arg Gln Ala Pro Gly Lys Gly Leu Glu Trp
            35                  40                  45

Val Ser Ala Ile Ser Ser Gly Gly Ser Thr Tyr Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Val Tyr Tyr
                85                  90                  95

Cys Val Arg Ser Pro Lys Gly Cys Thr His Ala Ser Cys Ser Trp Asn
                100                 105                 110

Ser Gly Ser Trp Gly Gln Gly Thr Leu Val Thr Val Ser Ser
            115                 120                 125

<210> SEQ ID NO 12
<211> LENGTH: 136
<212> TYPE: PRT
<213> ORGANISM: Homo sapiens

<400> SEQUENCE: 12

Met Gln Val Gln Leu Val Glu Ser Gly Gly Gly Leu Ile Lys Pro Gly
 1               5                  10                  15

Gly Ser Leu Arg Leu Ser Cys Ala Ala Ser Gly Phe Arg Phe Ser Ala
                20                  25                  30

Glu Ser Met Thr Trp Val Arg Gln Ala Pro Gly Lys Gly Leu Glu Trp
            35                  40                  45

Val Ser Ala Ile Ser Ser Gly Gly Ser Thr Tyr Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Val Tyr Tyr
                85                  90                  95

Cys Val Arg Ser Pro Lys Gly Cys Thr His Ala Ser Cys Ser Trp Asn
                100                 105                 110

Ser Gly Ser Trp Gly Gln Gly Thr Leu Val Thr Val Ser Ser Gly Ser
            115                 120                 125

Glu Glu Asp Asp Asp Glu Glu Lys
    130                 135

<210> SEQ ID NO 13
<211> LENGTH: 144
<212> TYPE: PRT
<213> ORGANISM: Homo sapiens

<400> SEQUENCE: 13

Met Gln Val Gln Leu Val Glu Ser Gly Gly Gly Leu Ile Lys Pro Gly
 1               5                  10                  15

Gly Ser Leu Arg Leu Ser Cys Ala Ala Ser Gly Phe Arg Phe Ser Ala
                20                  25                  30

Glu Ser Met Thr Trp Val Arg Gln Ala Pro Gly Lys Gly Leu Glu Trp
            35                  40                  45

Val Ser Ala Ile Ser Ser Gly Gly Ser Thr Tyr Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Val Tyr Tyr
                85                  90                  95

Cys Val Arg Ser Pro Lys Gly Cys Thr His Ala Ser Cys Ser Trp Asn
            100                 105                 110

Ser Gly Ser Trp Gly Gln Gly Thr Leu Val Thr Val Ser Ser Gly Ser
            115                 120                 125

Glu Gln Lys Leu Ile Ser Glu Glu Asp Leu Asn His His His His
    130                 135                 140

<210> SEQ ID NO 14
<211> LENGTH: 149
<212> TYPE: PRT
<213> ORGANISM: Homo sapiens

<400> SEQUENCE: 14

Met Gln Val Gln Leu Val Glu Ser Gly Gly Gly Leu Ile Lys Pro Gly
1               5                   10                  15

Gly Ser Leu Arg Leu Ser Cys Ala Ala Ser Gly Phe Arg Phe Ser Ala
            20                  25                  30

Glu Ser Met Thr Trp Val Arg Gln Ala Pro Gly Lys Gly Leu Glu Trp
        35                  40                  45

Val Ser Ala Ile Ser Ser Gly Gly Ser Thr Tyr Tyr Ala Asp Ser
65              70                  75                  80

Val Lys Gly Arg Phe Thr Ile Ser Arg Asp Asn Ser Lys Asn Thr Val
65              70                  75                  80

Tyr Leu Gln Met Asn Ser Leu Arg Ala Glu Asp Thr Ala Val Tyr Tyr
            85                  90                  95

Cys Val Arg Ser Pro Lys Gly Cys Thr His Ala Ser Cys Ser Trp Asn
            100                 105                 110

Ser Gly Ser Trp Gly Gln Gly Thr Leu Val Thr Val Ser Ser Gly Ser
            115                 120                 125

Glu Gln Lys Leu Ile Ser Glu Glu Asp Leu Asn Gly Gly Glu Asp
    130                 135                 140

Asp Glu Glu Gly Cys
145

<210> SEQ ID NO 15
<211> LENGTH: 125
<212> TYPE: PRT
<213> ORGANISM: Homo sapiens

<400> SEQUENCE: 15

Gln Val Gln Leu Val Glu Ser Gly Gly Gly Leu Ile Lys Pro Gly Gly
1               5                   10                  15

Ser Leu Arg Leu Ser Cys Ala Ala Ser Gly Phe Arg Phe Ser Ala Glu
            20                  25                  30

Ser Met Thr Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65              70                  75                  80

Leu Gln Met Asn Ser Leu Arg Ala Glu Asp Thr Ala Val Tyr Tyr Cys
            85                  90                  95

Val Arg Ser Pro Lys Gly Cys Thr His Ala Ser Cys Ser Trp Asn Ser
            100                 105                 110

Gly Ser Trp Gly Gln Gly Thr Leu Val Thr Val Ser Ser
            115                 120                 125

<210> SEQ ID NO 16
<211> LENGTH: 143
<212> TYPE: PRT
<213> ORGANISM: Homo sapiens

<400> SEQUENCE: 16

```
Gln Val Gln Leu Val Glu Ser Gly Gly Gly Leu Ile Lys Pro Gly Gly
1               5                   10                  15

Ser Leu Arg Leu Ser Cys Ala Ala Ser Gly Phe Arg Phe Ser Ala Glu
            20                  25                  30

Ser Met Thr Trp Val Arg Gln Ala Pro Gly Lys Gly Leu Glu Trp Val
        35                  40                  45

Ser Ala Ile Ser Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Arg Ser Pro Lys Gly Cys Thr His Ala Ser Cys Ser Trp Asn Ser
            100                 105                 110

Gly Ser Trp Gly Gln Gly Thr Leu Val Thr Val Ser Ser Gly Ser Glu
        115                 120                 125

Gln Lys Leu Ile Ser Glu Glu Asp Leu Asn His His His His
    130                 135                 140
```

<210> SEQ ID NO 17
<211> LENGTH: 149
<212> TYPE: PRT
<213> ORGANISM: Homo sapiens

<400> SEQUENCE: 17

```
Met Lys Ala Ile Phe Val Leu Lys Gly Ser Leu Asp Arg Asp Pro Glu
1               5                   10                  15

Phe Asp Asp Glu Glu Gly Gly Gly Gln Val Gln Leu Val Glu Ser Gly
            20                  25                  30

Gly Gly Leu Ile Lys Pro Gly Gly Ser Leu Arg Leu Ser Cys Ala Ala
        35                  40                  45

Ser Gly Phe Arg Phe Ser Ala Glu Ser Met Thr Trp Val Arg Gln Ala
    50                  55                  60

Pro Gly Lys Gly Leu Glu Trp Val Ser Ala Ile Ser Ser Ser Gly Gly
65                  70                  75                  80

Ser Thr Tyr Tyr Ala Asp Ser Val Lys Gly Arg Phe Thr Ile Ser Arg
                85                  90                  95

Asp Asn Ser Lys Asn Thr Val Tyr Leu Gln Met Asn Ser Leu Arg Ala
            100                 105                 110

Glu Asp Thr Ala Val Tyr Tyr Cys Val Arg Ser Pro Lys Gly Cys Thr
        115                 120                 125

His Ala Ser Cys Ser Trp Asn Ser Gly Ser Trp Gly Gln Gly Thr Leu
    130                 135                 140

Val Thr Val Ser Ser
145
```

<210> SEQ ID NO 18
<211> LENGTH: 154
<212> TYPE: PRT
<213> ORGANISM: Homo sapiens

<400> SEQUENCE: 18

Met Lys Ala Ile Phe Val Leu Lys Gly Ser Leu Asp Arg Asp Pro Glu
1               5                   10                  15

Phe Asp Asp Glu Glu Gly Gly Gly Gln Val Gln Leu Val Glu Ser Gly
                20                  25                  30

Gly Gly Leu Ile Lys Pro Gly Gly Ser Leu Arg Leu Ser Cys Ala Ala
            35                  40                  45

Ser Gly Phe Arg Phe Ser Ala Glu Ser Met Thr Trp Val Arg Gln Ala
    50                  55                  60

Pro Gly Lys Gly Leu Glu Trp Val Ser Ala Ile Ser Ser Ser Gly Gly
65                  70                  75                  80

Ser Thr Tyr Tyr Ala Asp Ser Val Lys Gly Arg Phe Thr Ile Ser Arg
                85                  90                  95

Asp Asn Ser Lys Asn Thr Val Tyr Leu Gln Met Asn Ser Leu Arg Ala
                100                 105                 110

Glu Asp Thr Ala Val Tyr Tyr Cys Val Arg Ser Pro Lys Gly Cys Thr
            115                 120                 125

His Ala Ser Cys Ser Trp Asn Ser Gly Ser Trp Gly Gln Gly Thr Leu
        130                 135                 140

Val Thr Val Ser Ser Gly Ser Asp Glu Glu
145                 150

<210> SEQ ID NO 19
<211> LENGTH: 126
<212> TYPE: PRT
<213> ORGANISM: Homo sapiens

<400> SEQUENCE: 19

Met Gln Val Gln Leu Val Glu Ser Gly Gly Gly Leu Ile Lys Pro Gly
1               5                   10                  15

Gly Ser Leu Arg Leu Ser Cys Ala Ala Ser Gly Asp Met Leu Ser Tyr
                20                  25                  30

Asp Val Met Ser Trp Val Arg Gln Ala Pro Gly Lys Gly Leu Glu Trp
            35                  40                  45

Val Ser Ala Ile Ser Ser Ser Gly Gly Ser Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Val Ala Ala Pro Trp Arg Cys Thr His Asp Asn Cys Ser Lys Thr
                100                 105                 110

Arg Ala Ser Trp Gly Gln Gly Thr Met Val Thr Val Ser Ser
            115                 120                 125

<210> SEQ ID NO 20
<211> LENGTH: 140
<212> TYPE: PRT
<213> ORGANISM: Homo sapiens

<400> SEQUENCE: 20

Met Gln Val Gln Leu Val Glu Ser Gly Gly Gly Leu Ile Lys Pro Gly
1               5                   10                  15

Gly Ser Leu Arg Leu Ser Cys Ala Ala Ser Gly Asp Met Leu Ser Tyr
                20                  25                  30

```
Asp Val Met Ser Trp Val Arg Gln Ala Pro Lys Gly Leu Glu Trp
            35                  40                  45

Val Ser Ala Ile Ser Ser Gly Gly Ser Thr Tyr Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Val Ala Ala Pro Trp Arg Cys Thr His Asp Asn Cys Ser Lys Thr
                100                 105                 110

Arg Ala Ser Trp Gly Gln Gly Thr Met Val Thr Val Ser Ser Gly Ser
            115                 120                 125

Glu Gln Lys Gly Gly Gly Glu Glu Asp Asp Glu Glu
            130                 135                 140
```

<210> SEQ ID NO 21
<211> LENGTH: 144
<212> TYPE: PRT
<213> ORGANISM: Homo sapiens

<400> SEQUENCE: 21

```
Met Gln Val Gln Leu Val Glu Ser Gly Gly Gly Leu Ile Lys Pro Gly
 1               5                  10                  15

Gly Ser Leu Arg Leu Ser Cys Ala Ala Ser Gly Asp Met Leu Ser Tyr
             20                  25                  30

Asp Val Met Ser Trp Val Arg Gln Ala Pro Lys Gly Leu Glu Trp
            35                  40                  45

Val Ser Ala Ile Ser Ser Gly Gly Ser Thr Tyr Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Val Ala Ala Pro Trp Arg Cys Thr His Asp Asn Cys Ser Lys Thr
                100                 105                 110

Arg Ala Ser Trp Gly Gln Gly Thr Met Val Thr Val Ser Ser Gly Ser
            115                 120                 125

Glu Gln Lys Leu Ile Ser Glu Glu Asp Leu Asn His His His His
            130                 135                 140
```

<210> SEQ ID NO 22
<211> LENGTH: 128
<212> TYPE: PRT
<213> ORGANISM: Homo sapiens

<400> SEQUENCE: 22

```
Met Lys Lys Gln Val Gln Leu Val Glu Ser Gly Gly Gly Leu Ile Lys
 1               5                  10                  15

Pro Gly Gly Ser Leu Arg Leu Ser Cys Ala Ala Ser Gly Asp Met Leu
             20                  25                  30

Ser Tyr Asp Val Met Ser Trp Val Arg Gln Ala Pro Gly Lys Gly Leu
             35                  40                  45

Glu Trp Val Ser Ala Ile Ser Ser Gly Gly Ser Thr Tyr Tyr Ala
 50                  55                  60

Asp Ser Val Lys Gly Arg Phe Thr Ile Ser Arg Asp Asn Ser Lys Asn
 65                  70                  75                  80
```

Thr Val Tyr Leu Gln Met Asn Ser Leu Arg Ala Glu Asp Thr Ala Val
                85                  90                  95

Tyr Tyr Cys Val Ala Ala Pro Trp Arg Cys Thr His Asp Asn Cys Ser
            100                 105                 110

Lys Thr Arg Ala Ser Trp Gly Gln Gly Thr Met Val Thr Val Ser Ser
        115                 120                 125

<210> SEQ ID NO 23
<211> LENGTH: 137
<212> TYPE: PRT
<213> ORGANISM: Homo sapiens

<400> SEQUENCE: 23

Met Lys Lys Gln Val Gln Leu Val Glu Ser Gly Gly Leu Ile Lys
1               5                   10                  15

Pro Gly Gly Ser Leu Arg Leu Ser Cys Ala Ala Ser Gly Asp Met Leu
            20                  25                  30

Ser Tyr Asp Val Met Ser Trp Val Arg Gln Ala Pro Gly Lys Gly Leu
        35                  40                  45

Glu Trp Val Ser Ala Ile Ser Ser Gly Gly Ser Thr Tyr Tyr Ala
50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Val
                85                  90                  95

Tyr Tyr Cys Val Ala Ala Pro Trp Arg Cys Thr His Asp Asn Cys Ser
            100                 105                 110

Lys Thr Arg Ala Ser Trp Gly Gln Gly Thr Met Val Thr Val Ser Ser
        115                 120                 125

Gly Ser Glu Glu Glu Asp Asp Gly
        130                 135

<210> SEQ ID NO 24
<211> LENGTH: 147
<212> TYPE: PRT
<213> ORGANISM: Homo sapiens

<400> SEQUENCE: 24

Met Gln Val Gln Leu Val Glu Ser Gly Gly Gly Leu Ile Lys Pro Gly
1               5                   10                  15

Gly Ser Leu Arg Leu Ser Cys Ala Ala Ser Gly Asp Met Leu Ser Tyr
            20                  25                  30

Asp Val Met Ser Trp Val Arg Gln Ala Pro Gly Lys Gly Leu Glu Trp
        35                  40                  45

Val Ser Ala Ile Ser Ser Gly Gly Ser Thr Tyr Tyr Ala Asp Ser
50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Val Ala Ala Pro Trp Arg Cys Thr His Asp Asn Cys Ser Lys Thr
            100                 105                 110

Arg Ala Ser Trp Gly Gln Gly Thr Met Val Thr Val Ser Ser Gly Ser
        115                 120                 125

Glu Gln Lys Leu Ile Ser Glu Glu Asp Leu Asn Gly Gly Gly Glu Asp
        130                 135                 140

Glu Gly Cys
145

<210> SEQ ID NO 25
<211> LENGTH: 132
<212> TYPE: PRT
<213> ORGANISM: Lama glama

<400> SEQUENCE: 25

Met Gln Val Lys Leu Glu Glu Ser Gly Gly Gly Leu Val Gln Ala Gly
1               5                   10                  15

Gly Ser Leu Arg Leu Ser Cys Ala Ala Ser Gly Gly Thr Ala Ser Ser
            20                  25                  30

Tyr Ala Met Gly Trp Phe Arg Gln Ala Pro Gly Lys Glu Arg Glu Phe
        35                  40                  45

Val Ala Ala Ile Ser Arg Ser Gly Gly Asn Thr Asp Tyr Val Asp Ser
    50                  55                  60

Ala Lys Gly Arg Phe Thr Ile Ser Arg Asp Asp Ala Lys Asn Thr Val
65                  70                  75                  80

Ser Leu Gln Met Asn Ser Leu Arg Leu Glu Asp Thr Ala Val Tyr Tyr
                85                  90                  95

Cys Ala Ala Arg Tyr Ala Gly Thr Trp Pro Asn Asp Ala Gly Thr Val
            100                 105                 110

Tyr Trp Leu Pro Pro Asn Tyr Asn Tyr Trp Gly Gln Gly Thr Gln Val
        115                 120                 125

Thr Val Ser Ser
    130

<210> SEQ ID NO 26
<211> LENGTH: 136
<212> TYPE: PRT
<213> ORGANISM: Lama glama

<400> SEQUENCE: 26

Met Gln Val Lys Leu Glu Glu Ser Gly Gly Gly Leu Val Gln Ala Gly
1               5                   10                  15

Gly Ser Leu Arg Leu Ser Cys Ala Ala Ser Gly Gly Thr Ala Ser Ser
            20                  25                  30

Tyr Ala Met Gly Trp Phe Arg Gln Ala Pro Gly Lys Glu Arg Glu Phe
        35                  40                  45

Val Ala Ala Ile Ser Arg Ser Gly Gly Asn Thr Asp Tyr Val Asp Ser
    50                  55                  60

Ala Lys Gly Arg Phe Thr Ile Ser Arg Asp Asp Ala Lys Asn Thr Val
65                  70                  75                  80

Ser Leu Gln Met Asn Ser Leu Arg Leu Glu Asp Thr Ala Val Tyr Tyr
                85                  90                  95

Cys Ala Ala Arg Tyr Ala Gly Thr Trp Pro Asn Asp Ala Gly Thr Val
            100                 105                 110

Tyr Trp Leu Pro Pro Asn Tyr Asn Tyr Trp Gly Gln Gly Thr Gln Val
        115                 120                 125

Thr Val Ser Ser Gly Ser Glu Gln
    130                 135

<210> SEQ ID NO 27
<211> LENGTH: 151
<212> TYPE: PRT
<213> ORGANISM: Lama glama

```
<400> SEQUENCE: 27

Met Gln Val Lys Leu Glu Glu Ser Gly Gly Gly Leu Val Gln Ala Gly
1               5                   10                  15

Gly Ser Leu Arg Leu Ser Cys Ala Ala Ser Gly Gly Thr Ala Ser Ser
                20                  25                  30

Tyr Ala Met Gly Trp Phe Arg Gln Ala Pro Gly Lys Glu Arg Glu Phe
            35                  40                  45

Val Ala Ala Ile Ser Arg Ser Gly Gly Asn Thr Asp Tyr Val Asp Ser
    50                  55                  60

Ala Lys Gly Arg Phe Thr Ile Ser Arg Asp Asp Ala Lys Asn Thr Val
65                  70                  75                  80

Ser Leu Gln Met Asn Ser Leu Arg Leu Glu Asp Thr Ala Val Tyr Tyr
                85                  90                  95

Cys Ala Ala Arg Tyr Ala Gly Thr Trp Pro Asn Asp Ala Gly Thr Val
            100                 105                 110

Tyr Trp Leu Pro Pro Asn Tyr Asn Tyr Trp Gly Gln Gly Thr Gln Val
        115                 120                 125

Thr Val Ser Ser Gly Ser Glu Gln Lys Leu Ile Ser Glu Glu Asp Leu
    130                 135                 140

Asn His His His His His His
145                 150

<210> SEQ ID NO 28
<211> LENGTH: 131
<212> TYPE: PRT
<213> ORGANISM: Lama glama

<400> SEQUENCE: 28

Gln Val Lys Leu Glu Glu Ser Gly Gly Gly Leu Val Gln Ala Gly Gly
1               5                   10                  15

Ser Leu Arg Leu Ser Cys Ala Ala Ser Gly Gly Thr Ala Ser Ser Tyr
                20                  25                  30

Ala Met Gly Trp Phe Arg Gln Ala Pro Gly Lys Glu Arg Glu Phe Val
            35                  40                  45

Ala Ala Ile Ser Arg Ser Gly Gly Asn Thr Asp Tyr Val Asp Ser Ala
    50                  55                  60

Lys Gly Arg Phe Thr Ile Ser Arg Asp Asp Ala Lys Asn Thr Val Ser
65                  70                  75                  80

Leu Gln Met Asn Ser Leu Arg Leu Glu Asp Thr Ala Val Tyr Tyr Cys
                85                  90                  95

Ala Ala Arg Tyr Ala Gly Thr Trp Pro Asn Asp Ala Gly Thr Val Tyr
            100                 105                 110

Trp Leu Pro Pro Asn Tyr Asn Tyr Trp Gly Gln Gly Thr Gln Val Thr
        115                 120                 125

Val Ser Ser
    130

<210> SEQ ID NO 29
<211> LENGTH: 150
<212> TYPE: PRT
<213> ORGANISM: Lama glama

<400> SEQUENCE: 29

Gln Val Lys Leu Glu Glu Ser Gly Gly Gly Leu Val Gln Ala Gly Gly
1               5                   10                  15

Ser Leu Arg Leu Ser Cys Ala Ala Ser Gly Gly Thr Ala Ser Ser Tyr
```

```
            20                  25                  30
Ala Met Gly Trp Phe Arg Gln Ala Pro Gly Lys Glu Arg Glu Phe Val
         35                  40                  45

Ala Ala Ile Ser Arg Ser Gly Gly Asn Thr Asp Tyr Val Asp Ser Ala
 50                  55                  60

Lys Gly Arg Phe Thr Ile Ser Arg Asp Asp Ala Lys Asn Thr Val Ser
 65                  70                  75                  80

Leu Gln Met Asn Ser Leu Arg Leu Glu Asp Thr Ala Val Tyr Tyr Cys
                 85                  90                  95

Ala Ala Arg Tyr Ala Gly Thr Trp Pro Asn Asp Ala Gly Thr Val Tyr
            100                 105                 110

Trp Leu Pro Pro Asn Tyr Asn Tyr Trp Gly Gln Gly Thr Gln Val Thr
            115                 120                 125

Val Ser Ser Gly Ser Glu Gln Lys Leu Ile Ser Glu Glu Asp Leu Asn
            130                 135                 140

His His His His His His
145                 150

<210> SEQ ID NO 30
<211> LENGTH: 145
<212> TYPE: PRT
<213> ORGANISM: Lama glama

<400> SEQUENCE: 30

Met Gln Val Lys Leu Glu Glu Ser Gly Gly Gly Leu Val Gln Ala Gly
 1               5                  10                  15

Gly Ser Leu Arg Leu Ser Cys Ala Ala Ser Gly Gly Thr Ala Ser Ser
             20                  25                  30

Tyr Ala Met Gly Trp Phe Arg Gln Ala Pro Gly Lys Glu Arg Glu Phe
         35                  40                  45

Val Ala Ala Ile Ser Arg Ser Gly Gly Asn Thr Asp Tyr Val Asp Ser
 50                  55                  60

Ala Lys Gly Arg Phe Thr Ile Ser Arg Asp Asp Ala Lys Asn Thr Val
 65                  70                  75                  80

Ser Leu Gln Met Asn Ser Leu Arg Leu Glu Asp Thr Ala Val Tyr Tyr
                 85                  90                  95

Cys Ala Ala Arg Tyr Ala Gly Thr Trp Pro Asn Asp Ala Gly Thr Val
            100                 105                 110

Tyr Trp Leu Pro Pro Asn Tyr Asn Tyr Trp Gly Gln Gly Thr Gln Val
            115                 120                 125

Thr Val Ser Ser Gly Ser Glu Gln Lys Gly Gly Gly Asp Glu Asp Gly
            130                 135                 140

Cys
145

<210> SEQ ID NO 31
<211> LENGTH: 366
<212> TYPE: DNA
<213> ORGANISM: Lama glama

<400> SEQUENCE: 31
atgcaggtgc agctggtgga atccggcggc ggcctggtgc aggcgggcgg ctccctgcgt     60
ctgtcctgcg cggcgtccgg ccgtgcgttt cctcctatg cgatgggctg gtttcgtcag    120
gcgccgggca agaacgtga actggtggcg gcgattcct ggtccgatga ttccacctat    180
tatgcgaatt ccgtgaaagg ccgttttacc atttcccgtg ataatgcgaa atccgcggtg    240
```

| | |
|---|---|
| tatctacaga tgaattccct gaaaccggaa gataccgcgg tgtattattg cgcggcgcat | 300 |
| aaatccctac agcgtccgga tgaatatacc tattggggcc agggcaccca ggtgaccgtg | 360 |
| tcctcc | 366 |

<210> SEQ ID NO 32
<211> LENGTH: 366
<212> TYPE: DNA
<213> ORGANISM: Lama glama

<400> SEQUENCE: 32

| | |
|---|---|
| atgcaggtgc agcttgtgga gtccggcgga ggtcttgtcc aggcaggagg gtctttgcgc | 60 |
| ctgagctgcg cggcgagtgg gcgcgcgttc agcagttacg cgatggggttg gttccgccag | 120 |
| gcccctggga agagcgtga acttgtggct gccatttctt ggtctgatga ttccacctat | 180 |
| tatgctaatt cagttaaggg ccgtttcacg attagccgcg ataatgctaa atccgccgtc | 240 |
| tatcttcaga tgaacagcct taagcctgaa gatacgcag tatattattg tgccgctcat | 300 |
| aagagtctgc aacgcccgga cgaatataca tactggggac agggcacgca agttaccgtt | 360 |
| tccagc | 366 |

<210> SEQ ID NO 33
<211> LENGTH: 405
<212> TYPE: DNA
<213> ORGANISM: Lama glama

<400> SEQUENCE: 33

| | |
|---|---|
| atgcaggtgc agctggtgga atccggcggc ggcctggtgc aggcgggcgg ctccctgcgt | 60 |
| ctgtcctgcg cggcgtccgg ccgtgcgttt cctcctatg cgatgggctg gtttcgtcag | 120 |
| gcgccgggca agaacgtga actggtggcg gcgatttcct ggtccgatga ttccacctat | 180 |
| tatgcgaatt ccgtgaaagg ccgtttttacc atttcccgtg ataatgcgaa atccgcggtg | 240 |
| tatctacaga tgaattccct gaaaccggaa gataccgcgg tgtattattg cgcggcgcat | 300 |
| aaatccctac agcgtccgga tgaatatacc tattggggcc agggcaccca ggtgaccgtg | 360 |
| tcctccggct ccgaacagaa aggcggcggc gaagaagatg atggc | 405 |

<210> SEQ ID NO 34
<211> LENGTH: 423
<212> TYPE: DNA
<213> ORGANISM: Lama glama

<400> SEQUENCE: 34

| | |
|---|---|
| atgcaggtgc aactggttga atcaggtgga ggactggtgc aggccggggg atctttacgc | 60 |
| ttatcatgtg cagcttcggg gcgtgccttc tcctcttatg cgatgggatg gttccgccaa | 120 |
| gcccccggca aggagcgtga gctggtagca gccatttcct ggtcagacga cagtacctac | 180 |
| tacgcaaact cagtcaaagg cgcttcact atctctcgcg acaatgccaa atccgctgtg | 240 |
| tacttgcaaa tgaactcatt gaagccagag gatacggctg tctattactg tgcagcccac | 300 |
| aagagtttac agcgtccaga tgaataacacc tattggggac aaggtacaca agttaccgtt | 360 |
| agttcgggta gcgaacaaaa gttgatctct gaggaggact aaaatcatca tcatcatcac | 420 |
| cat | 423 |

<210> SEQ ID NO 35
<211> LENGTH: 408
<212> TYPE: DNA

<213> ORGANISM: Lama glama

<400> SEQUENCE: 35

| | |
|---|---|
| atgcaggtgc agcttgtgga gtccggcgga ggtcttgtcc aggcaggagg gtctttgcgc | 60 |
| ctgagctgcg cggcgagtgg gcgcgcgttc agcagttacg cgatgggttg gttccgccag | 120 |
| gcccctggga agagcgtga acttgtggct gccatttctt ggtctgatga ttccacctat | 180 |
| tatgctaatt cagttaaggg ccgtttcacg attagccgcg ataatgctaa atccgccgtc | 240 |
| tatcttcaga tgaacagcct taagcctgaa gatacggcag tatattattg tgccgctcat | 300 |
| aagagtctgc aacgcccgga cgaatataca tactggggac agggcacgca agttaccgtt | 360 |
| tccagcggtt ctgaacagaa aggaggcggt gaagaggatg atggctgc | 408 |

<210> SEQ ID NO 36
<211> LENGTH: 432
<212> TYPE: DNA
<213> ORGANISM: Lama glama

<400> SEQUENCE: 36

| | |
|---|---|
| atgaaagcga tcttcgttct gaaaggttct ctggaccgtg acccggaatt cgacgacgaa | 60 |
| ggtggtggtc aggttcagct ggttgaatct ggtggtggtc tggttcaggc gggtggttct | 120 |
| ctgcgtctgt cttgcgcggc gtctggtcgt gcgttctctt cttacgcgat gggttggttc | 180 |
| cgtcaggcgc cgggtaaaga acgtgaactg gttgcggcga tctcttggtc tgacgactct | 240 |
| acctactacg cgaactctgt taaaggtcgt ttcaccatct ctcgtgacaa cgcgaaatct | 300 |
| gcggtttacc tacagatgaa ctctctgaaa ccggaagaca ccgcggttta ctactgcgcg | 360 |
| gcgcacaaat ctctacagcg tccggacgaa tacacctact ggggtcaggg tacccaggtt | 420 |
| accgtttctt ct | 432 |

<210> SEQ ID NO 37
<211> LENGTH: 444
<212> TYPE: DNA
<213> ORGANISM: Lama glama

<400> SEQUENCE: 37

| | |
|---|---|
| atgaaagcga tcttcgttct gaaaggttct ctggaccgtg acccggaatt cgacgacgaa | 60 |
| ggtggtggtc aggttcagct ggttgaatct ggtggtggtc tggttcaggc gggtggttct | 120 |
| ctgcgtctgt cttgcgcggc gtctggtcgt gcgttctctt cttacgcgat gggttggttc | 180 |
| cgtcaggcgc cgggtaaaga acgtgaactg gttgcggcga tctcttggtc tgacgactct | 240 |
| acctactacg cgaactctgt taaaggtcgt ttcaccatct ctcgtgacaa cgcgaaatct | 300 |
| gcggtttacc tacagatgaa ctctctgaaa ccggaagaca ccgcggttta ctactgcgcg | 360 |
| gcgcacaaat ctctacagcg tccggacgaa tacacctact ggggtcaggg tacccaggtt | 420 |
| accgtttctt ctggttctga acag | 444 |

<210> SEQ ID NO 38
<211> LENGTH: 378
<212> TYPE: DNA
<213> ORGANISM: Homo sapiens

<400> SEQUENCE: 38

| | |
|---|---|
| atgcaagttc agttagtaga aagtggtggt ggtttaatca aaccgggtgg ttcacttcgt | 60 |
| ttatcgtgcg cagcaagcgg gtttcgtttt tcagcagaat caatgacatg ggttcgtcaa | 120 |
| gcaccgggca aaggtttaga gtgggtttca gcaatttcat caagtggcgg ttcaacttat | 180 |

```
tatgcagatt cggttaaagg tcgtttcaca atttctcgcg ataactcaaa aaatacggtt      240
tatttacaaa tgaattcctt acgtgcagaa gatacagcag tttattattg tgttcgttct      300
ccaaaaggtt gtactcacgc atcttgtagt tggaatagtg gtagttgggg tcaaggtaca      360
ttagttacag tctcaagc                                                   378

<210> SEQ ID NO 39
<211> LENGTH: 378
<212> TYPE: DNA
<213> ORGANISM: Homo sapiens

<400> SEQUENCE: 39
atgcaggtgc agttagttga gtcgggcggg ggtcttatta aaccaggtgg aagccttcgt      60
ctgtcttgtg cagcatcagg cttcgtttt tccgcggaaa gcatgacctg ggtacgccaa      120
gcgcctggca aaggattgga gtgggtttcg gccatttctt cttcaggagg atcaacgtac      180
tatgcagact ccgtaaaagg acgcttcacg atttctcgcg ataactctaa gaacaccgtg      240
tacttacaaa tgaactcttt acgtgcagag gacacagcag tgtattattg tgttcgctca      300
cccaaaggct gcacccatgc gtcatgctct tggaactcag gttcgtgggg ccaggggacc      360
ttggtgacag tatcctcg                                                   378

<210> SEQ ID NO 40
<211> LENGTH: 408
<212> TYPE: DNA
<213> ORGANISM: Homo sapiens

<400> SEQUENCE: 40
atgcaagttc agttagtaga aagtggtggt ggtttaatca aaccgggtgg ttcacttcgt      60
ttatcgtgcg cagcaagcgg gtttcgtttt tcagcagaat caatgacatg ggttcgtcaa      120
gcaccgggca aaggtttaga gtgggtttca gcaatttcat caagtggcgg ttcaacttat      180
tatgcagatt cggttaaagg tcgtttcaca atttctcgcg ataactcaaa aaatacggtt      240
tatttacaaa tgaattcctt acgtgcagaa gatacagcag tttattattg tgttcgttct      300
ccaaaaggtt gtactcacgc atcttgtagt tggaatagtg gtagttgggg tcaaggtaca      360
ttagttacag tctcaagcgg ttcagaagaa gatgacgatg aagaaaaa                  408

<210> SEQ ID NO 41
<211> LENGTH: 432
<212> TYPE: DNA
<213> ORGANISM: Homo sapiens

<400> SEQUENCE: 41
atgcaggtgc agttagttga gtcgggcggg ggtcttatta aaccaggtgg aagccttcgt      60
ctgtcttgtg cagcatcagg cttcgtttt tccgcggaaa gcatgacctg ggtacgccaa      120
gcgcctggca aaggattgga gtgggtttcg gccatttctt cttcaggagg atcaacgtac      180
tatgcagact ccgtaaaagg acgcttcacg atttctcgcg ataactctaa gaacaccgtg      240
tacttacaaa tgaactcttt acgtgcagag gacacagcag tgtattattg tgttcgctca      300
cccaaaggct gcacccatgc gtcatgctct tggaactcag gttcgtgggg ccaggggacc      360
ttggtgacag tatcctcggg ctccgaacag aagttaatta gtgaagaaga tttgaaccac      420
caccaccatc ac                                                         432

<210> SEQ ID NO 42
```

<210> SEQ ID NO 42
<211> LENGTH: 447
<212> TYPE: DNA
<213> ORGANISM: Homo sapiens

<400> SEQUENCE: 42

```
atgaaagcga tcttcgttct gaaaggttct ctggaccgtg acccggaatt cgacgacgaa    60
gaaggtggtg gtcaggttca gctggttgaa tctggtggtg gtctgatcaa accgggtggt   120
tctctgcgtc tgtcttgcgc ggcgtctggt ttccgtttct ctgcggaatc tatgacctgg   180
gttcgtcagg cgccgggtaa aggtctggaa tgggtttctg cgatctcttc ttctggtggt   240
tctacctact acgcggactc tgttaaaggt cgtttcacca tctctcgtga caactctaaa   300
aacaccgttt acttacaaat gaactctctg cgtgcggaag acaccgcggt ttactactgc   360
gttcgttctc cgaaaggttg cacccacgcg tcttgctctt ggaactctgg ttcttggggt   420
cagggtaccc tggttaccgt ttcttct                                       447
```

<210> SEQ ID NO 43
<211> LENGTH: 462
<212> TYPE: DNA
<213> ORGANISM: Homo sapiens

<400> SEQUENCE: 43

```
atgaaagcga tcttcgttct gaaaggttct ctggaccgtg acccggaatt cgacgacgaa    60
gaaggtggtg gtcaggttca gctggttgaa tctggtggtg gtctgatcaa accgggtggt   120
tctctgcgtc tgtcttgcgc ggcgtctggt ttccgtttct ctgcggaatc tatgacctgg   180
gttcgtcagg cgccgggtaa aggtctggaa tgggtttctg cgatctcttc ttctggtggt   240
tctacctact acgcggactc tgttaaaggt cgtttcacca tctctcgtga caactctaaa   300
aacaccgttt acttacaaat gaactctctg cgtgcggaag acaccgcggt ttactactgc   360
gttcgttctc cgaaaggttg cacccacgcg tcttgctctt ggaactctgg ttcttggggt   420
cagggtaccc tggttaccgt ttcttctggt tctgacgaag aa                      462
```

<210> SEQ ID NO 44
<211> LENGTH: 372
<212> TYPE: DNA
<213> ORGANISM: Homo sapiens

<400> SEQUENCE: 44

```
atgcaggtgc agctggtgga aagcggcggc ggcctgatta aaccgggcgg cagcctgcgc    60
ctgagctgcg cggcgagcgg cgatatgctg agctatgatg tgatgagctg ggtgcgccag   120
gcgccgggca aaggcctgga atgggtgagc gcgattagca gcagcggcgg cagcacctat   180
tatgcggata gcgtgaaagg ccgctttacc attagccgcg ataacagcaa aaacaccgtg   240
tatcttcaga tgaacagcct gcgcgcggaa gataccgcgg tgtattattg cgtggcggcg   300
ccgtggcgct gcacccatga taactgctct aaaacccgcg cgagctgggg ccagggcacc   360
atggtgaccg tg                                                       372
```

<210> SEQ ID NO 45
<211> LENGTH: 378
<212> TYPE: DNA
<213> ORGANISM: Homo sapiens

<400> SEQUENCE: 45

```
atgcaagtac agttagtgga gagtggagga gggctgatta agccaggcgg ctctttgcgt    60
ctgagttgtg cggcatcagg cgatatgtta agctacgatg tgatgagttg ggtgcgtcaa   120
```

| | |
|---|---|
| gcgccaggaa aaggacttga atgggtcagc gcaatttcgt cgtccggtgg gtctacttac | 180 |
| tacgctgatt cggttaaggg ccgcttcacc atctcccgcg acaattcaaa gaatacggta | 240 |
| tatctgcaaa tgaatagttt gcgtgcggag gacacagcag tctactattg cgttgcagct | 300 |
| ccctggcgct gtactcacga taactgttca aaaacccgcg catcatgggg tcaaggtaca | 360 |
| atggtgacag tgtcatct | 378 |

<210> SEQ ID NO 46
<211> LENGTH: 420
<212> TYPE: DNA
<213> ORGANISM: Homo sapiens

<400> SEQUENCE: 46

| | |
|---|---|
| atgcaggtgc agctggtgga aagcggcggc ggcctgatta accgggcgg cagcctgcgc | 60 |
| ctgagctgcg cggcgagcgg cgatatgctg agctatgatg tgatgagctg ggtgcgccag | 120 |
| gcgccgggca aaggcctgga atgggtgagc gcgattagca gcagcggcgg cagcaccctat | 180 |
| tatgcggata gcgtgaaagg ccgctttacc attagccgcg ataacagcaa aaacaccgtg | 240 |
| tatcttcaga tgaacagcct gcgcgcgaa gataccgcgg tgtattattg cgtgcggcg | 300 |
| ccgtggcgct gcacccatga taactgctct aaaaacccgcg cgagctgggg ccagggcacc | 360 |
| atggtgaccg tgagcagcgg cagcgaacag aaaggcggcg gcgaagaaga tgatgaagaa | 420 |

<210> SEQ ID NO 47
<211> LENGTH: 432
<212> TYPE: DNA
<213> ORGANISM: Homo sapiens

<400> SEQUENCE: 47

| | |
|---|---|
| atgcaagtac agttagtgga gagtggagga gggctgatta agccaggcgg ctctttgcgt | 60 |
| ctgagttgtg cggcatcagg cgatatgtta agctacgatg tgatgagttg ggtgcgtcaa | 120 |
| gcgccaggaa aaggacttga atgggtcagc gcaatttcgt cgtccggtgg gtctacttac | 180 |
| tacgctgatt cggttaaggg ccgcttcacc atctcccgcg acaattcaaa gaatacggta | 240 |
| tatctgcaaa tgaatagttt gcgtgcggag gacacagcag tctactattg cgttgcagct | 300 |
| ccctggcgct gtactcacga taactgttca aaaacccgcg catcatgggg tcaaggtaca | 360 |
| atggtgacag tgtcatctgg tagtgaacag aagttaatta gtgaagagga ccttaatcat | 420 |
| catcatcatc ac | 432 |

<210> SEQ ID NO 48
<211> LENGTH: 441
<212> TYPE: DNA
<213> ORGANISM: Homo sapiens

<400> SEQUENCE: 48

| | |
|---|---|
| atgcaggttc agctggttga atctggtggt ggtctgatca aaccgggtgg ttctctgcgt | 60 |
| ctgtcttgcg cggcgtctgg tgacatgctg tcttacgacg ttatgtcttg ggttcgtcag | 120 |
| gcgccgggta aggtctgga atgggttct gcgatctctt cttctggtgg ttctacctac | 180 |
| tacgcggact ctgttaaagg tcgtttcacc atctctcgtg acaactctaa aaacaccgtt | 240 |
| tacctgcaaa tgaactctct gcgtgcggaa gacaccgcgg tttactactg cgttgcggcg | 300 |
| ccgtggcgtt gcacccacga caactgctct aaaaacccgtg cgtcttgggg tcagggtacc | 360 |
| atggttaccg tttcttctgg ttctgaacag aaactgatct ctgaagaaga cctgaacggt | 420 |

```
ggtggtgaag acgaaggttg c                                            441
```

<210> SEQ ID NO 49
<211> LENGTH: 396
<212> TYPE: DNA
<213> ORGANISM: Lama glama

<400> SEQUENCE: 49

```
atgcaagtaa aactcgaaga atcaggtgga ggattggttc aagctggtgg gtcattacgt    60
ttgtcctgtg cagcaagtgg cggtactgcg tcaagttatg caatgggttg gtttcgtcaa   120
gctcccggta agaacgtga atttgttgcc gcaattagtc ggtccggagg aaatacagat    180
tatgtagact cagcaaaagg tcgttttact atctcacgcg atgatgcaaa aaatacggtt   240
tccttacaaa tgaactctct gcgcctcgaa gataccgcgg tatattattg cgctgcccgc   300
tacgccggta cctggccgaa tgatgctggc actgtatatt ggctgccacc gaattacaac   360
tattggggtc aaggaactca agtcacggta agcagc                             396
```

<210> SEQ ID NO 50
<211> LENGTH: 396
<212> TYPE: DNA
<213> ORGANISM: Lama glama

<400> SEQUENCE: 50

```
atgcaggtta aattagagga atcaggtgga ggtttggttc aagcaggtgg tagcttgcgc    60
ctgagttgtg ccgctagcgg gggcacagcc agttcatacg cgatggggtg gtttcgccag   120
gccccctggaa aggagcgtga attcgttgct gcgattagtc gtagcggcgg taacacggat   180
tacgtggaca gcgcgaaggg acgctttaca atttctcgtg atgacgcaaa gaacacggtg   240
tccctgcaaa tgaactcact tcgcctgaaa gacaccgcgg tgtattattg tgcagcccgc   300
tacgcgggaa cttggccgaa cgatgctggt accgtgtact ggttaccccc taattacaat   360
tactggggcc aaggtaccca agtcaccgtc tcctcg                             396
```

<210> SEQ ID NO 51
<211> LENGTH: 438
<212> TYPE: DNA
<213> ORGANISM: Lama glama

<400> SEQUENCE: 51

```
atgcaagtaa aactcgaaga atcaggtgga ggattggttc aagctggtgg gtcattacgt    60
ttgtcctgtg cagcaagtgg cggtactgcg tcaagttatg caatgggttg gtttcgtcaa   120
gctcccggta agaacgtga atttgttgcc gcaattagtc ggtccggagg aaatacagat    180
tatgtagact cagcaaaagg tcgttttact atctcacgcg atgatgcaaa aaatacggtt   240
tccttacaaa tgaactctct gcgcctcgaa gataccgcgg tatattattg cgctgcccgc   300
tacgccggta cctggccgaa tgatgctggc actgtatatt ggctgccacc gaattacaac   360
tattggggtc aaggaactca agtcacggta agcagcggtt ccgaacaaaa gggtggtgga   420
gaagaagatg atggcaaa                                                 438
```

<210> SEQ ID NO 52
<211> LENGTH: 453
<212> TYPE: DNA
<213> ORGANISM: Lama glama

<400> SEQUENCE: 52

```
atgcaggtta aattagagga atcaggtgga ggtttggttc aagcaggtgg tagcttgcgc    60
```

```
ctgagttgtg ccgctagcgg gggcacagcc agttcatacg cgatggggtg gtttcgccag    120
gcccctggaa aggagcgtga attcgttgct gcgattagtc gtagcggcgg taacacggat    180
tacgtggaca gcgcgaaggg acgctttaca atttctcgtg atgacgcaaa gaacacggtg    240
tccctgcaaa tgaactcact tcgcctggaa gacaccgcgg tgtattattg tgcagcccgc    300
tacgcgggaa cttggccgaa cgatgctggt accgtgtact ggttaccccc taattacaat    360
tactggggcc aaggtaccca gtcaccgtc tcctcgggaa gcgaacaaaa gctgattagc    420
gaagaggatc ttaaccatca tcatcaccat cac                                  453

<210> SEQ ID NO 53
<211> LENGTH: 435
<212> TYPE: DNA
<213> ORGANISM: Lama glama

<400> SEQUENCE: 53
atgcaggtta aactggaaga atctggtggt ggtctggttc aggcgggtgg ttctctgcgt     60
ctgtcttgcg cggcgtctgg tggtaccgcg tcttcttacg cgatgggttg gttccgtcag    120
gcgccgggta agaacgtga attcgttgcg gcgatctctc gttctggtgg taacaccgac    180
tacgttgact ctgcgaaagg tcgtttcacc atctctcgtg acgacgcgaa aaacaccgtt    240
tctctgcaaa tgaactctct gcgtctggaa gacaccgcgg tttactactg cgcggcgcgt    300
tacgcgggta cctggccgaa cgacgcgggt accgtttact ggctgccgcc gaactacaac    360
tactggggtc agggtaccca ggttaccgtt tcttctggtt ctgaacagaa aggtggtggt    420
gacgaagacg gttgc                                                      435

<210> SEQ ID NO 54
<211> LENGTH: 4
<212> TYPE: PRT
<213> ORGANISM: Artificial Sequence
<220> FEATURE:
<223> OTHER INFORMATION: Linker

<400> SEQUENCE: 54

Gly Ser Glu Gln
1

<210> SEQ ID NO 55
<211> LENGTH: 5
<212> TYPE: PRT
<213> ORGANISM: Artificial Sequence
<220> FEATURE:
<223> OTHER INFORMATION: Linker

<400> SEQUENCE: 55

Gly Ser Asp Glu Glu
1               5

<210> SEQ ID NO 56
<211> LENGTH: 9
<212> TYPE: PRT
<213> ORGANISM: Artificial Sequence
<220> FEATURE:
<223> OTHER INFORMATION: Linker

<400> SEQUENCE: 56

Gly Ser Glu Glu Glu Asp Asp Asp Gly
1               5
```

```
<210> SEQ ID NO 57
<211> LENGTH: 11
<212> TYPE: PRT
<213> ORGANISM: Artificial Sequence
<220> FEATURE:
<223> OTHER INFORMATION: Linker

<400> SEQUENCE: 57

Gly Ser Glu Glu Glu Asp Asp Asp Gly Lys Lys
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Linker

<400> SEQUENCE: 58

Gly Ser Glu Gln Lys Gly Gly Gly Glu Glu Asp Asp Gly
1               5                   10

<210> SEQ ID NO 59
<211> LENGTH: 18
<212> TYPE: PRT
<213> ORGANISM: Artificial Sequence
<220> FEATURE:
<223> OTHER INFORMATION: Linker

<400> SEQUENCE: 59

Gly Ser Glu Gln Lys Leu Ile Ser Glu Glu Asp Leu Asn His His
1               5                   10                  15

His His

<210> SEQ ID NO 60
<211> LENGTH: 19
<212> TYPE: PRT
<213> ORGANISM: Artificial Sequence
<220> FEATURE:
<223> OTHER INFORMATION: Linker

<400> SEQUENCE: 60

Gly Ser Glu Gln Lys Leu Ile Ser Glu Asp Leu Asn His His His
1               5                   10                  15

His His His

<210> SEQ ID NO 61
<211> LENGTH: 10
<212> TYPE: PRT
<213> ORGANISM: Artificial Sequence
<220> FEATURE:
<223> OTHER INFORMATION: Linker

<400> SEQUENCE: 61

Gly Ser Glu Glu Asp Asp Asp Glu Glu Lys
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Linker

<400> SEQUENCE: 62

Gly Ser Glu Gln Lys Gly Gly Gly Glu Glu Asp Asp Glu Glu
```

<210> SEQ ID NO 63
<211> LENGTH: 22
<212> TYPE: PRT
<213> ORGANISM: Artificial Sequence
<220> FEATURE:
<223> OTHER INFORMATION: Linker

<400> SEQUENCE: 63

Gly Ser Glu Gln Lys Leu Ile Ser Glu Glu Asp Leu Asn Gly Gly Gly
1               5                   10                  15

Glu Asp Asp Glu Glu Gly
            20

<210> SEQ ID NO 64
<211> LENGTH: 20
<212> TYPE: PRT
<213> ORGANISM: Artificial Sequence
<220> FEATURE:
<223> OTHER INFORMATION: Linker

<400> SEQUENCE: 64

Gly Ser Glu Gln Lys Leu Ile Ser Glu Glu Asp Leu Asn Gly Gly Gly
1               5                   10                  15

Glu Asp Glu Gly
            20

<210> SEQ ID NO 65
<211> LENGTH: 12
<212> TYPE: PRT
<213> ORGANISM: Artificial Sequence
<220> FEATURE:
<223> OTHER INFORMATION: Linker

<400> SEQUENCE: 65

Gly Ser Glu Gln Lys Gly Gly Gly Asp Glu Asp Gly
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Linker

<400> SEQUENCE: 66

Gly Ser Glu Gln Lys Gly Gly Gly Glu Glu Asp Asp Gly Cys
1               5                   10

<210> SEQ ID NO 67
<211> LENGTH: 23
<212> TYPE: PRT
<213> ORGANISM: Artificial Sequence
<220> FEATURE:
<223> OTHER INFORMATION: Linker

<400> SEQUENCE: 67

Gly Ser Glu Gln Lys Leu Ile Ser Glu Glu Asp Leu Asn Gly Gly Gly
1               5                   10                  15

Glu Asp Asp Glu Glu Gly Cys
            20

<210> SEQ ID NO 68
<211> LENGTH: 21

```
<212> TYPE: PRT
<213> ORGANISM: Artificial Sequence
<220> FEATURE:
<223> OTHER INFORMATION: Linker

<400> SEQUENCE: 68

Gly Ser Glu Gln Lys Leu Ile Ser Glu Glu Asp Leu Asn Gly Gly Gly
1               5                   10                  15

Glu Asp Glu Gly Cys
            20

<210> SEQ ID NO 69
<211> LENGTH: 13
<212> TYPE: PRT
<213> ORGANISM: Artificial Sequence
<220> FEATURE:
<223> OTHER INFORMATION: Linker

<400> SEQUENCE: 69

Gly Ser Glu Gln Lys Gly Gly Gly Asp Glu Asp Gly Cys
1               5                   10

<210> SEQ ID NO 70
<211> LENGTH: 8
<212> TYPE: PRT
<213> ORGANISM: Artificial Sequence
<220> FEATURE:
<223> OTHER INFORMATION: Flag tag

<400> SEQUENCE: 70

Asp Tyr Lys Asp Asp Asp Asp Lys
1               5

<210> SEQ ID NO 71
<211> LENGTH: 20
<212> TYPE: PRT
<213> ORGANISM: Artificial Sequence
<220> FEATURE:
<223> OTHER INFORMATION: Fusion partner

<400> SEQUENCE: 71

Met Lys Ala Ile Phe Val Leu Lys Gly Ser Leu Asp Arg Asp Pro Glu
1               5                   10                  15

Phe Asp Asp Glu
            20

<210> SEQ ID NO 72
<211> LENGTH: 9
<212> TYPE: PRT
<213> ORGANISM: Artificial Sequence
<220> FEATURE:
<223> OTHER INFORMATION: Variable modifier
<220> FEATURE:
<221> NAME/KEY: MISC_FEATURE
<222> LOCATION: (9)..(9)
<223> OTHER INFORMATION: BM(PEG)2 modifed residue

<400> SEQUENCE: 72

Gly Gly Gly Glu Glu Asp Asp Gly Cys
1               5

<210> SEQ ID NO 73
<211> LENGTH: 9
<212> TYPE: PRT
<213> ORGANISM: Artificial Sequence
<220> FEATURE:
<223> OTHER INFORMATION: Cross-linker activated peptide
```

```
<220> FEATURE:
<221> NAME/KEY: MISC_FEATURE
<222> LOCATION: (9)..(9)
<223> OTHER INFORMATION: BM(PEG)2-Cys modified residue

<400> SEQUENCE: 73

Gly Gly Gly Glu Glu Asp Asp Gly Cys
1               5

<210> SEQ ID NO 74
<211> LENGTH: 8
<212> TYPE: PRT
<213> ORGANISM: Artificial Sequence
<220> FEATURE:
<223> OTHER INFORMATION: Cross-linker activated peptide
<220> FEATURE:
<221> NAME/KEY: MISC_FEATURE
<222> LOCATION: (8)..(8)
<223> OTHER INFORMATION: BM(PEG)2-Cys modified residue

<400> SEQUENCE: 74

Leu Ser Cys Ala Ala Ser Gly Arg
1               5

<210> SEQ ID NO 75
<211> LENGTH: 24
<212> TYPE: PRT
<213> ORGANISM: Artificial Sequence
<220> FEATURE:
<223> OTHER INFORMATION: Cross-linker activated peptide
<220> FEATURE:
<221> NAME/KEY: MISC_FEATURE
<222> LOCATION: (24)..(24)
<223> OTHER INFORMATION: BM(PEG)2-Cys modified residue

<400> SEQUENCE: 75

Ser Ala Val Tyr Leu Gln Met Asn Ser Leu Lys Pro Glu Asp Thr Ala
1               5                   10                  15

Val Tyr Tyr Cys Ala Ala His Lys
            20

<210> SEQ ID NO 76
<211> LENGTH: 9
<212> TYPE: PRT
<213> ORGANISM: Artificial Sequence
<220> FEATURE:
<223> OTHER INFORMATION: Linker

<400> SEQUENCE: 76

Gly Gly Gly Glu Glu Asp Asp Gly Cys
1               5

<210> SEQ ID NO 77
<211> LENGTH: 14
<212> TYPE: PRT
<213> ORGANISM: Canavalia ensiformis

<400> SEQUENCE: 77

Leu Leu Cys Val Ser Glu Ala Thr Thr Val Pro Leu Ser Arg
1               5                   10

<210> SEQ ID NO 78
<211> LENGTH: 782
<212> TYPE: PRT
<213> ORGANISM: Artificial Sequence
<220> FEATURE:
<223> OTHER INFORMATION: Chimeric antigen receptor
```

<400> SEQUENCE: 78

```
Met Ala Leu Pro Val Thr Ala Leu Leu Leu Pro Leu Ala Leu Leu Leu
1               5                   10                  15

His Ala Ala Arg Pro Met Gln Val Gln Leu Val Glu Ser Gly Gly Gly
            20                  25                  30

Leu Val Gln Ala Gly Gly Ser Leu Arg Leu Ser Cys Ala Ala Ser Gly
        35                  40                  45

Arg Ala Phe Ser Ser Tyr Ala Met Gly Trp Phe Arg Gln Ala Pro Gly
    50                  55                  60

Lys Glu Arg Glu Leu Val Ala Ala Ile Ser Trp Ser Asp Asp Ser Thr
65                  70                  75                  80

Tyr Tyr Ala Asn Ser Val Lys Gly Arg Phe Thr Ile Ser Arg Asp Asn
                85                  90                  95

Ala Lys Ser Ala Val Tyr Leu Gln Met Asn Ser Leu Lys Pro Glu Asp
            100                 105                 110

Thr Ala Val Tyr Tyr Cys Ala Ala His Lys Ser Leu Gln Arg Pro Asp
        115                 120                 125

Glu Tyr Thr Tyr Trp Gly Gln Gly Thr Gln Val Thr Val Ser Ser Thr
    130                 135                 140

Thr Thr Pro Ala Pro Arg Pro Pro Thr Pro Ala Pro Thr Ile Ala Ser
145                 150                 155                 160

Gln Pro Leu Ser Leu Arg Pro Glu Ala Cys Arg Pro Ala Ala Gly Gly
                165                 170                 175

Ala Val His Thr Arg Gly Leu Asp Phe Ala Cys Asp Phe Trp Val Leu
            180                 185                 190

Val Val Val Gly Gly Val Leu Ala Cys Tyr Ser Leu Leu Val Thr Val
        195                 200                 205

Ala Phe Ile Ile Phe Trp Val Arg Ser Lys Arg Ser Arg Leu Leu His
    210                 215                 220

Ser Asp Tyr Met Asn Met Thr Pro Arg Arg Pro Gly Pro Thr Arg Lys
225                 230                 235                 240

His Tyr Gln Pro Tyr Ala Pro Pro Arg Asp Phe Ala Ala Tyr Arg Ser
                245                 250                 255

Lys Arg Gly Arg Lys Lys Leu Leu Tyr Ile Phe Lys Gln Pro Phe Met
            260                 265                 270

Arg Pro Val Gln Thr Thr Gln Glu Glu Asp Gly Cys Ser Cys Arg Phe
        275                 280                 285

Pro Glu Glu Glu Glu Gly Gly Cys Glu Leu Arg Val Lys Phe Ser Arg
    290                 295                 300

Ser Ala Asp Ala Pro Ala Tyr Lys Gln Gly Gln Asn Gln Leu Tyr Asn
305                 310                 315                 320

Glu Leu Asn Leu Gly Arg Arg Glu Glu Tyr Asp Val Leu Asp Lys Arg
                325                 330                 335

Arg Gly Arg Asp Pro Glu Met Gly Gly Lys Pro Arg Arg Lys Asn Pro
            340                 345                 350

Gln Glu Gly Leu Tyr Asn Glu Leu Gln Lys Asp Lys Met Ala Glu Ala
        355                 360                 365

Tyr Ser Glu Ile Gly Met Lys Gly Glu Arg Arg Gly Lys Gly His
    370                 375                 380

Asp Gly Leu Tyr Gln Gly Leu Ser Thr Ala Thr Lys Asp Thr Tyr Asp
385                 390                 395                 400

Ala Leu His Met Gln Ala Leu Pro Pro Arg Pro Gly Glu Gly Arg Gly
                405                 410                 415
```

Ser Leu Leu Thr Cys Gly Asp Val Glu Glu Asn Pro Gly Pro Met Trp
            420                 425                 430

Leu Gln Ser Leu Leu Leu Gly Thr Val Ala Cys Ser Ile Ser Arg
        435                 440                 445

Lys Val Cys Asn Gly Ile Gly Ile Gly Glu Phe Lys Asp Ser Leu Ser
    450                 455                 460

Ile Asn Ala Thr Asn Ile Lys His Phe Lys Asn Cys Thr Ser Ile Ser
465                 470                 475                 480

Gly Asp Leu His Ile Leu Pro Val Ala Phe Arg Gly Asp Ser Phe Thr
                485                 490                 495

His Thr Pro Pro Leu Asp Pro Gln Glu Leu Asp Ile Leu Lys Thr Val
            500                 505                 510

Lys Glu Ile Thr Gly Phe Leu Leu Ile Gln Ala Trp Pro Glu Asn Arg
        515                 520                 525

Thr Asp Leu His Ala Phe Glu Asn Leu Glu Ile Ile Arg Gly Arg Thr
    530                 535                 540

Lys Gln His Gly Gln Phe Ser Leu Ala Val Val Ser Leu Asn Ile Thr
545                 550                 555                 560

Ser Leu Gly Leu Arg Ser Leu Lys Glu Ile Ser Asp Gly Asp Val Ile
                565                 570                 575

Ile Ser Gly Asn Lys Asn Leu Cys Tyr Ala Asn Thr Ile Asn Trp Lys
            580                 585                 590

Lys Leu Phe Gly Thr Ser Gly Gln Lys Thr Lys Ile Ile Ser Asn Arg
        595                 600                 605

Gly Glu Asn Ser Cys Lys Ala Thr Gly Gln Val Cys His Ala Leu Cys
    610                 615                 620

Ser Pro Glu Gly Cys Trp Gly Pro Glu Pro Arg Asp Cys Val Ser Cys
625                 630                 635                 640

Arg Asn Val Ser Arg Gly Arg Glu Cys Val Asp Lys Cys Asn Leu Leu
                645                 650                 655

Glu Gly Glu Pro Arg Glu Phe Val Glu Asn Ser Glu Cys Ile Gln Cys
            660                 665                 670

His Pro Glu Cys Leu Pro Gln Ala Met Asn Ile Thr Cys Thr Gly Arg
        675                 680                 685

Gly Pro Asp Asn Cys Ile Gln Cys Ala His Tyr Ile Asp Gly Pro His
    690                 695                 700

Cys Val Lys Thr Cys Pro Ala Gly Val Met Gly Glu Asn Asn Thr Leu
705                 710                 715                 720

Val Trp Lys Tyr Ala Asp Ala Gly His Val Cys His Leu Cys His Pro
                725                 730                 735

Asn Cys Thr Tyr Gly Cys Thr Gly Pro Gly Leu Glu Gly Cys Pro Thr
            740                 745                 750

Asn Gly Pro Lys Ile Pro Ser Ile Ala Thr Gly Met Val Gly Ala Leu
        755                 760                 765

Leu Leu Leu Leu Val Val Ala Leu Gly Ile Gly Leu Phe Met
    770                 775                 780

<210> SEQ ID NO 79
<211> LENGTH: 2346
<212> TYPE: DNA
<213> ORGANISM: Artificial Sequence
<220> FEATURE:
<223> OTHER INFORMATION: Chimeric antigen receptor

<400> SEQUENCE: 79

```
atggccttac cagtgaccgc cttgctcctg ccgctggcct tgctgctcca cgccgccagg      60
ccgatgcagg tgcagcttgt ggagtccggc ggaggtcttg tccaggcagg agggtctttg     120
cgcctgagct gcgcggcgag tgggcgcgcg ttcagcagtt acgcgatggg ttggttccgc     180
caggcccctg ggaaagagcg tgaacttgtg gctgccattt cttggtctga tgattccacc     240
tattatgcta attcagttaa gggccgtttc acgattagcc gcgataatgc taaatccgcc     300
gtctatcttc agatgaacag ccttaagcct gaagatacgg cagtatatta ttgtgccgct     360
cataagagtc tgcaacgccc ggacgaatat acatactggg gacagggcac gcaagttacc     420
gtttccagca ccacgacgcc agcgccgcga ccaccaacac cggcgcccac catcgcgtcg     480
cagcccctgt ccctgcgccc agaggcgtgc cggccagcgg cgggggcgc agtgcacacg     540 aggggggctgg acttcgcctg tgatttctgg gtgctggtcg ttgtgggcgg cgtgctggcc     600
tgctacagcc tgctggtgac agtggccttc atcatctttt gggtgaggag caagcggagc     660
agactgctgc acagcgacta catgaacatg cccccccgga ggcctggccc cacccggaag     720
cactaccagc cctacgcccc tcccagggat ttcgccgcct accggagcaa cggggcaga      780 aagaaactcc tgtatatatt caaacaacca tttatgagac cagtacaaac tactcaagag     840
gaagatggct gtagctgccg attttccagaa gaagaagaag aggatgtgaa actgagagtg     900
aagttcagca ggagcgcaga cgcccccgcg tacaagcagg gccagaacca gctctataac     960
gagctcaatc taggacgaag agaggagtac gatgttttgg acaagagacg tggccgggac    1020
cctgagatgg ggggaaagcc gagaaggaag aaccctcagg aaggcctgta caatgaactg    1080
cagaaagata agatggcgga ggcctacagt gagattggga tgaaaggcga gcgccggagg    1140 ggcaagggc acgatggcct ttaccagggt ctcagtacag ccaccaagga cacctacgac    1200
gcccttcaca tgcaggccct gccccctcgc ccggggagg gcagaggcag cctgctgaca    1260
tgtggcgacg tggaagagaa ccctggcccc atgtggctgc agagcctgct gctcttgggc    1320
actgtggcct gcagcatctc tcgcaaagtg tgtaacggaa taggtattgg tgaatttaaa    1380
gactcactct ccataaatgc tacgaatatt aaacacttca aaaactgcac ctccatcagt    1440
ggcgatctcc acatcctgcc ggtggcattt agggggtgact ccttcacaca tactcctcct    1500
ctggatccac aggaactgga tattctgaaa accgtaaagg aaatcacagg ttttttgctg    1560
attcaggctt ggcctgaaaa caggacggac ctccatgcct tgagaaacct agaaatcata    1620
cgcggcagga ccaagcaaca tggtcagttt tctcttgcag tcgtcagcct gaacataaca    1680
tccttgggat tacgctccct caaggagata agtgatggag atgtgataat ttcaggaaac    1740
aaaaatttgt gctatgcaaa tacaataaac tggaaaaaac tgtttgggac ctccggtcag    1800
aaaaccaaaa ttataagcaa cagaggtgaa aacagctgca aggccacagg ccaggtctgc    1860
catgccttgt gctcccccga gggctgctgg ggcccggagc ccagggactg cgtctcttgc    1920
cggaatgtca gccgaggcag ggaatgcgtg gacaagtgca accttctgga gggtgagcca    1980
agggagtttg tggagaactc tgagtgcata cagtgccacc cagagtgcct gcctcaggcc    2040
atgaacatca cctgcacagg acggggacca gacaactgta tccagtgtgc ccactacatt    2100
gacggccccc actgcgtcaa gacctgcccg gcaggagtca tgggagaaaa caacaccctg    2160
gtctggaagt acgcagacgc cggccatgtg tgccacctgt gccatccaaa ctgcacctac    2220
ggatgcactg ggccaggtct tgaaggctgt ccaacgaatg gcctaagat cccgtccatc    2280 gccactggga tggtgggggc cctcctcttg ctgctggtgg tggccctggg gatcggcctc    2340
``` ttcatg 2346

<210> SEQ ID NO 80
<211> LENGTH: 340
<212> TYPE: PRT
<213> ORGANISM: Artificial Sequence
<220> FEATURE:
<223> OTHER INFORMATION: SB10 transposase

<400> SEQUENCE: 80

```
Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340
```

```
<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
ggcactgaca attccgtggt                                               20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
agggacgtag cagaaggacg                                               20

<210> SEQ ID NO 83
<211> LENGTH: 23
<212> TYPE: DNA
<213> ORGANISM: Artificial Sequence
<220> FEATURE:
<223> OTHER INFORMATION: Primer

<400> SEQUENCE: 83
acgtcctttc catggctgct cgc                                           23

<210> SEQ ID NO 84
<211> LENGTH: 22
<212> TYPE: DNA
<213> ORGANISM: Artificial Sequence
<220> FEATURE:
<223> OTHER INFORMATION: Primer

<400> SEQUENCE: 84
gctgtcatct cttgtgggct gt                                            22

<210> SEQ ID NO 85
<211> LENGTH: 21
<212> TYPE: DNA
<213> ORGANISM: Artificial Sequence
<220> FEATURE:
<223> OTHER INFORMATION: Primer

<400> SEQUENCE: 85
actcatggga gctgctggtt c                                             21

<210> SEQ ID NO 86
<211> LENGTH: 26
<212> TYPE: DNA
<213> ORGANISM: Artificial Sequence
<220> FEATURE:
<223> OTHER INFORMATION: Primer

<400> SEQUENCE: 86
cctgtcatgc ccacacaaat ctctcc                                        26

<210> SEQ ID NO 87
<211> LENGTH: 5
<212> TYPE: PRT
<213> ORGANISM: Homo sapiens

<400> SEQUENCE: 87
```

```
Ser Tyr Ala Met Gly
1               5

<210> SEQ ID NO 88
<211> LENGTH: 17
<212> TYPE: PRT
<213> ORGANISM: Homo sapiens

<400> SEQUENCE: 88

Ala Ile Ser Trp Ser Asp Asp Ser Thr Tyr Tyr Ala Asn Ser Val Lys
1               5                   10                  15

Gly

<210> SEQ ID NO 89
<211> LENGTH: 12
<212> TYPE: PRT
<213> ORGANISM: Homo sapiens

<400> SEQUENCE: 89

His Lys Ser Leu Gln Arg Pro Asp Glu Tyr Thr Tyr
1               5                   10

<210> SEQ ID NO 90

<400> SEQUENCE: 90

000

<210> SEQ ID NO 91

<400> SEQUENCE: 91

000

<210> SEQ ID NO 92
<211> LENGTH: 13
<212> TYPE: PRT
<213> ORGANISM: Homo sapiens

<400> SEQUENCE: 92

Leu Leu Cys Val Ser Glu Ala Thr Thr Val Pro Leu Ser
1               5                   10

<210> SEQ ID NO 93

<400> SEQUENCE: 93

000

<210> SEQ ID NO 94
<211> LENGTH: 25
<212> TYPE: PRT
<213> ORGANISM: Homo sapiens

<400> SEQUENCE: 94

Glu Leu Val Ala Ala Ile Ser Trp Ser Asp Asp Ser Thr Tyr Tyr Ala
1               5                   10                  15

Asn Ser Val Lys Gly Arg Ser Met Cys
            20                  25
```